United States Patent [19]

Miller et al.

[11] 4,354,244

[45] Oct. 12, 1982

[54] METHOD AND APPARATUS FOR DETERMINING THE MOISTURE CONTENT OF PARTICULATE MATERIAL THAT MAY CONTAIN AN UNKNOWN AMOUNT OF MOISTURE IN A FROZEN STATE

[75] Inventors: Christopher S. Miller, Seattle; Daniel F. Pope, Issaquah; Jon V. Hokanson, Everett, all of Wash.

[73] Assignee: Eur-Control M&D, U.S.A., Inc., Bellevue, Wash.

[21] Appl. No.: 124,339

[22] Filed: Feb. 25, 1980

[51] Int. Cl.³ .............................................. G06G 7/58
[52] U.S. Cl. .................................. 364/556; 364/568; 364/497
[58] Field of Search .................. 364/556, 568, 497; 324/61 R, 61 P, 61 QS, 61 QL, 58.5 R; 73/15 B, 76

[56] References Cited

U.S. PATENT DOCUMENTS

| | | | |
|---|---|---|---|
| 3,916,670 | 11/1975 | Davis et al. | 73/15 B |
| 4,107,599 | 8/1978 | Preikschat | 324/61 R |
| 4,174,498 | 11/1979 | Preikschat | 324/57 R |
| 4,181,881 | 1/1980 | Preikschat | 324/57 R |

*Primary Examiner*—Edward J. Wise
*Attorney, Agent, or Firm*—Christensen, O'Connor, Johnson & Kindness

[57] ABSTRACT

A sample box is provided for selectively receiving, retaining and discharging samples of particulate material during a plurality of successive measurement cycles. A data processor receives a plurality of input signals representing the measured weight of the sample box and the measured temperature, conductivity, and moisture (based on electrical impedance) of each sample. Using supplier-related data stored in a memory and entered through a keyboard and display, the data processor determines, for each sample, its wet bulk density, its electronic oven dry percentage from the moisture based on electrical impedance, and its density oven dry percentage from the wet bulk density. From the density and electronic oven dry percentages and the temperature of the sample, the data processor determines if the sample contains frozen moisture and also determines if the electronic and density oven dry percentages are based on valid input data. If both oven dry percentages are based on valid input data and if the sample does not contain frozen moisture, the data processor selects an average of the density and electronic oven dry percentages as a verified oven dry percentage. If both oven dry percentages are valid and frozen moisture is detected, the data processor determines a degree of frozenness factor for the sample from the density and electronic oven dry percentages, and selects a quantity equal to the density oven dry percentage, modified by the degree of frozenness, factor as the verified oven dry percentage. If one of the oven dry percentages is invalid and the other is valid, the data processor selects the valid oven dry percentage as the verified oven dry percentage. Through a printer, an output indication is made of at least the verified oven dry percentage for each sample. The user may, through the keyboard and display, indicate the identity of a load, or shipment, from the supplier, whereupon the data processor stores statistics data for all samples of that load in the memory for later printout. The user may also indicate to the data processor that the electronic and density oven dry percentages for a given sample are to be stored in the memory so that the supplier-related data can be corrected by the data processor upon the subsequent entry of an oven test oven dry percentage by the user. The data processor also causes a printout to be made, for each sample, of the mode by which the verified oven dry percentage was selected, and also provides a printout of warning messages when both oven dry percentages for a sample are invalid.

94 Claims, 33 Drawing Figures

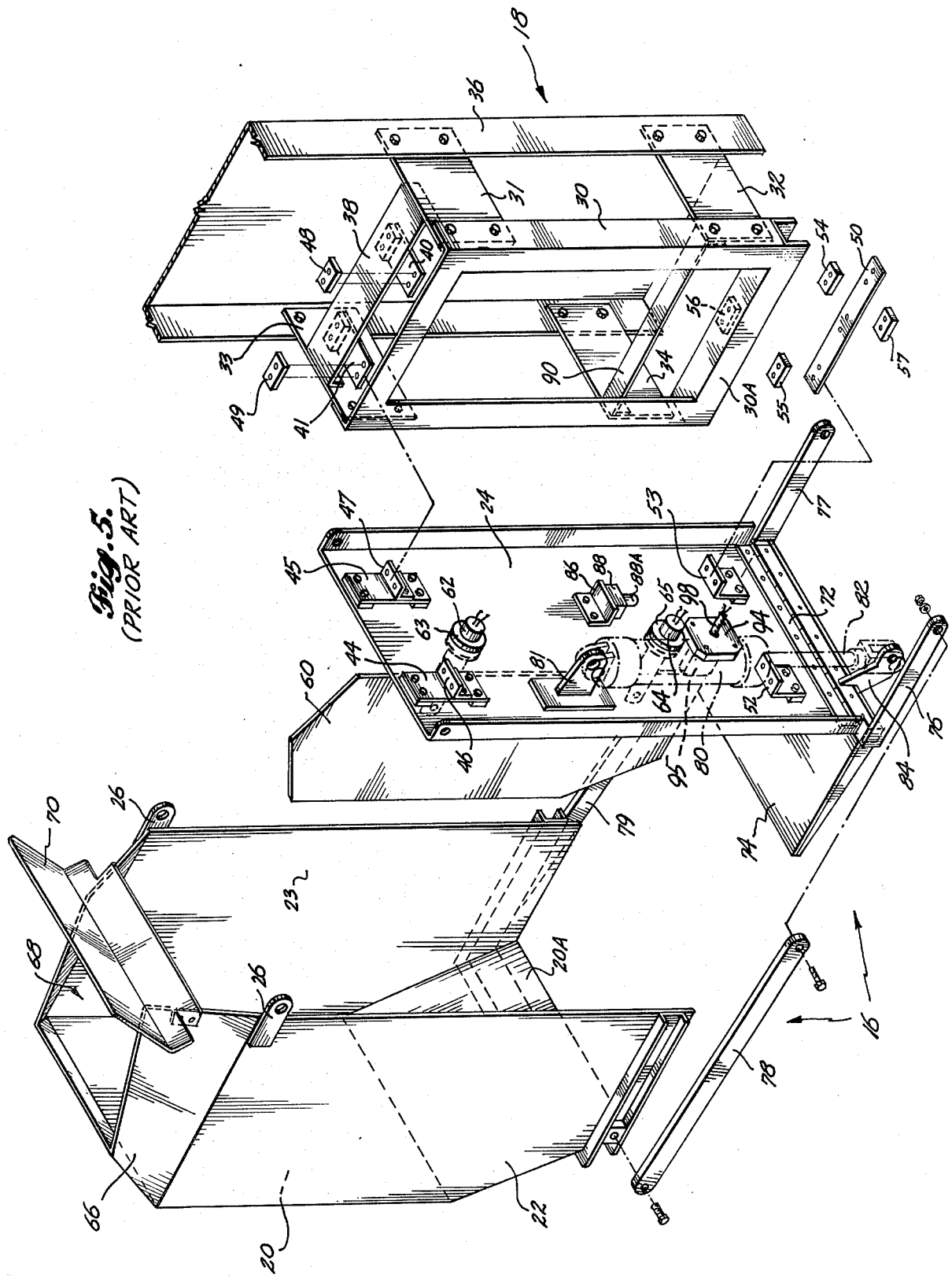

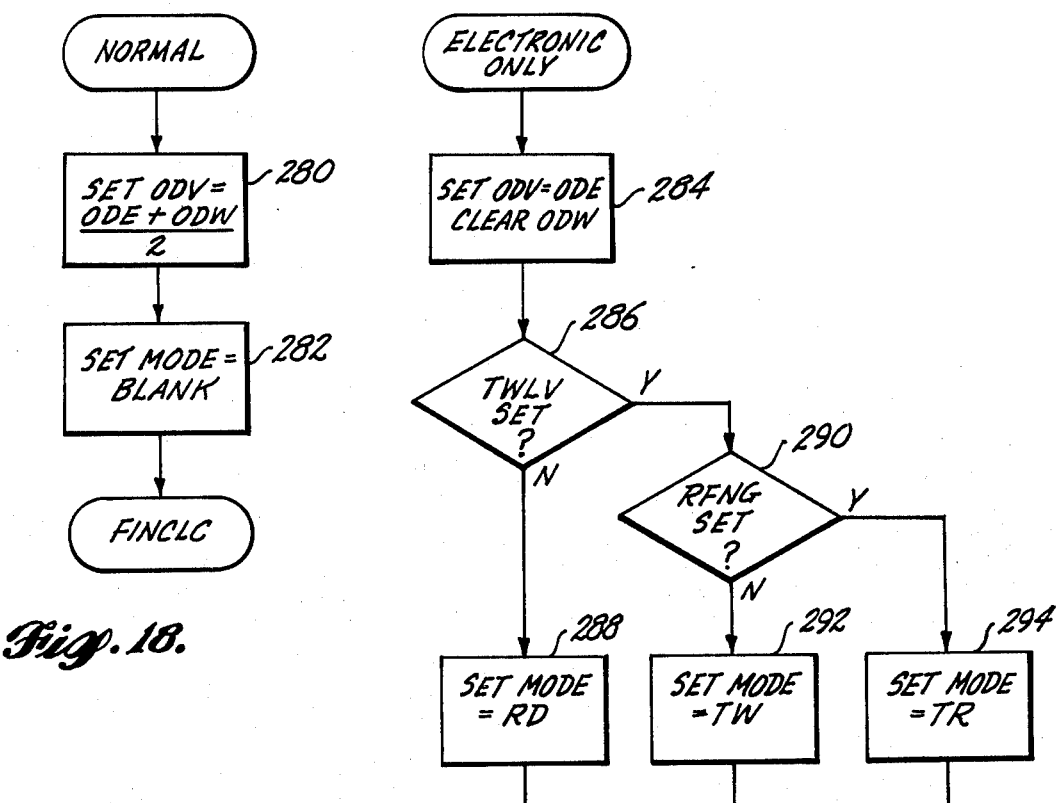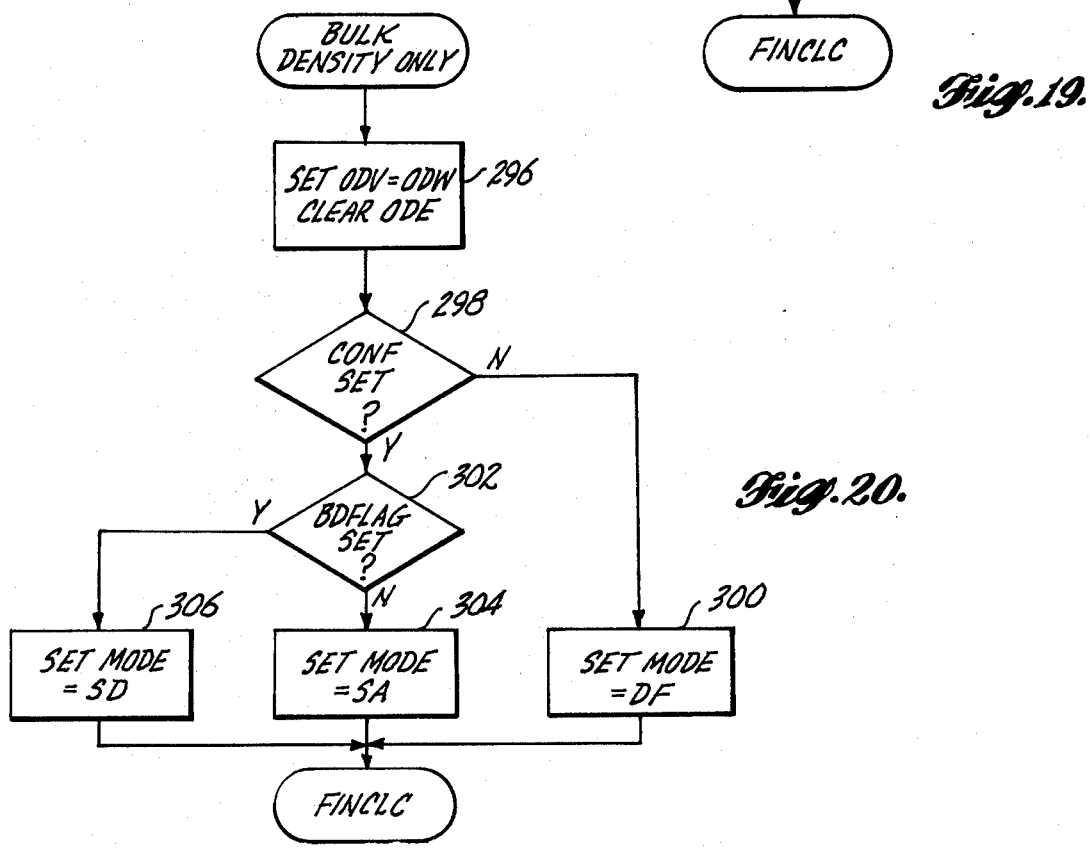
Fig. 18.
Fig. 19.
Fig. 20.

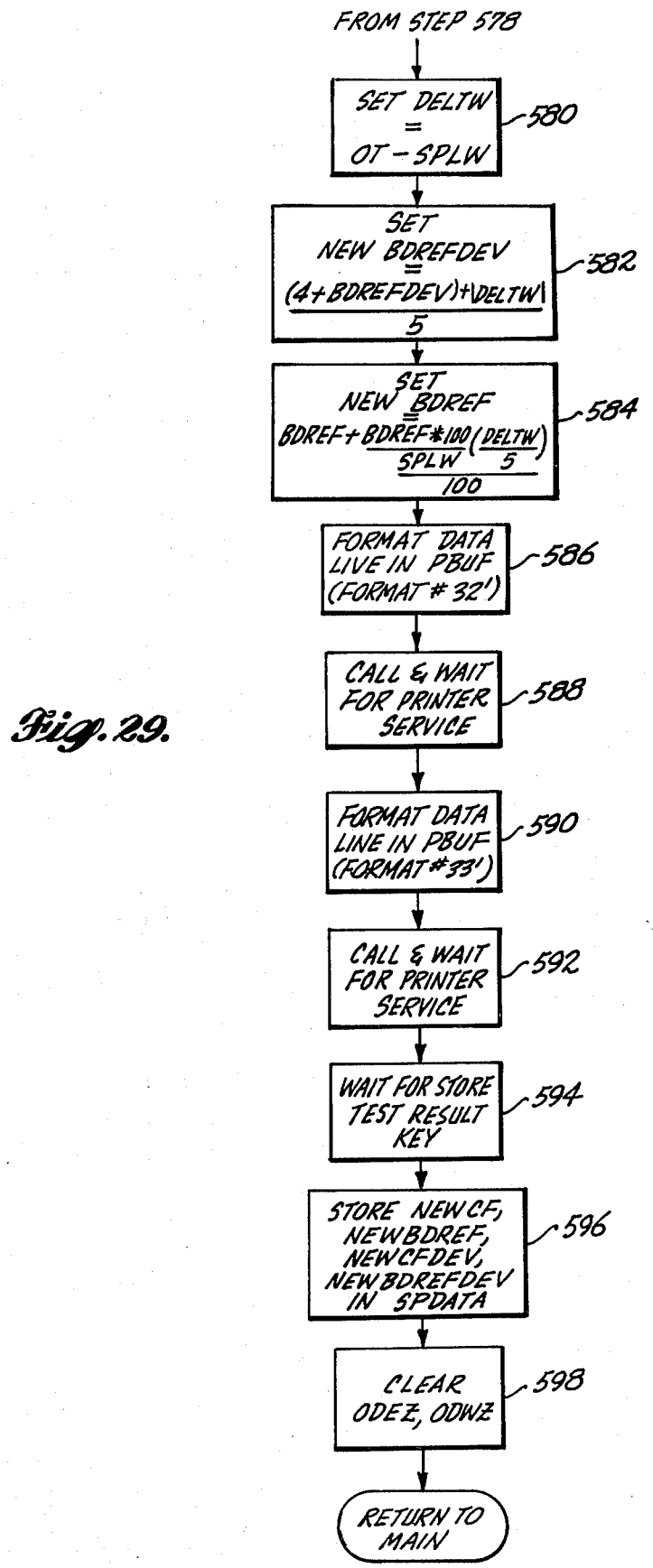

DISPLAY FORMATS

```
                 ┌──────── DISPLAY CHARACTER ────────┐
                 0   1   2   3   4   5   6   7   8   9
#1
                 X   X   X   X   X   X       X   X   X
                 └──────────┬──────────┘     └────┬────┘
                     LOAD ENTRY FIELD      SUPPLIER ENTRY FIELD
```

```
         X  X  X   -   X  X .X     X  X .X
#2       └───┬───┘ └┬┘ └───┬───┘   └───┬───┘
         SUPPLIER   CF   CORRECTION   BULK DENSITY
         NUMBER    SIGN  FACTOR ENTRY  REFERENCE ENTRY
                 (BLANK OR -)  FIELD      FIELD
```

```
         X  X       X  X .X        X  X .X
#3       └─┬─┘      └───┬──┘       └───┬──┘
         SAMPLE ID   OVEN TEST ENTRY   MEASURED RESULT
         NUMBER ENTRY    FIELD
         FIELD
```

```
         X  X  X  X  X .X       X  X .X
#4       └──────┬──────┘        └───┬──┘
            CURRENT WEIGHT         AVG. OD
```

*Fig. 30.*

PRINT FORMATS

| # | PRINTED CHARACTERS | COMMENT |
|---|---|---|
| 1 | POWER INTERRUPTION | POWER ON OR INITIALIZE |
| 2<br>3<br>4<br>5 | LOAD      XXXXXX<br>SUPPLIER   XXX  *<br>C/F - XX.X  BDREF  XX.X<br>C  ODBD  OD%  M    WET WT | START NEW LOAD KEY ACTUATED: HEADER MESSAGE FOR NEW LOAD |
| 6 | XX  XX.X  XX.X LL XXXX.X | DATA FOR EACH SAMPLE |
| 7<br>8<br>9<br>10<br>11 | AVC   AVBD  AV% OD<br>XX   XX.X   XX.X<br>DRY TONS    WET TONS<br> XXXXX.X    XXXXX.X<br>DATA STORED | START NEW LOAD KEY ACTUATED: SUMMARY MESSAGE FOR PREVIOUS LOAD |
| 12<br>13 | INCOMPLETE FILL<br>FULL XX.X  TARE XX.X | WARNING MESSAGES DURING MEASUREMENT CYCLE |
| 14 | TARE WT  HIGH   XX.X | |
| 15 | TARE WT  LOW    XX.X | |
| 16 | TARE WT  SHIFT  XX.X | |
| 17<br>18<br>19<br>20 | BOX NOT DUMPING<br>NO AIR PRESSURE?<br>SUSPENSION STUCK?<br>TRASH JAMMING BOX? | |
| 21<br>22 | RE-ENTER LOAD DATA<br>ADJUST TARE TO 1 # | |
| 23 | ELECTRONIC ONLY MODE | HEADER MESSAGE |
| 24 | BULK DENS ONLY MODE | HEADER MESSAGE |
| 25<br>26 | M%   WT   TMP CON<br>XX.X  XX.X XX  XX | PRINT METER INPUTS KEY OR SWITCH 110 ACTUATED |

*Fig. 31A.*

PRINT FORMATS

| # | PRINTED CHARACTERS | COMMENT |
|---|---|---|
| 27<br>3<br>4<br>28<br>29<br>30 | SAMPLE ID #    XX<br>SUPPLIER   XXX *<br>C/F-XX.X   BDREF   XX.X<br>M% TCW   OD%   M   C<br>XX.XXX.X   XX.X   LL   XX<br>TEMP XX   TARE XX.X | SWITCH 108 ACTUATED:<br>SUMMARY MESSAGE FOR<br>"SAMPLE TAKEN" |
| 27' | SAMPLE TAKEN FROZEN | SWITCH 108 ACTUATED:<br>FRZN SET |
| 27" | SAMPLE TAKEN | SWITCH 108 ACTUATED |
| 27<br>3<br>32<br>33<br>32'<br>33' | SAMPLE ID #   .XX<br>SUPPLIER   XXX *<br>OLD C/F - XX.X   D   XX.X<br>   BDREF XX.X   D   XX.X<br>NEW C/F   XX.X   D   XX.X<br>   BDREF XX.X   D   XX.X | SUMMARY MESSAGE<br>DURING AUTOCF |
| 34 | SUPPLIER NOT FOUND | SUPPLIER NUMBER IN DISPLAY<br>NOT IN SPLIST |
| 35<br>36 | BDREF OUT OF LIMIT<br>NEED CORRECT BDREF | BULK DENSITY REFERENCE<br>ENTERED BY USER NOT WITHIN<br>PREDETERMINED RANGE |
| 37 | ILLEGAL OVEN TEST | OVEN TEST OVEN DRY PERCENTAGE<br>NOT WITHIN RANGE |
| 38 | ILLEGAL ENTRY | KEY ACTUATION OUT OF ORDER |
| 39 | TABLE FULL | SPLIST OR LDDAT FULL |
| 3<br>4<br>40 | SUPPLIER   XXX *<br>C/F - XX.X   BDREF   XX.X<br>SUPPLIER ERASED | ERASE SUPL # KEY ACTUATED:<br>SUMMARY MESSAGE |
| 41 | ILLEGAL SAMPLE # | SAMPLE ID NUMBER<br>NOT ASSIGNED |
| 42<br>9<br>10 | SUPPLIER XXX # LOAD XXX # AVOD XX.X<br>DRY TONS    WET TONS<br>XXXXX.X    XXXXX.X | PRINT LOAD DATA KEY ACTUATED:<br>SUMMARY MESSAGE FOR EACH<br>SUPPLIER NUMBER/LOAD<br>NUMBER COMBINATION |
| 3<br>4 | SUPPLIER   XXX #<br>C/F - XX.X   BDREF   XX.X | STORE SUPPLY DATA OR<br>PRINT ALL SUPL # KEYS<br>ACTUATED |
| 31<br>43<br>44 | BAD DATA   FFFFFFFF<br>FULL   XX.X TARE XX.X C XX<br>M % XX.X   TMP XX | CPU 112 HAS GONE<br>THROUGH NO GOOD DATA |

*Fig. 31B.*

METHOD AND APPARATUS FOR DETERMINING THE MOISTURE CONTENT OF PARTICULATE MATERIAL THAT MAY CONTAIN AN UNKNOWN AMOUNT OF MOISTURE IN A FROZEN STATE

FIELD OF THE INVENTION

This invention generally relates to methods and apparatus for measuring the electrical impedance of particulate material such as wood chips in order to determine the moisture content thereof, and, more particularly, to a method and apparatus for determining the moisture content of such particulate material that may contain an unknown amount of moisture in a frozen state.

BACKGROUND OF THE INVENTION

Apparatus is known to the prior art for measuring the electrical impedance of particulate material in bulk form, such as wood chips or grain. The measurements may be made on a continuous basis, in which the material is continuously flowing past an electrode forming part of the apparatus, or on a sampling basis, in which a sample of the material is placed in a container including or forming part of the electrode.

In those apparatus which operate on a sampling basis, the apparatus may include a sample box for receiving and retaining a sample of the particulate material during measurement. An example of such a sample box is disclosed in U.S. Pat. No. 4,107,599, issued Aug. 15, 1978 to Fritz K. Preikschat, and entitled ELECTRODE FOR AN IMPEDANCE MEASURING APPARATUS. The sample box includes a grounded electrode portion which is shaped as a box having a substantially rectangular cross section. An active center electrode, typically comprising a metallic plate, is disposed in the interior of the sample box and in parallel, spaced relationship to the side walls thereof so that a uniform electrical field may be created within the sample box. The sample box has an inlet and an outlet which, together with the grounded electrode portion and the active center electrode, define a constant volume into which a sample of particulate material may be placed and retained for measurement. A temperature sensor is located within the sample box for providing a signal related to the temperature of the sample, and a weight sensor is operatively associated with the sample box so as to provide a signal related to the bulk density (weight per unit volume) of the sample.

As disclosed in U.S. Pat. No. 4,181,881, IMPROVED ELECTRICAL IMPEDANCE MEASURING APPARATUS FOR PROVIDING SEPARATE MEASUREMENTS OF THE CONDUCTIVITY AND DIELECTRIC COEFFICIENT OF VARIOUS MATERIALS, issued on Jan. 1, 1980 to Fritz K. Preikschat, a signal generator provides a high-frequency test signal which is coupled to a bridge circuit located in proximity to the sample box and interconnected with the active, center electrode and the grounded electrode portion thereof. As a result, a high-frequency electrical field is generated within the sample box, whereupon the bridge circuit provides a bridge output signal whose frequency is identical to that of the test signal. The phase of the bridge output signal, relative to that of the test signal, and the amplitude thereof are related to the electrical admittance of the sample. The signal generator also provides a reference signal whose frequency is identical to that of the test signal and whose phase is successively shifted so as to be in-phase and 90° out-of-phase with the test signal. The reference signal is supplied to a double-balanced mixer which also receives the bridge output signal. A time-multiplexed output signal from the mixer includes components successively related to the conductivity and to the dielectric coefficient of the sample, and is coupled to further signal processing circuitry which functions to compensate the time-multiplexed output signal for variations in temperature and bulk density of the sample in accordance with signals from the temperature sensor and the weight sensor. The time-multiplexed output signal is then demultiplexed to provide separate conductivity and dielectric coefficient signals which may be displayed, recorded, or supplied to a digital computer for data processing.

As is well known, the conductivity and dielectric coefficient signals are each related to the moisture content of the sample. However, the dielectric coefficient signal is typically used for determination of moisture content and may be further compensated in accordance with the value of the conductivity signal (see, for example, U.S. Pat. No. 4,174,498, APPARATUS AND METHOD FOR PROVIDING SEPARATE CONDUCTIVITY, DIELECTRIC COEFFICIENT, AND MOISTURE MEASUREMENTS OF PARTICULATE MATERIAL, issued Nov. 13, 1979 to Fritz K. Preikschat).

In measuring the electrical impedance of certain particulate material such as wood chips, it has been found that the conductivity and dielectric coefficient signals undergo substantial changes as the moisture in a sample changes between frozen and unfrozen states. For example, the value of each signal obtained when the moisture in a sample is entirely frozen may be less than half of that obtained when the moisture in the sample is completely unfrozen. Therefore, the determination of moisture content by measuring of electrical impedance of a sample is subject to significant error when the sample contains moisture in a frozen state.

Another method for the determination of moisture content of particulate material such as wood chips involves measurement of the average oven dry bulk density of a particular source of wood chips from which the sample has been taken (e.g., the average bulk density when all free moisture has been removed). The oven dry bulk density is then divided by the bulk density of the sample (e.g., that represented by the output signal from the weight sensor) with the resultant quotient comprising the oven dry, or fiber content, percentage of the sample (where moisture percentage plus fiber content percentage=100). It has also been found that the bulk density of a sample changes as the moisture in the sample changes between frozen and unfrozen states. For example, the bulk density of a sample may decrease by about 6% as the moisture within the sample changes from completely unfrozen to completely frozen. Therefore, the determination of moisture content by measuring the bulk density of a sample is also subject to significant error when the sample contains moisture in a frozen state.

The determination of moisture content is further complicated by the fact that the sample may contain moisture in unknown amounts in both frozen and unfrozen states. If is therefore difficult to determine if the sample is frozen, and if so, to determine the degree of frozenness thereof. Although the temperature of the sample may seem to be a promising indicator of the presence of frozen moisture, it has been found that the output signal from the temperature sensor of the impedance measuring apparatus may represent a measured sample temperature as high as 5° C. even though a substantial portion of the moisture is still in a frozen state. Further, it has been found that the measured sample temperature is not related in a predictable manner to the degree of frozenness of the sample. Since it has not been known how to accurately determine the presence or amount of frozen moisture in a sample, it has not been possible to provide compensation of moisture content determinations made using either the dielectric coefficient or bulk density output signals from the impedance measuring apparatus.

Accordingly, it has been thought desirable to completely thaw the wood chips before any measurement of moisture content is made. In order to accomplish such thawing, various thermal and RF heating methods have been proposed. Because of the low thermal conductivity of wood chips, most heating methods are impractical. For wood chips having a typical thickness of one inch, a time period up to ten minutes is required to conduct enough heat into the interior of each chip to convert the moisture to its unfrozen state, assuming ideal conditions with a 100° C. temperature gradient between the exterior and interior of each chip. In addition to the long thawing times required, heating methods oftentimes appreciably affect the moisture content of the sample inasmuch as a certain portion of the moisture is converted during thawing from its unfrozen to its vaporized state. Accordingly, thawing of wood chips prior to moisture content measurement has not proved to be satisfactory.

It is therefore an object of this invention to provide an improved method and apparatus for determining the moisture content of a sample of particulate material such as wood chips.

It is a further object of this invention to provide such a method and apparatus which does not require thawing of the sample prior to moisture content measurement.

It is yet a further object of this invention to provide such a method and apparatus which provide accurate measurement of moisture content, notwithstanding the fact that a portion of the moisture within the sample may be in a frozen state.

It is another object of this invention to provide a method and apparatus which utilizes a plurality of computational techniques for determining moisture content of a sample of particulate material, and which is operative to select one of these techniques in response to various measured parameters of the sample.

It is still another object of this invention to provide a method and apparatus for determining the moisture content of a sample of particulate material which is particularly adapted for use with a sample box and an impedance measuring apparatus of the type disclosed in the aforementioned U.S. Pat. Nos. 4,107,599 and 4,181,881, and which is preferably embodied in a programmed microprocessor consisting of readily-available, integrated circuit chips.

SUMMARY OF THE INVENTION

The foregoing objects, as well as additional objects and advantages that will be apparent from a consideration of the following portion of the specification, are achieved in both methods and apparatus for determining the moisture content of a sample of particulate material such as wood chips.

In the methods of the present invention, the detection of the presence of frozen moisture in a sample of particulate material is made by determining a moisture percentage for the sample by measuring the electrical impedance thereof, and by determining the wet bulk density and temperature of the sample. An electronic oven dry percentage for the sample is determined from the moisture percentage based on electrical impedance, and a density oven dry percentage for the sample is determined from the wet bulk density of the sample. Both oven dry percentages represent a determination of the fiber content of the sample. Frozen moisture is detected if the temperature of the sample is below a predetermined value and if the electronic oven dry percentage differs from the density oven dry percentage by a predetermined amount.

The electronic oven dry percentage is determined as a function of the moisture percentage based on electrical impedance and a correction factor, with the correction factor being related to the particulate material from which the sample was taken. The density oven dry percentage is determined as a function of a bulk density reference and the measured wet bulk density of the sample, with the bulk density reference being substantially equal to an average oven dry bulk density of the particulate material from which the sample was taken.

In a preferred embodiment of the invention, the particulate material comprises wood chips, and frozen moisture is detected when the sample temperature is below substantially 5° C. and the electronic oven dry percentage is greater than the density oven dry percentage by substantially 5%.

Once frozen moisture has been detected in a sample, a verified oven dry percentage is determined by determining a factor related to the degree of frozenness of the sample from the electronic and density oven dry percentages for the sample, and by modifying the density oven dry percentage in accordance with the degree of frozenness factor. Preferably, the degree of frozenness factor is equal to the product of a scaling constant k and a quantity $\Delta$ which is substantially equal to the difference between the electronic and density oven dry percentages for the sample.

In the case where the particulate material comprises wood chips, the scaling constant k is substantially constant for all wood chips, notwithstanding their source or type, and is substantially 0.25. Preferably, the quantity $\Delta$ is equal to the electronic oven dry percentage for the sample, minus the density oven dry percentage for the sample, and minus an empirically determined constant m which is at least equal to the normal variation between the electronic and the density oven dry percentages when frozen moisture is not present in a sample. For wood chips, m is substantially 5%.

The apparatus of the present invention is particularly adapted for determining a verified oven dry percentage for each of a plurality of successive samples of the particulate material. The apparatus comprises a sample box for successively receiving, retaining, and discharging samples of the particulate material, a weight sensor operatively associated with the sample box for providing a weight signal related to the weight thereof, a temperature sensor operatively associated with the sample box for providing a temperature signal related to the temperature of a sample within the sample box, and an impedance measuring apparatus operatively associated with the sample box for providing conductivity and moisture signals respectively related to the measured electrical impedance of a sample with the sample box. Also provided is a timer means for providing a timing signal establishing a plurality of successive measurement cycles, and a data processor which operates under control of a stored program.

In a preferred embodiment, the data processor is operative to:

receive the weight, temperature, conductivity and moisture signals, and the timing signal; control the sample box so that the sample box receives, retains and discharges the sample of the particulate material during each measurement cycle; determine the wet bulk density of each sample from the weight signal; determine the electronic oven dry percentage for each sample from the moisture signal; determine a density oven dry percentage for each sample from the wet bulk density; test the temperature signal, the electronic oven dry percentage and the density oven dry percentage to detect the presence of frozen moisture in any sample; and, upon the detection of frozen moisture in a sample, determine a degree of frozenness factor for the sample from the electronic and the density oven dry percentages therefor, and select as the verified oven dry percentage a quantity equal to the density oven dry percentage for the sample, modified in accordance with the degree of frozenness factor.

If frozen moisture is not detected in the sample, the data processor is further operative to select as the verified oven dry percentage an average of the electronic and density oven dry percentages therefor. If either of the electronic and density oven dry percentages for a sample are invalid, the data processor is operative to select the other oven dry percentage if the other oven dry percentage is itself valid. If neither the electronic nor the density oven dry percentages for a sample are valid, then no verified oven dry percentage is selected by the data processor.

In order to determine whether either the electronic or the density oven dry percentage for a sample is invalid, the data processor conducts certain tests on the values of those oven dry percentages determined during each measurement cycle and also on the underlying data used to determine the oven dry percentages.

The data processor has operatively associated therewith an output means, preferably a printer, for providing an output indication of at least the verified oven dry percentage of each sample, together with an output indication of the mode by which the verified oven dry percentage was selected. If no verified oven dry percentage was selected for a sample, the data processor also causes the output means to provide an output indication of the reason for the failure to select a verified oven dry percentage.

A bulk density reference and a correction factor may be chosen for each supplier or source of particulate material, and entered through a data entry and command means operatively associated with the data processor and preferably comprising a keyboard and a display. This data is stored in a plurality of supplier-related data entries in a memory means operatively associated with the data processor. The data and command entry means is further adapted to provide a supplier indication to the data processor which represents the identity of a supplier whose particulate material is currently being sampled, and the data processor is operative to retrieve that one of the plurality of supplier-related data entries from the memory means that corresponds to the supplier indication, to determining the density oven dry percentage for each sample as a function of the bulk density reference in the thus-retrieved supplier data entry and the wet bulk density of the sample, and to determine the electronic oven dry percentage for each sample as a function of the moisture signal for a sample and the correction factor in the thus-retrieved supplier-related data entry.

The memory means is further adapted to store, under control of the data processor, a density-only command in each supplier-related data entry, with the density-only command being entered through the data and command entry means along with a supplier indication. The data processor is responsive to select the density oven dry percentage as the verified oven dry percentage for all samples of particulate material from a supplier if the density-only command has been entered into the corresponding supplier-related data entry.

The memory means is further adapted to store, under control of the data processor, a plurality of load-related data entries, with each load-related data entry being related to one of the plurality of supplier-related data entries so as to establish a supplier/load combination. Each load-related data entry includes statistics data for a load or shipment of particulate material from the corresponding supplier. The identity of any given load is entered into the data processor through the data entry and command means. Preferably, the statistics data in each load-related data entry includes at least an average oven dry bulk density for the corresponding load. The data processor is also operative to determine an average conductivity and an average verified oven dry percentage for each load. In the case where a weightometer is provided, an output signal from the weightometer is used by the data processor to determine the total wet weight of a load. From the total wet weight of a load, the total dry weight of the load is determined from the total wet weight and the average oven dry bulk density for the load, with the total wet weight and the total dry weight also being stored in the load-related data entry that corresponds to the load.

Through the data entry and command means, the data processor may be instructed to select either the electronic oven dry percentage or the density oven dry percentage as the verified oven dry percentage for all subsequent samples of a load.

In order to permit correction of the bulk density reference and correction factor for a supplier, the memory means is further adapted to store, under control of the data processor, a plurality of sample taken data entries, each of which is related to a particular supplier. In response to a sample taken command from the data and command entry means, the data processor is operative to store, in one of the sample taken data entries, the electronic and density oven dry percentages determined in a measurement cycle being processed at the time that the sample taken command was provided, and, a supplier code relating to the supplier. The data processor than assigns a sample ID number to the sample taken data entry, and causes the output means to provide an output indication of the sample taken data entry.

The bulk density reference and correction factor for a supplier may be corrected by the user from the data within a plurality of such sample taken data entries and from data obtained from oven testing of the samples. The corrected bulk density reference and correction factor are then entered into the memory means through the data entry and command means. Alternatively, the data processor provides automatic correction of the bulk density reference and correction factor for a supplier after the user has determined an oven dry percentage by oven testing corresponding to a sample, and has entered the oven test oven dry percentage into the data processor. The data processor is operative to retrieve the supplier code, the electronic oven dry percentage, and the density oven dry percentage from the sample taken data entry that corresponds to the sample ID number of the sample that has been subjected to oven testing, and updates the values of the bulk density reference and the correction factor in that one of the plurality of supplier-related data entries that corresponds to the supplier in the thus-retrieved supplier code in accordance with the thus-entered oven test oven dry percentage.

BRIEF DESCRIPTION OF THE DRAWINGS

The invention can best be understood by reference to the following portion of the specification, taken in conjunction with the accompanying drawings in which:

FIG. 5 is an exploded pictorial view showing the sample box and support of FIG. 2;

FIG. 18 is a flow chart of the program steps undertaken by the microprocessor in a NORMAL subroutine;

FIG. 19 is a flow chart of the program steps undertaken by the microprocessor in an ELECTRONIC ONLY subroutine;

FIG. 20 is a flow chart of the program steps undertaken by the microprocessor in a BULK DENSITY ONLY subroutine;

FIGS. 26-29 are a flow chart of the program steps undertaken by the microprocessor in an AUTOCF subroutine;

FIG. 30 is a chart illustrating various display formats produced by a display of FIG. 8 under control of the microprocessor; and, FIGS. 31A and 31B are a chart illustrating various print formats produced by a printer of FIG. 8 under control of the microprocessor.

DESCRIPTION OF A PREFERRED EMBODIMENT

Figure 1:
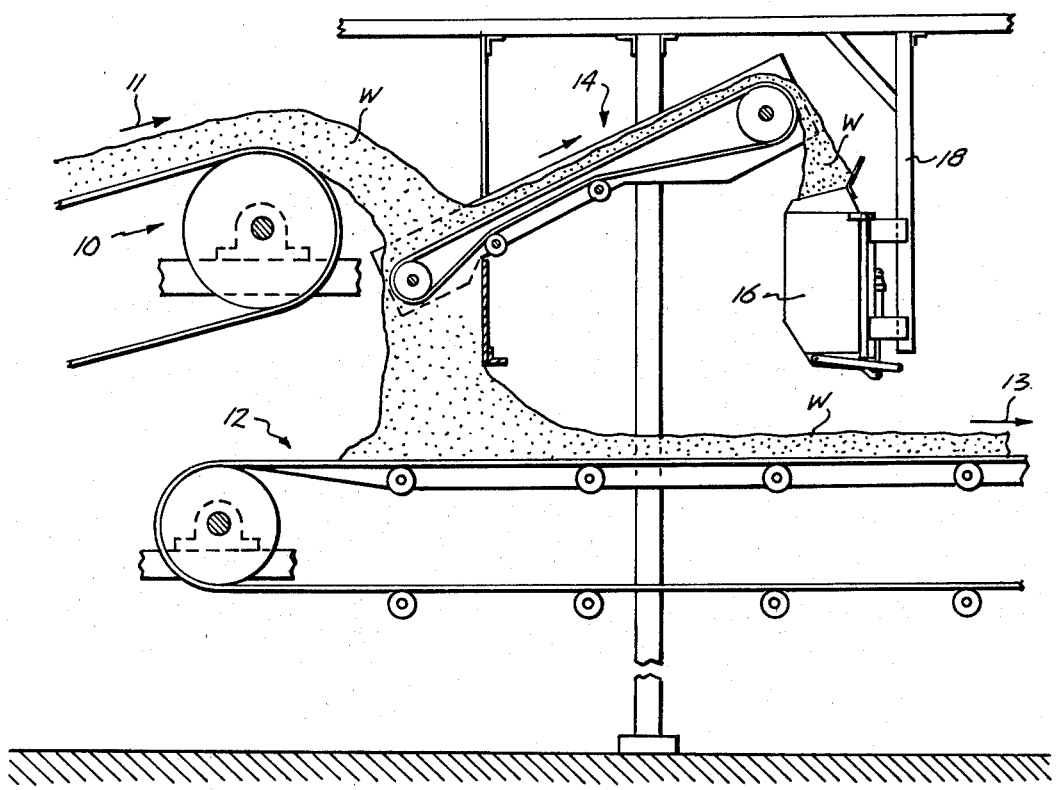
FIG. 1 is an elevation view showing a typical arrangement known to the prior art for sampling wood chips in order to measure the electrical impedance, bulk density, and temperature thereof.
Figure 2:
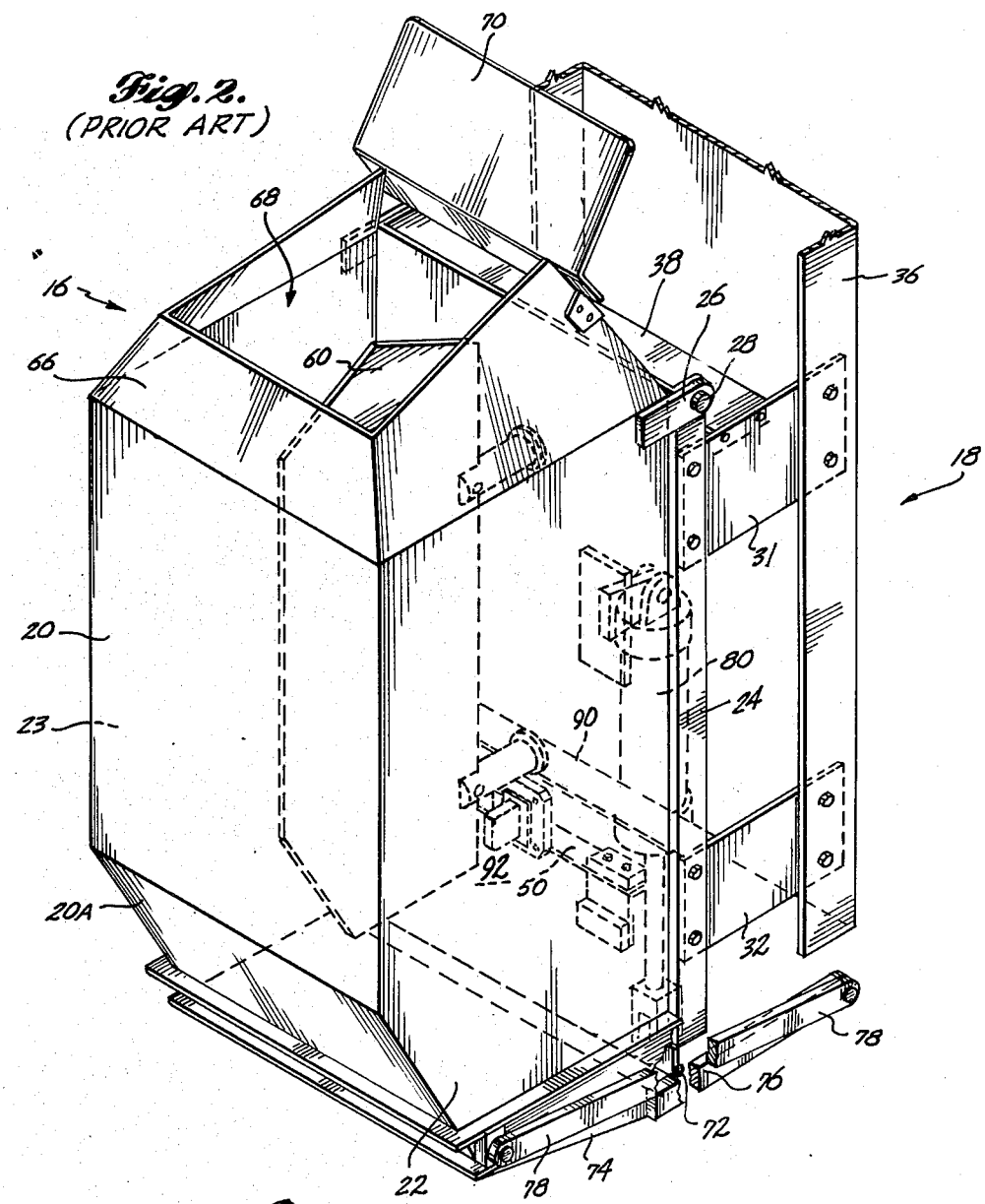
FIG. 2 is a pictorial view showing a sample box and a support for the sample box, as known to the prior art.

In FIG. 1, an arrangement is shown for taking successive samples of wood chips and conducting certain measurements thereon during successive measurement cycles. Wood chips W are carried by the belt of a first main conveyor 10 in the direction of arrow 11 and dumped at the end of conveyor 10 onto a belt of a second main conveyor 12 and then carried thereon in the direction of arrow 13. A sampling conveyor 14 has a first end thereof disposed in the stream of wood chips W falling from conveyor 10 to conveyor 12 and serves to transport a portion of the wood chips W to its second end, whereupon the wood chips W are dumped into the inlet of a sample box 16 which is held second conveyor 12 by a support 18.

In operation, conveyors 10 and 12 are continuously in motion so that wood chips W are being continuously dumped onto conveyor 12. At the start of a measurement cycle, sample box 16 is full. Measurements of conductivity, dielectric coefficient and temperature of the sample are made, as is a measurement of the full weight of sample box 16. Then, sample box 16 is emptied by opening the outlet thereof, the outlet is closed, and the empty weight of sample box 16 is measured. Thereafter, the sampling conveyor 14 is started, resulting in the wood chips W being dumped into the inlet of sample box 16 until such a time as sample box 16 is filled. Sampling conveyor 14 is then stopped and the measurement cycle is repeated.

With reference now to FIGS. 2-5, the embodiment of sample box 16 and support 18 therefor is similar to the sample box and support disclosed in U.S. Pat. No. 4,107,599. As such, this embodiment is well-suited for use in measuring the electrical impedance, temperature, and bulk density of irregularly shaped particulate material such as wood chips. Sample boxes which are particularly adapted for sampling wood chips normally require a sensing electrode geometry which differs from that used with other particulate material such as grain.

For example, wood chips, unlike grain, are not free flowing and have a tendency to "bridge" or become wedged together while flowing, and such tendency is more acute if the chips are required to flow through a constrained passageway. For these reasons, it is desirable that impedance and other measurements be done on a sampling basis such as the case with the apparatus shown in FIG. 1. Also, it has been found that discharging of the wood chips after measurement should be positive to breakdown any tendency of the wood chips to bridge so that each sample of wood chips will be completely discharged from the sample box before the next sample is taken.

The embodiment of sample box 16 and support 18 disclosed in FIGS. 2-5 includes a grounded electrode portion which is shaped as a box having a substantially rectangular cross section. The grounded electrode portion of sample box 16 comprises a front wall 20, side walls 22 and 23, and backing plate 24, together forming the closed walls of a rectangular container. Front wall 20 and side walls 22 and 23 are preferably integrally connected. A pair of arms 26 extend from the upward, rear portions of side walls 22 and 23 and, together with pivot pins 28 secured to adjacent portions of backing plate 24, form a pivotal support for side walls 22, 23 and front wall 20.

Support 18 is seen to comprise a support frame 30 which is rigidly attached to a support channel 36 by a pair of upper plates 31, 33 and a pair of lower plates 32, 34. A bracket 38 extends between and is secured to upper plates 31, 33. First ends of a pair of flat springs 40, 41 are each interposed between blocks 42, 43. The assembly of block 42, spring 40, and block 43, and the assembly of block 42, spring 41, and block 43 are secured to the under side of bracket 38 at spaced-apart locations thereon by appropriate fasteners. Secured to the rear surface of backing plate 24, at spaced-apart locations corresponding to the spaced-apart locations of springs 40 and 41, are plates 44 and 45 which in turn support respective angles 46 and 47. Second ends of springs 40 and 41 are interposed between angles 46, 47 and blocks 48 and 49, respectively, with the assemblies of angle 46, the second end of spring 40 and block 48, and of angle 47, the second end of spring 41 and block 49 being each secured together by appropriate fasteners.

Therefore, springs 40 and 41 function to provide resilient upper supports for the backing plate 24. A resilient lower support is afforded by a third flat spring 50 whose center portion is interposed between a block 56 and a block 57, with the assembly of block 56, the center portion of spring 50 and block 57 being secured by appropriate fasteners to the underside of a lower channel portion 30A of the support frame 30. When so secured, flat spring 50 extends parallel to the lower channel 30A and terminates in first and second ends. The first end of spring 50 is interposed between a block 54 and an angle 52 which is secured to backing plate 24, with the assembly of block 54, the first end of flat spring 50 and angle 52 being secured together by appropriate fasteners. Likewise, the second end of spring 50 is interposed between a block 55 and an angle 53 which is secured to the rear surface of backing plate 24, at a location spaced-apart from angle 52, with the assembly of block 55, the second end of flat spring 50 and angle 53 being secured together by appropriate fasteners.

In this manner, backing plate 24 is allowed to have unimpeded vertical displacement relative to support 18 for the purposes to be hereinafter described.

An active center electrode 60, comprising a metallic plate, is vertically disposed in the interior of the sample box defined by backing plate 24, side walls 22, 23 and front wall 20 and in parallel, spaced relationship to side walls 22 and 23 so that a uniform electrical field may be created within sample box 16. An upper rod 62 and a lower rod 64 have respective first ends secured to the electrode 60 and are in turn supported from backing plate 24 by respective insulating bushings 63, 65 so that the electrode 60 vertically extends in a plane passing through a vertical centerline of backing plate 24 and therefore along the approximate centerline of the sample box 16. A top portion 66 of sample box 16 is preferably integrally formed with front wall 20 and side walls 22 and 23 such that top portion 66 extends inwardly to create inclined walls, which, together with a deflector 70 secured to the top portion 66 define an opening 68 which comprises the inlet to the sample box 16.

At the lower end of sample box 16, a hinge 72 is provided which is secured to backing plate 24 and which mounts a trapdoor 74 for pivotal movement between an open and a closed position. In the closed position, as particularly illustrated in FIGS. 2, 3 and 5, trapdoor 74 extends horizontally from backing plate 24 and closes the lower end of sample box 16. Front wall 20 is tapered or inclined inwardly at its lower end 20A, both to give the three wall configuration forming the pivoting portion of the sample box 16 additional rigidity and to reduce the size of trapdoor 74. Additionally, this tapering reduces the outward extent of movement of wall 20 in the open position (FIG. 4), thereby reducing the forward clearance required during discharge of the sample.

Figure 4:
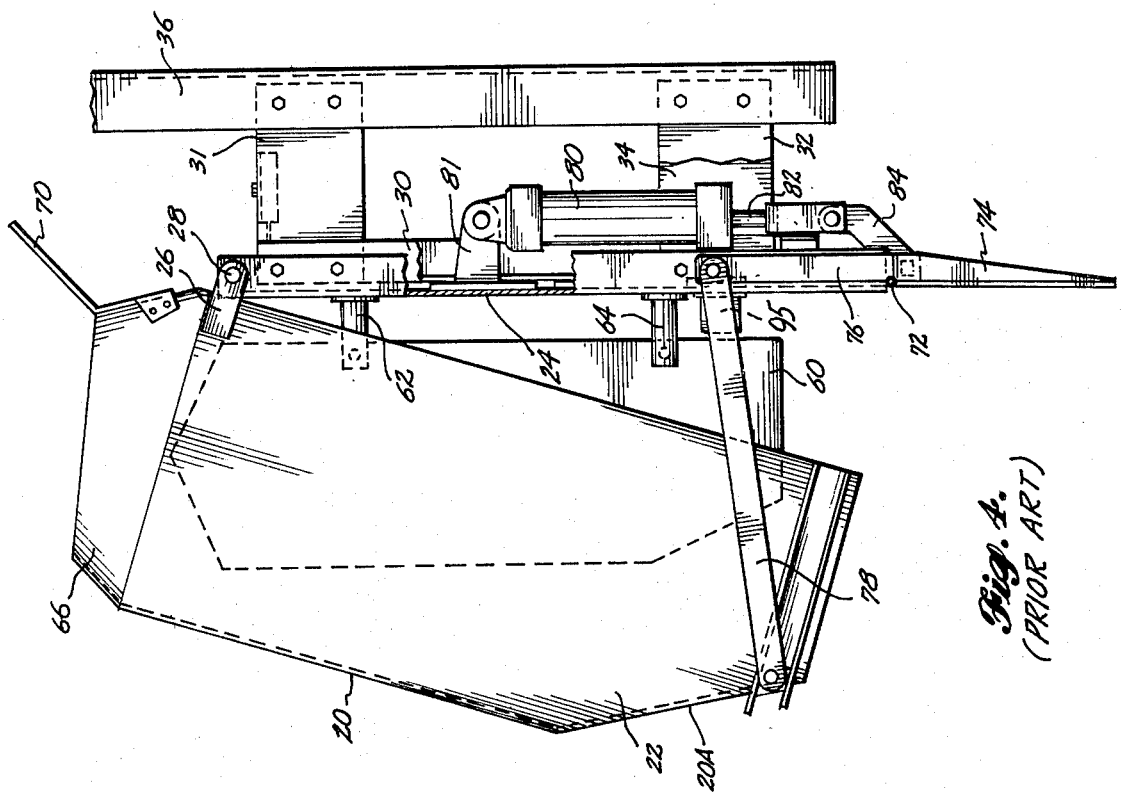
FIGS. 3 and 4 are, respectively, side elevation views showing the sample box of FIG. 2 in wood chip receiving and discharging positions.
Figure 3:
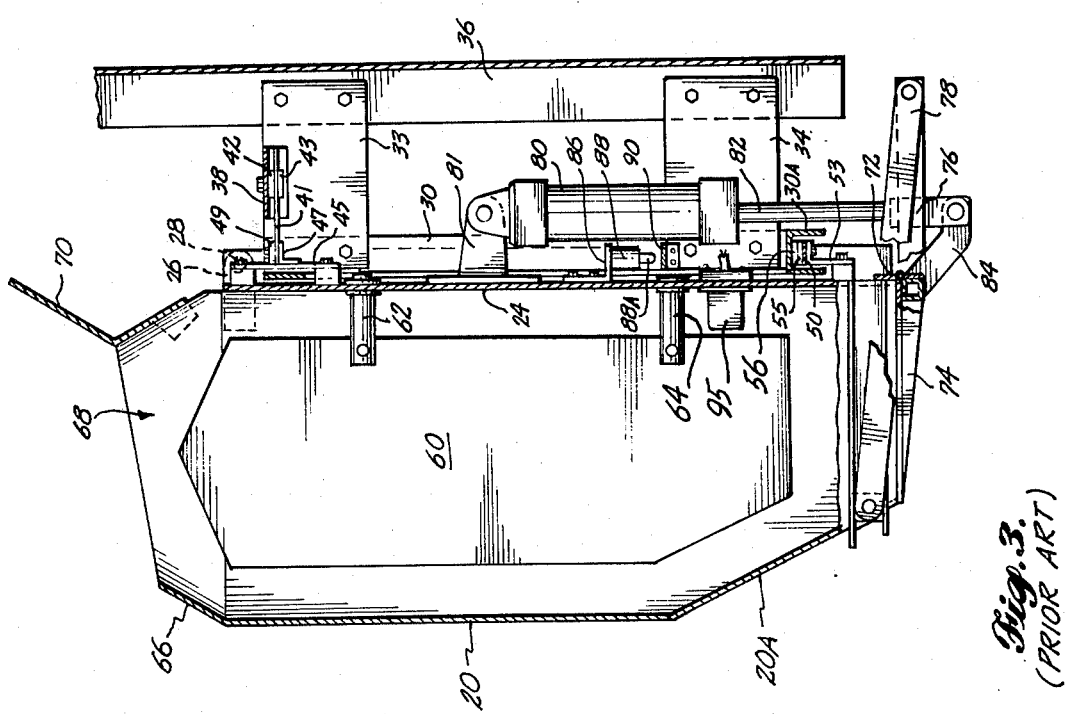

As indicated previously, a desirable feature of a sample box is that the sample box have a positive action during discharge to break any bridging tendency of the wood chips. Accordingly, sample box 16 pivots at its upper end to open outwardly, thereby causing a sudden relative movement between center electrode 60 and side walls 22 and 23. To cause this pivotal action, one end of each of a pair of first linkage arms 76, 77 is fixedly attached to either side of trapdoor 74. The second end of each first linkage arm 76, 77 is pivotally attached to one end of a pair of second linkage arms 78, 79. The other end of each second linkage arm 78, 79 is pivotally secured to the forward portion of each side wall 22, 23. As is apparent from a comparison of FIG. 3, illustrating the sample box 16 in its closed position, with FIG. 4, illustrating the sample box 16 in its open position, movement of trapdoor 74 from its horizontal position to its vertical position causes, through linkage arms 76, 77 and 78, 79, an outward movement of the walls 20, 22 and 23 of sample box 16, thus discharging the sample.

The mechanical force required to move the sample box 16 between its open and closed positions is provided by an actuating means 80. The actuating means 80 is mounted on the rear surface of backing plate 24 by a bracket 81 and includes a control rod 82 which is pivotally attached at its outward end to an arm 84 extending from and secured to trapdoor 74. Movement of control rod 82 between a retracted and an extended position causes both pivotal movement of trapdoor 74 between its horizontal and vertical positions and outward movement of the front wall 20 and side walls 22 and 23 via linkage arms 76, 77 and 78, 79. In a preferred form, actuating means 80 is a pneumatically actuated cylinder and piston.

A load cell 85 is secured to an angle 86 which in turn secured to the rear surface of backing plate 24. Load cell 88 has an actuator 88A which, in assembly, bears upon a bar 90 extending between and secured to the lower plates 32, 34. Since backing plate 24 is free to move vertically with respect to support 18 by virtue of the upper supports afforded in part by springs 40 and 41 and the lower support afforded in part by spring 50, it will be seen that load cell 88 provides an output signal which is related to the weight of the sample within sample box 16. Since sample box 16 defines a constant volume, it will also be seen that the output signal of weight sensor 88 is related to the bulk density of the sample.

Figure 6:
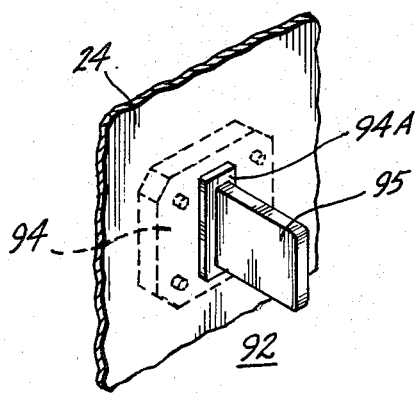
FIG. 6 is a pictorial view showing a temperature sensor mounted on the sample box, as known to the prior art.
Figure 7:
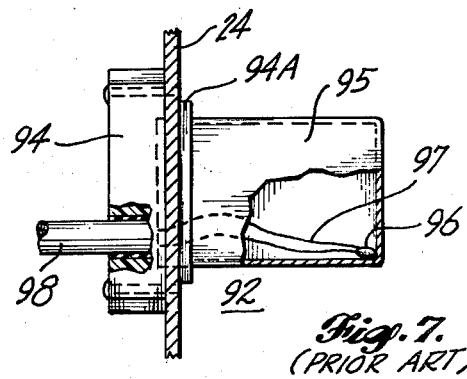
FIG. 7 is a partial side elevation view of the temperature sensor of FIG. 6.

A temperature sensor 92 is mounted on the interior of backing plate 24 immediately below lower rod 64. At best seen in FIGS. 6 and 7, the temperature sensor 92 comprises a base 94, of electrical and thermal insulating material, which is secured to the rear surface of backing plate 24 by a plurality of appropriate fasteners. Base 94 has an integral, central projection 94A which projects through a corresponding aperture in backing plate 24 and which in turn supports a housing 95 which comprises a conventional crystal can of thermally conductive material, such as a nickel-plated nickel alloy. A thermistor 96 is adhesively secured within housing 95 towards the projecting tip thereof, with thermistor 96 having a pair of leads 97 which are interconnected with a cable 98 secured in and passing through base 94. The temperature sensor 92 accordingly provides an output signal which is related to the temperature of the sample within sample box 16.

Figure 8:
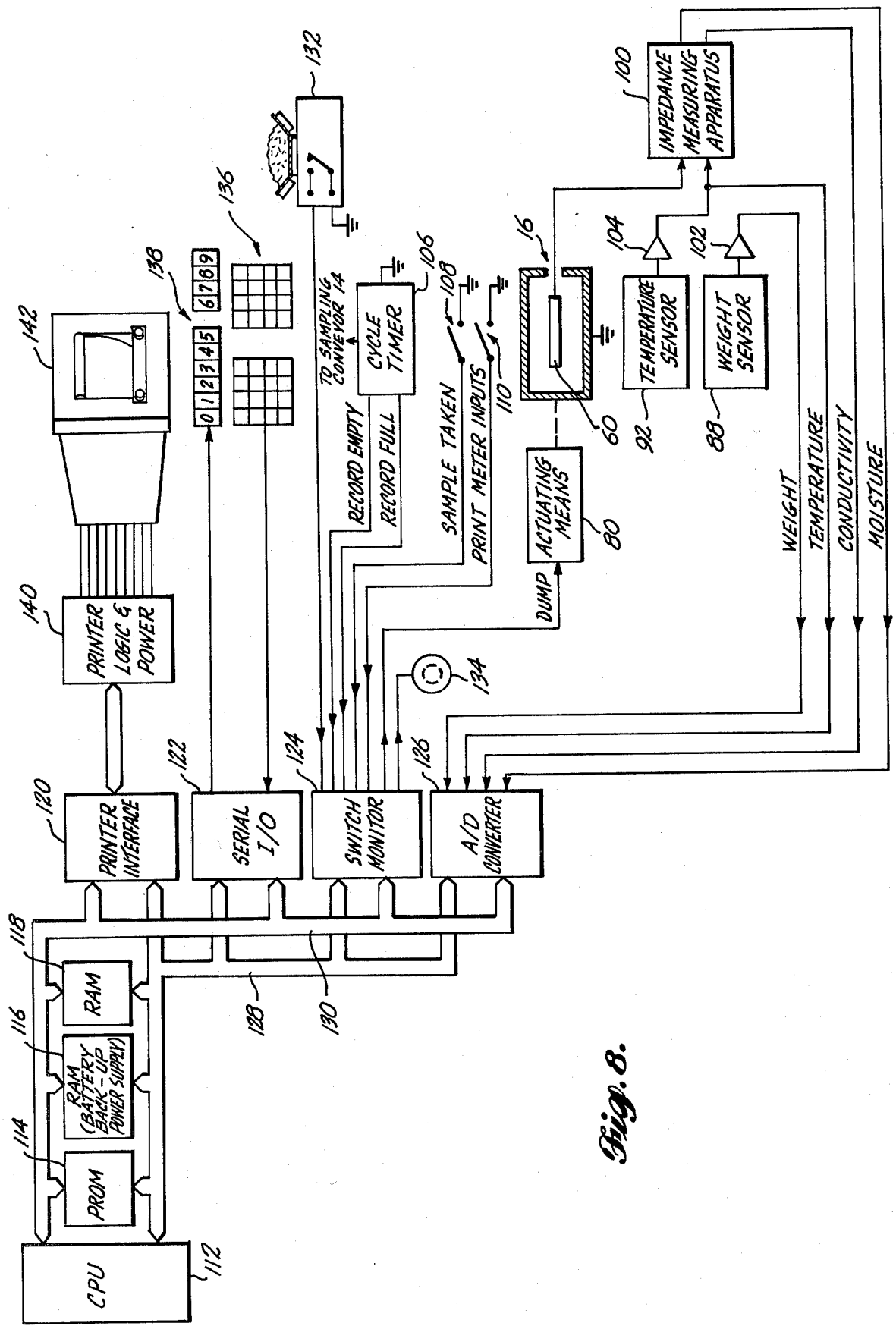
FIG. 8 is an electrical block diagram of the apparatus of the present invention, including a microprocessor and various input/output devices associated therewith, including an impedance measuring apparatus.

With reference now to FIG. 8, the active center electrode 60 of sample box 16 is interconnected with an impedance measuring apparatus 100 which is preferably similar to the type disclosed in U.S. Pat. No. 4,181,881 (incorporated herein by reference). The output signals from weight sensor 88 and temperature sensor 92 are respectively coupled to the inputs of amplifiers 102, 104 which provide output signals respectively proportional to the weight of sample box 16 and to the temperature within sample box 16. The temperature signal from amplifier 104 is coupled to an input of impedance measuring apparatus 100. As described in more detail in U.S. Pat. No. 4,181,881, impedance measuring apparatus 100 includes a bridge circuit which is used to supply a high frequency test signal to the interior of sample box 16 via active center electrode 60. Unbalance in the bridge circuit caused by a sample within sample box 16 is used to determine the conductance (1/R) and the susceptance ($j\omega C$) components of the electrical admittance of the sample. After compensation of the conductance and susceptance components for temperature variations in accordance with the temperature signal, impedance measuring apparatus 100 provides a conductivity signal proportional to the measured conductivity of the sample and a "moisture" signal proportional to the measured dielectric coefficient of the sample. The weight, temperature, conductivity and moisture signals are each in analog form and are supplied to the microprocessor illustrated in FIG. 8 as described hereinafter.

The various measurements made by weight sensor 88, temperature sensor 92, and impedance measuring apparatus 100 are made during successive measurement cycles which are determined by a cycle timer 106 located in the vicinity of sample box 16. At the beginning of each measurement cycle, cycle timer 106 provides a record full signal (which may comprise a short pulse). At a predetermined time after each record full signal, cycle timer 106 provides a record empty signal (which may also comprise a short pulse). Each measurement cycle is defined by the interval between successive record full signals which typically may be 1.5 minutes. In addition, cycle timer 106 provides a signal to sampling conveyor 14, whereby sampling conveyor 14 is started subsequent to each record empty signal and stopped prior to each record full signal.

The record full and record empty signals are supplied to the microprocessor. At the time of each record full signal, sample box 16 has been filled with wood chips and accordingly contains a sample thereof. In response to each record full signal, the microprocessor stores the values of the weight, temperature, conductivity and moisture signals for the sample, and undertakes certain computations and other actions described hereinafter. As can be appreciated, the value of the weight signal thus stored is proportional to the full weight of sample box 16 including the sample. Thereafter, the microprocessor provides a dump output signal to actuating means 80, which responsively discharges the sample from sample box 16 as previously described. At the time of the subsequent record empty signal, the sample should have been completely discharged from sample box 16. In response to the record empty signal, the microprocessor stores the value of the weight signal, with the thus-stored value being proportional to the empty or tare weight of sample box 16, and undertakes certain computations and other actions described hereinafter. Thereafter, sampling conveyor 14 is started by cycle timer 106 and sample box 16 is again filled, whereupon a measurement cycle for the next sample is initiated at the subsequent record full signal from cycle timer 106.

Manually-actuable switches 108, 110 are also located in the vicinity of sample box 16 and responsively provide sample taken and print meter inputs signals to the microprocessor when actuated, for the purposes described hereinafter.

The microprocessor includes a central processing unit (CPU) 112, a programmable read-only memory (PROM) 114, a first random-access memory (RAM) 116, a second random-access memory (RAM) 118, a printer interface 120, a serial I/O device 122, a switch monitor 124, and an A/D converter 126. The various components of the microprocessor are interconnected by an address bus 128 and a data bus 130. Stored in PROM 114 are a set of program instructions which are executed by CPU 112 in a predetermined sequence of successive instruction cycles as determined by an internal program counter of CPU 112. Within each instruction cycle, a program instruction is first fetched by CPU 112 (through the addressing of PROM 114 via address bus 128 and the transfer of the instruction via data bus 130). In succeeding portions of the instruction cycle, the instruction is executed, either by data transfers internal to CPU 112, or by the transferring of data among CPU 112, RAMs 116, 118, printer interface 120, serial I/O device 122, switch monitor 124 and A/D converter 126 (with the address of any data location being specified by CPU 112 on address bus 128 and with the actual data being transferred via data bus 130).

In a working model of the invention, CPU 112 comprised a SC/MP 8-bit parallel microprocessor chip (available from National Semiconductor Corporation)

and was located on the same printed circuit card as RAM 118 (the card is available as the SC/MP-II CPU Application Card from National Semiconductor Corporation). For further information concerning the structure and operation of such a microprocessor, reference should be made to various publications available from National Semiconductor Corporation relating to the SC/MP, including the SC/MP Technical Description (Publication No. 420079), the SC/MP Users Manual (Publication No. 4200105), the SC/MP-II Data Sheet (Publication ISP-8A/600), and the SC/MP-II CPU Application Card Data Sheet (Publication ISP-8C/100N), each of which is incorporated herein by reference.

The weight, temperature, conductivity and moisture signals are applied to respective input of A/D converter 126, which continuously converts the analog values of the signals at its input into digital form, and stores the thus-converted signals for transfer to the remaining components of the microprocessor under control of CPU 112. Switch monitor 124 receives the record empty and record full signals from cycle timer 106, the sample taken signal from switch 108, and the print meter inputs signal from switch 110, and buffers those signals for later interrogation by CPU 112. Another input to switch monitor 124 is provided by a weightometer 132 which is preferably located in the vicinity of either conveyor 11 or conveyor 12 (FIG. 1) and which is adapted to provide an output signal (represented by a contact closure) for predetermined increment of weight passing thereover (e.g., for each 1/10 ton). The output signal from weightometer 132 is also buffered in switch monitor 124 for later interrogation by CPU 112. By monitoring the output signal from weightometer 132, the microprocessor can determine the total weight that has passed the sample box 16 in any desired time interval. Switch monitor 124 also provides buffering for the dump output signal from the microprocessor to actuating means 80, and for an alarm signal from the microprocessor to an audible alarm 134.

Serial I/O device 122 provides buffering and serial-to-parallel conversion of data obtained from a keyboard 136 (preferably comprising two 16-key keypads) and buffering and parallel-to-serial conversion of data to be transferred to a display 138 (preferably comprising ten single-digit character display units). Printer interface 120 provides necessary buffering and control functions for the transfer of data to a printer logic and lower supply 140 operatively associated with a line printer 142.

Figures 10, 11:
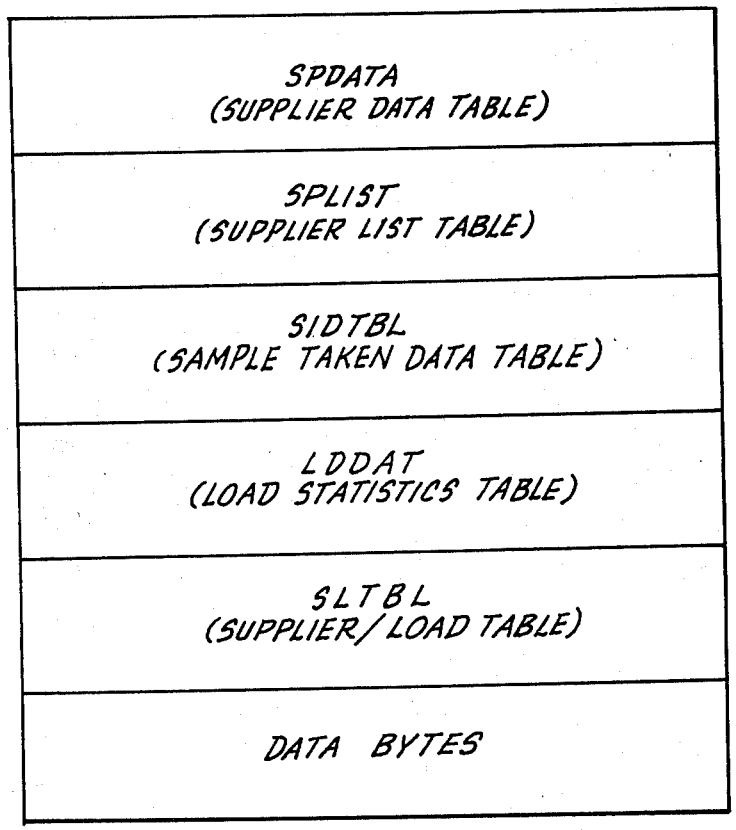
FIG. 10 is a schematic view of a keyboard illustrated in FIG. 8.
FIG. 11 is a chart illustrating the organization of a first random access memory (with a battery back-up power supply) of FIG. 8.

Keyboard 136 and display 138 are used to enter certain data and commands into the microprocessor that are necessary for the computations and other actions taken by the microprocessor, Keyboard 136 preferably includes the keys illustrated in FIG. 10, and display 138 is capable of displaying data in a number of display formats as illustrated in FIG. 30. Printer 142 conprises the principal output from the microprocessor and is controlled so as to display output data in a number of print formats as illustrated in FIGS. 31A and 31B.

In summary, the microprocessor determines the moisture percentage of each sample by determining its complement, the oven dry or fiber content percentage. In this determination, an "electronic" oven dry percentage is computed, using the value of the moisture signal from impedance measuring apparatus 100 and an empirically-determined correction factor that is related to the source of the wood chips being sampled. A "density"
oven dry percentage is also computed, using the net weight (bulk density) of the sample (as computed from the weight signal) and an empirically-determined bulk density reference. The microprocessor also performs certain tests in order to determine the best method of computing oven dry percentage for the sample. As a result of these tests, either the electronic oven dry percentage, the density oven dry percentage, or an average thereof is selected as a verified oven dry percentage by the microprocessor. If moisture in a frozen state is detected as a result of further tests by the microprocessor, the verified oven dry percentage comprises the density oven dry percentage modified by a factor $\Delta$ representing the degree of frozenness of the sample.

It has been found that wood chips from a given source or supplier tend to have the same material properties over a period of time so that a correction factor and a bulk density reference can be established for each supplier. Accordingly, the microprocessor permits the user to select and enter, through keyboard 136 and display 138, a plurality of supplier numbers, and to select and to enter a correction factor and a bulk density reference for each supplier. Further, it is desirable that the user be able to group data associated with the samples of a given shipment, or "load", so that the microprocessor also permits the user to select and enter one or more load numbers, each of which is associated with a given supplier number. The supplier numbers, load numbers, correction factors, bulk density references, and other pertinent data are stored in internal tables in the microprocessor. For each load, the microprocessor will print the supplier number and the load number of the samples currently being processed, followed by, for each sample, the measured conductivity, a computed oven dry bulk density, the verified oven dry percentage, information relating to the technique by which the verified oven dry percentage as computed, and, the wet weight of the sample (the latter being determined from the output signal from weightometer 132).

The microprocessor also computes and stores the average conductivity, the average bulk density, the average oven dry percentage, the total dry weight and the total wet weight of the load. When the user signifies (through keyboard 136) to the microprocessor that a new load is to be started, the microprocessor prints this information, and additionally stores the average oven dry percentage, the total dry weight and the total wet weight as load statistics data in an internal table for later review and printout.

During each measurement cycle, the microprocessor also performs certain tests on the data represented by the weight, conductivity and moisture signals, to determine errors therein that may be occasioned by malfunction of the mechanism associated with sample box 16, of weight sensor 88, or of impedance measuring apparatus 100. Upon the detection of any such error, the microprocessor prints out warning messages and may energize audible alarm 134 to assist the user in correcting the source of the error.

Through keyboard 136, the user may signify to the microprocessor that all oven dry percentages for a given supplier are to be computed only on the basis of density, and also may signify to the microprocessor that only the electronic or only the density oven dry percentage is to be selected for a given load.

The user may also use keyboard 136 to cause the microprocessor: to print all supplier numbers and related supplier data; to display the total current weight of the load; to print the values of the weight, temperature, conductivity and moisture signals of a sample; to erase any supplier number, and all data related to that supplier number, from the microprocessor; to print all load statistics data associated with a supplier number and to erase all such data from the microprocessor.

When switch 108 is actuated by the user, the resultant sample taken signal causes the microprocessor to store, in a table, the electronic and density oven dry percentages of the sample then being processed, and relates the thus-stored values to a given supplier number and load number combination. The microprocessor also assigns a sample ID number to the sample, and prints the sample ID number, the supplier number, the correction factor and bulk density reference for the supplier, and, for the sample that has been "taken", the value of the moisture signal, the net weight, the selected oven dry percentage, the mode of computation of the verified oven dry percentage, the value of the conductivity signal, the value of the temperature signal, and the tare weight. The user then "takes" the sample from the sample box and performs laboratory measurements thereon in order to determine an "oven test" oven dry percentage. At a later time, the user enters the sample ID number and the "oven test" oven dry percentage, whereupon the microprocessor updates the correction factor and the bulk density reference for the supplier, calculates the mean deviation of the correction factor and of the bulk density reference, and provides a printout of the sample ID number, the supplier number, and the old and new values of the correction factor, the bulk density reference, and the deviations thereof.

When the user actuates switch 110 and a print meter input signal is provided, the microprocessor prints out the values of the weight, temperature, conductivity and moisture signals of the current sample (which is the same function provided in response to the actuation of a corresponding key in keyboard 136).

Figure 12:
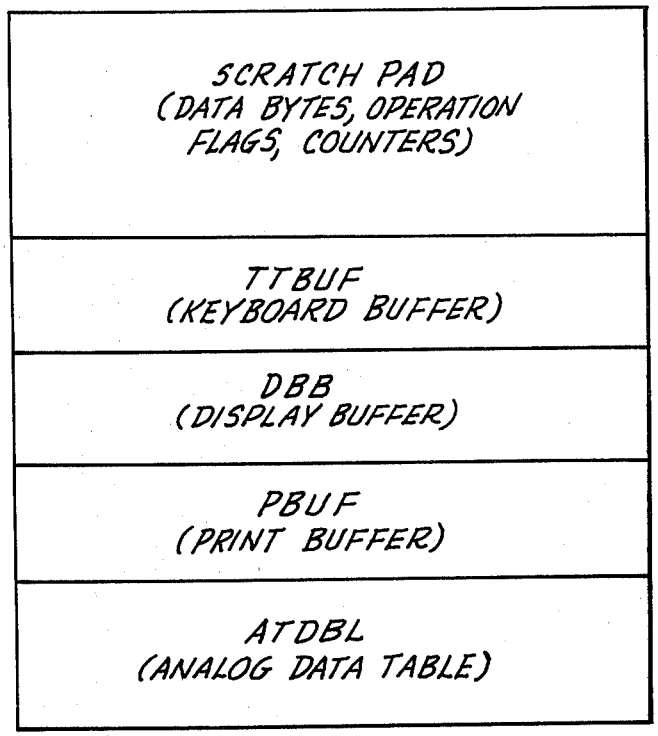
FIG. 12 is a chart illustrating the organization of a second random access memory of FIG. 8.

The set of program instructions in PROM 114 permits CPU 112 to organize the contents of RAM 116 and RAM 118 as respectively set forth in FIGS. 11 and 12. RAM 116 is additionally provided with a battery back-up power supply, so that the contents thereof are not lost upon a power outage.

With reference now to FIG. 11, RAM 116 is organized into a supplier data table SPDATA, a supplier list table SPLIST, a sample taken data table SIDTBL, a load statistics table LDDAT, a supplier/load talbe SLTBL, and a plurality of data bytes. The contents of the various tables in RAM 116 are as follows:

The plurality of supplier numbers in SPLIST are stored in order of entry, and each represents a given supplier or source of wood chips. Each supplier number in SPLIST has associated therewith a BD bit which is set if all computations of oven dry percentage for a given supplier are to be made using only bulk density. The entry of each supplier number, and the setting of each BD bit, is accomplished by the user through keyboard 136 and display 138.

The SPDATA table contains a plurality of entries of supplier-related data, with each entry being associated with a single supplier number. Each entry is made by the user through keyboard 136 and display 138.

The SLTBL table contains a plurality of supplier number/load number combinations, with each such combination being generated by the microprocessor in response to the entry of a supplier number and load number by the user through keyboard 136 and display 138.

The location of a particular supplier number is SPLIST determines a supplier code. Each sample taken data entry in SIDTBL includes a single supplier code which references the following portion of the entry to a supplier number in SPLIST. The density oven dry percentage ODW and the electronic oven dry percentage ODE in each entry in SIDTBL are the values determined during a measurement cycle when a sample taken signal is provided to the microprocessor.

The location of a particular supplier number/load number combination in SLTBL determines a S/L code, Each load-related data entry in LDDAT includes a single S/L code which references the following portion of the entry to a supplier number/load number combination in SLTBL. The average oven dry percentage AVOD, the dry weight DWT, and the wet weight WWT of each entry in LDDAT are the running values thereof for a given load number.

With additional reference now to FIG. 12, RAM 118 includes a scratchpad memory, including a plurality of data bytes, operation flags, and counters, a keyboard buffer TTBUF, a display DBB, a print buffer PBUF, and an analog data table ATDBL. TTBUF, DBB, and PBUF are temporary buffers for storage, respectively, of data received from keyboard 136 via serial I/O device 122, of data to be transferred to display 138 through serial I/O device 122, and of data to be transferred to printer 142 via printer interface 120 and printer logic and supply 140. ATDBL comprises a temporary buffer for storage of the outputs of A/D con-

TABLE I

| Table in RAM 116 | Contents |
|---|---|
| SPLIST | Plurality of entries each consisting of three-digit supplier number and BD bit (set if BULK DENSITY ONLY to be used) |
| SPDATA | For each supplier number in SPLIST, a supplier-related data entry comprising: CF (correction factor), CF sign, CF deviation, BDREF (bulk density reference), BDREF deviation |
| SLTBL | Plurality of entries each consisting of three-digit supplier number and six-digit load number; location of entry in SLTBL determines S/L (supplier/load) code |
| SIDTBL | Plurality of "sample taken" data entries each consisting of supplier code SPLCD (related to location of supplier number in SPLIST), ODW (density oven dry percentage); ODE electronic oven dry percentage); location of entry in SIDTBL determines sample ID number |
| LDDAT | Plurality of load-related data entries each consisting of S/L code, AVOD (average oven dry bulk density), DWT (total dry tons), WWT (total wet tons) | verter 126 representing the digitized values of the weight, temperature, conductivity and moisture signals.

The various data bytes and counters contained within the scratchpad memory of RAM 118 and the various data bytes within RAM 116 are as follows:

A listing of the various operation flags within the scratchpad memory of RAM 118, together with a tabulation of the conditions under which each operation flag is set and cleared, is as follows:

TABLE II

| Data Byte/Counter | Description |
|---|---|
| *WTOCNT | Running weight of load (from weightometer), in tons |
| *LWTO | WTOCNT at beginning of previous measurement cycle |
| *SWTO | WTOCNT at beginning of current measurement cycle |
| WTONS | wet weight of load current measurement cycle, in tons |
| *DTONS | Dry weight of load at current measurement cycle, in tons |
| TWT | Tare weight of sample box during current measurement cycle, in lbs/ft$^3$ |
| FWT | Full weight of sample box during current measurement cycle, in lbs/ft$^3$ |
| TCW | Net weight of current sample, in lbs/ft$^3$ |
| *BDRE | Supplier bulk-density reference, in lbs/ft$^3$ |
| *CRF | Supplier correction factor and sign, in percentage |
| *SUPL | Supplier number in display 138 |
| *CLOD | Load number in display 138 |
| *RSLCD | S/L code for supplier number and load number in display 138 |
| *SPLCD | Supplier code for supplier number in display 138 |
| ODW | Density oven dry (fiber content) percentage of current sample |
| PCM | Measured moisture percentage of current sample (based on electrical impedance) |
| ODE | Electronic oven dry (fiber content) percentage of current sample |
| DLT | Difference between ODW, ODE |
| TMP | Measured temperature of current sample, in °C. |
| CCN | Measured conductivity of current sample, in arbitrary units |
| ODV | Verified oven dry (fiber content) percentage of current sample |
| ODBD | Oven dry bulk density of current sample, in lbs/ft$^3$ |
| *AVCON | Average conductivity of load |
| *AVBD | Average oven dry bulk density of load |
| *AVOD | Average oven dry (fiber content) percentage of load |
| MODE | Flag status for printout |
| PTWT | Tare weight during previous measurement cycle |
| LWCT | Low tare weight counter |
| HICT | High tare weight counter |
| SHCT | Tare weight shift counter |
| SPLE | ODE of "sample taken" from SIDTBL (if ODE ≠ 0) |
| SPLW | ODW of "sample taken" from SIDTBL (if ODW ≠ 0) |
| OT | Oven dry (fiber content) percentage of "sample taken" by oven test |
| DELTE | Difference between OT,SPLE |
| DELTW | Difference between OT,SPLW |
| NEWCFDEV | Correction factor mean deviation computed by AUTOCF |
| NEWBDREFDEV | Bulk density reference mean deviation computed by AUTOCF |
| NEWCF | Correction factor computed by AUTOCF |
| NEWBDREF | Bulk density reference computed by AUTOCF |
| FZCT | Frozen counter |

*-in RAM 116

TABLE III

| Operation Flag | Set | Cleared |
|---|---|---|
| TWLV | MTPRO: Low Tare Wt. Limit Violation | START NEW LOAD key, or, record empty signal |
| WTLO | CLCFUL: TCW <6 lbs/ft$^3$ | START NEW LOAD key, or, record empty signal |
| RFNG | CLCFUL: BDRE <4 lbs/ft$^3$ or >/17 lbs/ft$^3$ | START NEW LOAD key, or, record empty signal |
| ODWB | CLCFUL: ODW ≧75% | START NEW LOAD key, or, record empty signal |
| ELNG | CLCFUL: PCM ≦25% or >75% | START NEW LOAD key, or, record empty signal |
| DLTA | CLCFUL: DLT positive | START NEW LOAD key, or, record empty signal |
| TFLG | CLCFUL: TMP <5° C. | START NEW LOAD key, or, record empty signal |
| CONF | CLCFUL: CCN >49 | START NEW LOAD key, or, record empty signal |
| FRZN | CLCFUL: TFLG & DLTA set | START NEW LOAD key, or, CLCFUL: FZCT = 8 |

TABLE III-continued

| Operation Flag | Set | Cleared |
|---|---|---|
| BDFLG | CLCFUL: BD bit for supplier set | START NEW LOAD key |
| MELC | ALL ELEC ONLY key | START NEW LOAD key |
| MBDO | ALL DENSITY ONLY key | START NEW LOAD |
| ODEZ | AUTOCF: ODE = 0 | AUTOCF |
| ODWZ | AUTOCF: ODW = 0 | AUTOCF |
| MTFG | Record empty signal | Record full signal, or MTPRO: Tare Wt. Violation |

Figure 13:
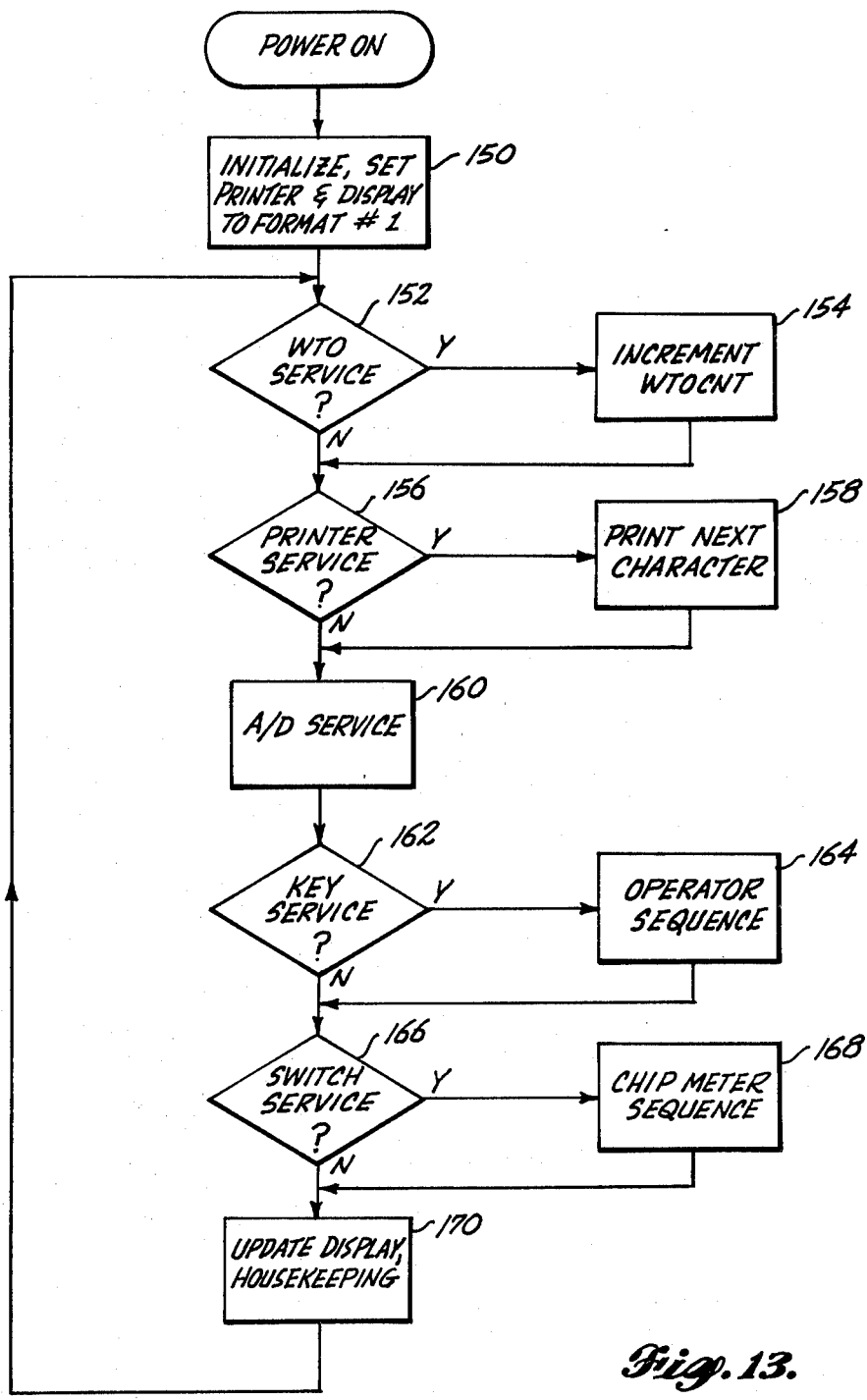
FIG. 13 is a flow chart of the program steps undertaken by the microprocessor in a main program loop thereof.
Figure 15:
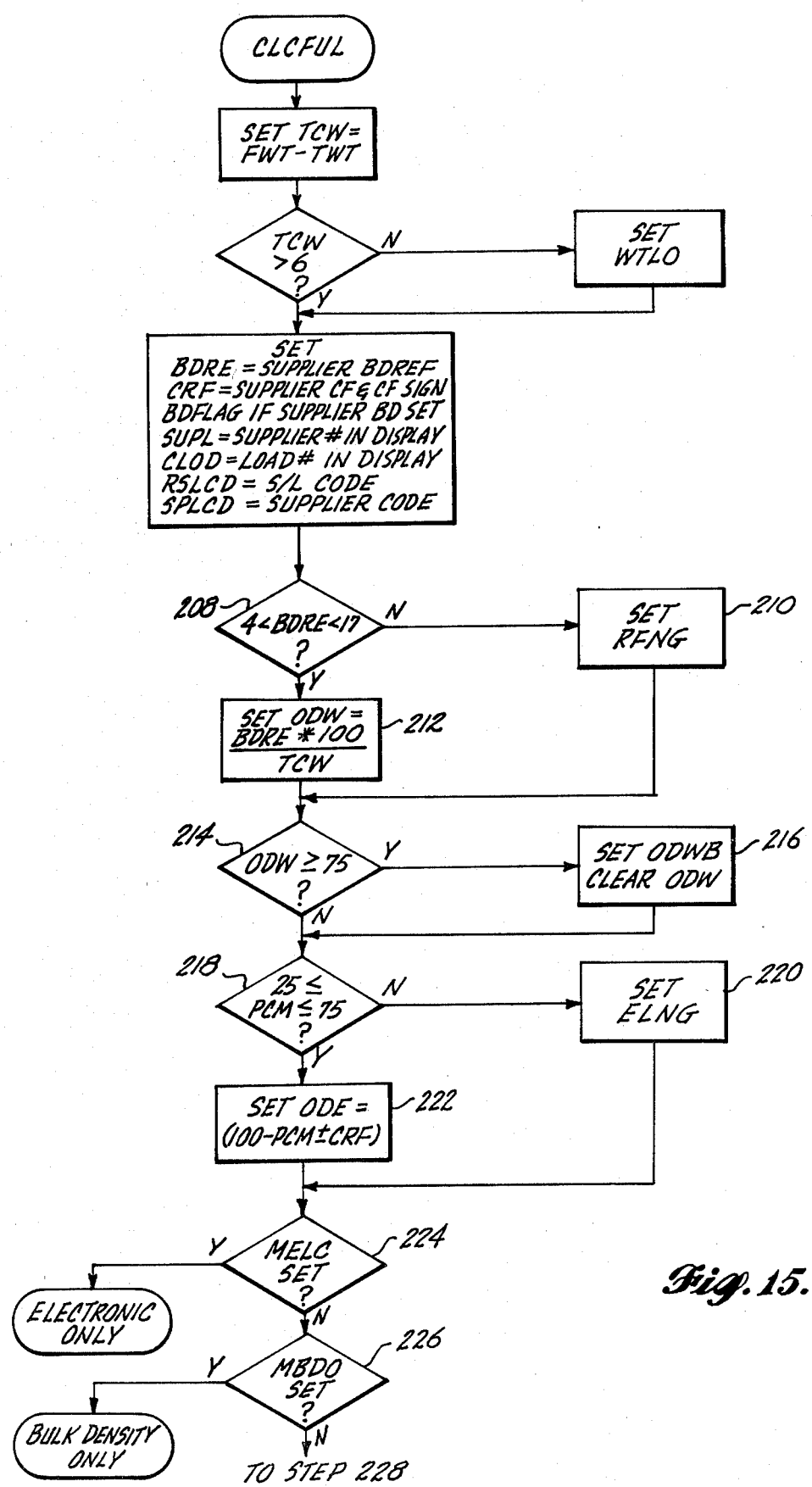
FIGS. 15, 16 and 17 are a flow chart of the program steps undertaken by the microprocessor in a CLCFUL subroutine.
Figure 16:
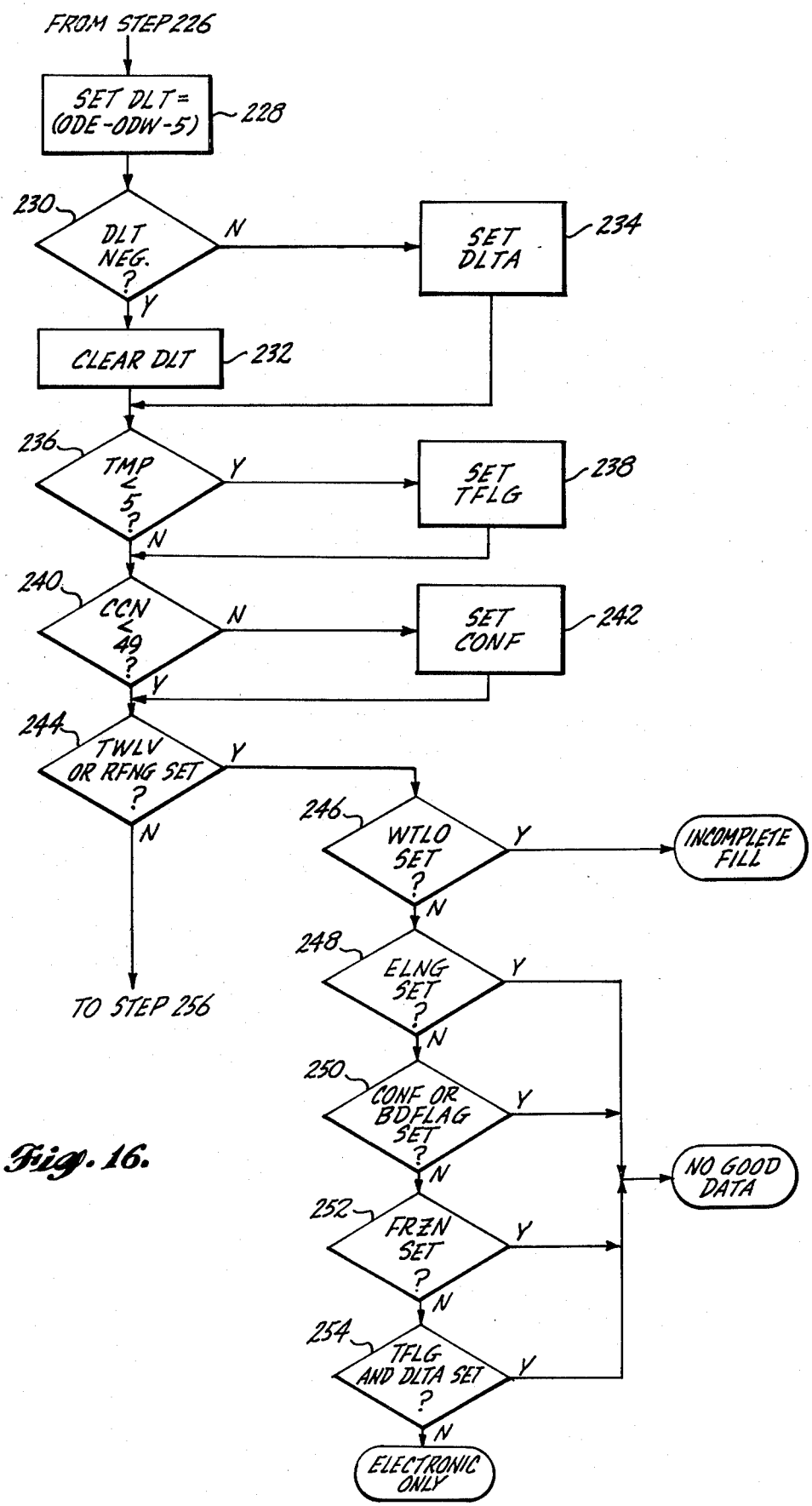
Figure 17:
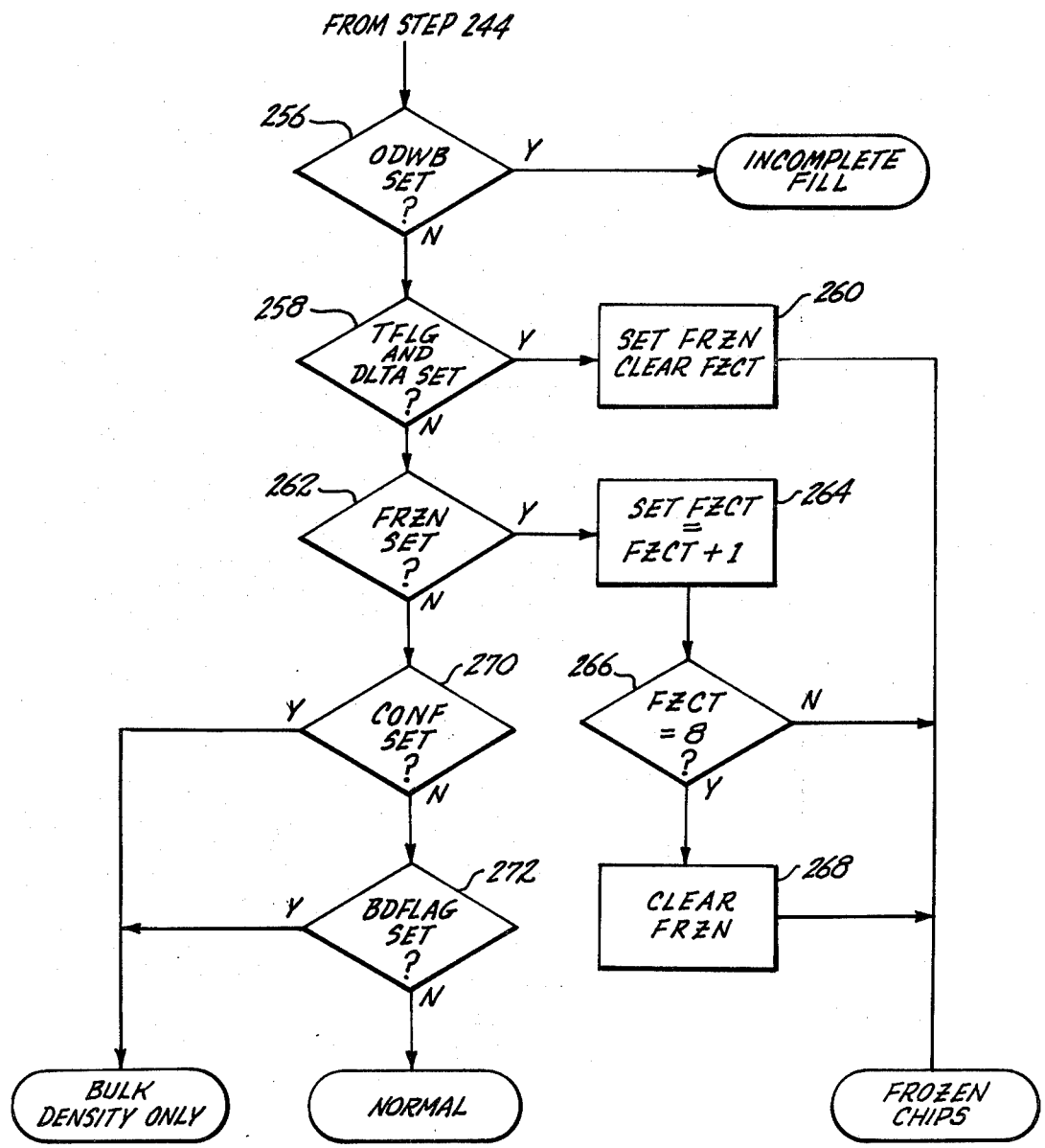

With reference now to FIG. 13, the detection of a POWER ON condition by CPU 112 results in CPU 112 entering step 150, in which certain initialization operations are performed (including the clearing of the contents of RAM 118). In addition, the display (e.g., display buffer DBB) is set to format #1 (FIG. 30) whereupon display 138 is conditioned to display a load number entry field and a supplier number entry field. If sample data was being processed at the time that power as interrupted, the load number and supplier number relating to that sample data (stored in SUPL, CLOD) will be displayed. If no sample data was being pressured, the display remains blank. A data line is formatted in the print buffer PBUF in format #1 (FIG. 31A), and a call is made for printer service.

From step 150, CPU 112 enters its main program loop and proceeds, in step 152, to determine if service of data from the weightometer 132 is required. In doing do, CPU 112 determines if switch monitor 124 has detected a signal from weightometer 132 representing, as previously described, the passage of a predetermined increment of weight over the weightometer. If the determination in step 152 is affirmative, CPU 112 increments the contents of the WTOCNT data byte by an amount related to that predetermined increment of weight. From step 154, or from step 152 if the determination therein is negative, CPU 112 proceeds, in step 156, to determine if printer service is required. In the situation being discussed, printer service was called for in step 150, whereupon the determination in step 156 is affirmative. As a result, CPU 112 proceeds, in step 158, to cause printer 142 to print a single character of the data line formatted in PBUF. Because of the relatively slow speed of printer 142, CPU 112 then exits from step 158. Upon successive passes of CPU 112 through its main program loop, successive characters in the data line formatted in PBUF are printed until the entire data line has been printed and the call for printer service is removed. When a POWER ON condition has been detected, the message contained in print format #1 will therefore be printed by printer 142 to signify to the user that a power interruption has occurred.

From step 158, or from step 156 if the determination therein is negative, CPU 112 proceeds, in step 160, to perform A/D service. During each pass through step 160, CPU 112 transfers the digital value of one input signal from A/D converter 126 to ATDBL and is conditioned to select another input signal for transfer during a succeeding pass of CPU 112 through its main program loop. From step 160, CPU 112 proceeds, in step 162, to determine if key service is required, e.g., has the actuation of any key in keyboard 136 been detected by serial I/O device 122. If the determination in step 162 is affirmative, CPU 112 proceeds, in step 164, to execute an operator sequence which is related to the key that has been actuated. A listing of the various keys (see FIG. 10) and their associated operator sequences is as follows:

TABLE IV

| Key | Operator Sequence |
|---|---|
| SUPL # | Set display to format #1, recognize subsequent number as supplier number, display in supplier entry field (FIG. 30) |
| LOAD # | Set display to format #1, recognize subsequent number as load number, display in load entry field (FIG. 30) |
| CORR FACTOR | If display in formats #1 or #2, set display to format #2, transfer supplier number to supplier number field, recognize subsequent number as correction factor, display in correction factor entry field (FIG. 30) |
| (−) | If display in format #2, display "—" in CF sign field (FIG. 30) |
| BULK DENSITY REF | If display in formats #1 or #2, set display to format #2, transfer supplier number to supplier number field, recognize subsequent number as bulk density reference display in bulk density reference field (FIG. 30) |
| CALC USING DENS | If display in format #2, set flag to indicate that BD bit for supplier is to be set |
| STORE SUPL DATA | If display in format #2, transfer supplier number, and, correction factor, CF sign, and bulk density reference from display to SPLIST and SPDATA; respectively; set BD bit in SPLIST if flag set; set printer to formats #3 and #4 (FIG. 31B), format data lines in PBUF and call for printer service |
| START NEW LOAD | Display must be in format #1 and supplier number in display must be in SPLIST (otherwise set printer to format #34 (FIG. 31B), format data line in PBUF and call for printer service): for previous load (if any), store AVOD, DWT, WWT in |

TABLE IV-continued

| Key | Operator Sequence |
|---|---|
| | LDDAT, set printer to formats #7–#11 (FIG. 31A), format data lines in PBUF from RAM 116, RAM 118, and call for printer service; for new load, see if supplier number and load number in SLTBL and store same if not to assign S/L code; set printer to formats #2-5 (FIG. 31A), format data lines in PBUF from display and SPDATA, and call for printer service; clear all data bytes and counters (Table II) and certain operation flags (Table III) |
| ERASE SUPL # | If display in format #2, erase all data associated with supplier number in display from SPLIST and SPDATA, set printer to formats #3, 4 and 40 (FIG. 31B), format data lines in PBUF and call for printer service |
| PRINT LOAD DATA | For each supplier number/load number combination in SLTBL, set printer to formats #42, 9, 10 (FIG. 31B), format data lines in PBUF from LDDAT, call for printer service |
| ERASE LOAD DATA | If PRINT LOAD DATA key has been actuated, erase LDDAT |
| PRINT ALL SUPL # | For each supplier number in SPLIST, set printer to formats #3 and 4 (FIG. 31B), format data lines, in PBUF from SPLIST & SPDATA, call for printer service |
| PRINT METER INPUTS | Set printer to formats #25 and 26 (FIG. 31A), format data lines in PBUF from ATDBL, call for printer service |
| DISPLAY WEIGHT | Set display to format #4 (FIG. 30), display WTOCNT and AVOD from RAM 116 |
| ALL ELEC ONLY | Set MELC, set printer to format #23 (FIG. 31A), format data line in PBUF, call for printer service |
| ALL DENS ONLY | Set MBDO, set printer to format #24 (FIG. 31A), format data line in PBUF, call for printer service |
| SAMPLE ID # | Call AUTOCF (FIGS. 26-29) |
| OVEN TEST RESULT | See AUTOCF |
| STORE TEST RESULT | See AUTOCF |

From step 164, or from step 162 if the determination therein is negative, CPU 112 proceeds, in step 166, to determine if switch service is required, e.g., has the switch monitor 124 detected a signal at any of its inputs. If the determination in step 166 is affirmative, CPU 112 proceeds in step 168 to execute one or more chip meter sequences related to the signal that has been detected. The chip meter sequence executed in response to a signal from weightometer 132 has already been described (see step 154). The chip meter sequences that are executed in response to the record empty and record full signals from cycle timer 106 are set forth in FIGS. 14-25 are described hereinafter; the chip meter sequence that is executed in response to the sample taken signal is set forth in FIG. 25A and described hereinafter; and, the chip meter sequence that is executed in response to the print meter inputs signal is identical to the operator sequence executed in response to actuation of the print meter inputs key in keyboard 136 (see Table IV). In each chip meter sequence, a call is made for printer service and appropriate data is transferred to printer 142 for printout upon subsequent passes of CPU 112 through its main program loop.

From step 168, or from step 166 if the determination therein is negative, CPU 112 proceeds, in step 170, to update the display (e.g., to transfer any data in the display buffer DBB to display 138), and also perform certain housekeeping functions. From step 170, CPU 112 return to step 152 and thereafter passes again through its main program loop.

With reference now back to FIG. 10 and Table IV, let it be assumed that the user desires to enter supplier-related data into the microprocessor. The user accordingly actuates the SUPL # key. As a result, a number subsequently entered by the user through the number keys in keyboard 136 is displayed in the supplier entry field of display 138 (format #1, FIG. 30). If the SPLIST table is full (e.g., all supplier numbers have been used, CPU 112 formats a data line in print buffer PBUF (format #39, FIG. 31B), and calls for printer service, whereupon the user is informed that the table is full. If the SPLIST table is not full, the user then actuates either the CORR FACTOR key or the BULK DENSITY REFERENCE key. As a result, CPU 112 sets the display to format #2 (FIG. 30) and displays the supplier number in a different field. If the CORR FACTOR key has been actuated, a number subsequently entered by the user (and a "—" if the user has also actuated the minus sign key) are recognized as the correction factor (and its sign) and displayed in the appropriate fields of the display. If the BULK DENSITY REF key has been actuated, the subsequently-entered number is recognized as the bulk density reference and displayed in the appropriate field of the display. If the display is in format #2, the user may also actuate the CALC USING DENSITY key, whereupon a flag is set to signify that only a "density" oven dry percentage is to be computed for the supplier. If the user fails to properly enter a supplier number before actuating any of the CORR FACTOR or BULK DENSITY REF keys, CPU 112 formats a data line in the print buffer PBUF (format #38, FIG. 31B), and calls for printer service, so that the user is informed that the key actuation has been out of order.

When the user actuates the STORE SUPL DATA key, the displayed supplier number is stored in SPLIST and the associated BD bit therein is set if the corresponding flag has been set. Further, any displayed correction factor, correction factor sign, or bulk density reference is stored in SPDATA. CPU 112 then sets the printer to formats #3 and #4 (FIG. 31B), formats the data lines, and calls for printer service.

In order to identify a load, the user actuates the SUPL # key, enters the supplier number, then actuates the LOAD # key and enters a load number. As a result, the display is in format #1 and displays the thus-entered supplier number and load number. At the time that processing of sample data for the thus-displayed load is to commence, the user actuates the START NEW LOAD key. If the display is in format #1 and contains a supplier number and a load number, and if the thus-displayed supplier number is found in SPLIST, CPU 112 determines if the supplier number/load number combination is found in the SLTBL table. If not, the supplier number/load number combination is stored therein, with the location of the supplier number/load number combination determining the S/L code.

If CPU 112 has been processing sampe data for a previous load at the time that the START NEW LOAD key is actuated, the contents of various data bytes (AVOD, DWT, WWT) determined for the previous load are stored in the LDDAT table at a location determined by the S/L code. In addition, the printer is set to formats #7-11 (FIG. 31A), the appropriate data lines are formatted and a call is made for printer service, whereupon a summary message for the load is printed. Subsequent to this step, the printer is set to formats 2-5 (FIG. 31A), the appropriate data lines are formatted, and a call is made for printer service, whereupon a header message relating to the new load is printed. As described hereinafter, the microprocessor thereafter prints (in print format #6) the sample data listed in print format #5 for each subsequent sample of the load as that sample data is processed during successive measurement cycles.

Further, upon actuation of the START NEW LOAD key, all data bytes (reference Table II) and certain operation flags (reference Table III) are cleared.

During the processing of sample data for a load, the user may decide that all further computations of oven dry percentage are to be "electronic" or "density" only. Accordingly, when the user actuates the ALL ELEC ONLY key, the MELC operation flag is set, the printer is set to format #23 (FIG. 31A), a data line is formatted, and a call is made for printer service, whereupon the user is informed that the printout of oven dry percentage for subsequent samples of the load represents the electronic oven dry percentage only. A similar operation takes place when the ALL DENS ONLY key is actuated, whereupon the MBDO operation flag is set, the printer is set to format #24 (FIG. 31A), a data line is formatted and a call is made for printer service.

By the foregoing actions, the microprocessor has stored therein the data and commands necessary to process the sample data. The actual data processing takes place in the chip meter sequences (step 168 in FIG. 13) in response to the detection of signals by switch monitor 124.

Figure 14:
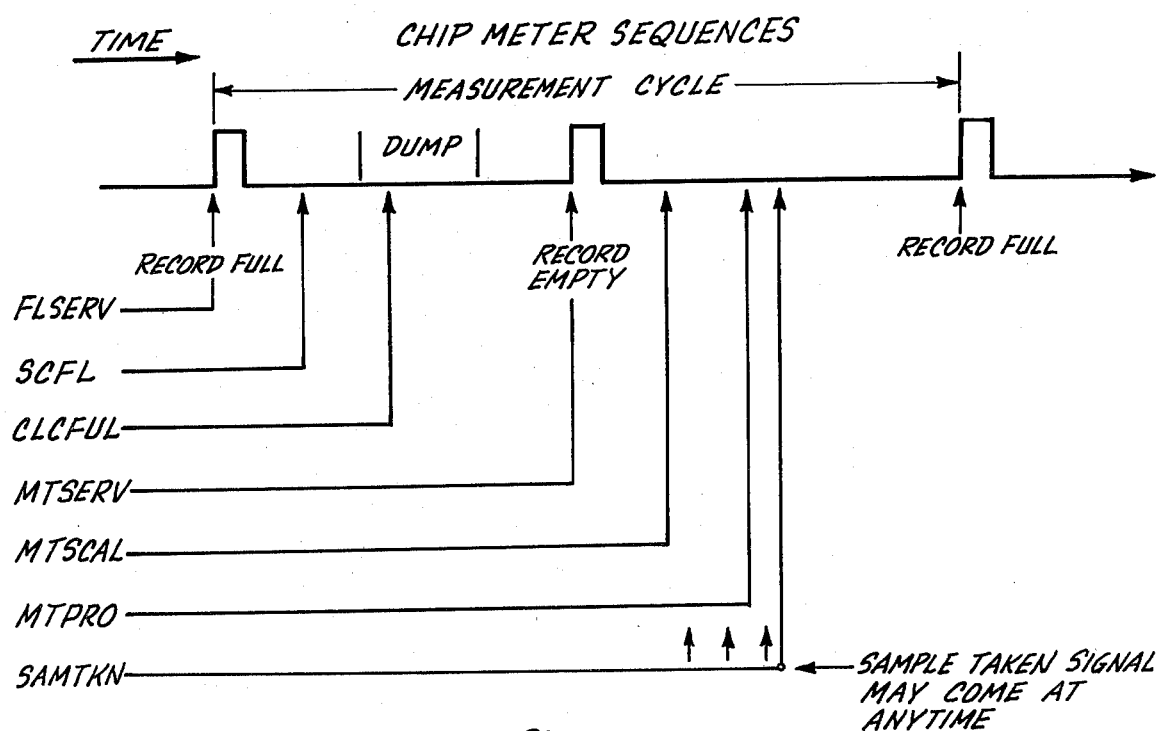
FIG. 14 is a diagram illustrating the timing of various "chip meter sequences" undertaken by the microprocessor.

With reference now to FIG. 14, the timing of the various chip meter sequences during each measurement cycle is illustrated. Upon provision of a record empty signal by cycle timer 106 during a previous measurement cycle, sample box 16 has been filled with a sample of wood chips. In response to the record full signal, CPU 112 clears the WTLO, RFNG, ODWB, ELNG, DLTA, TFLG, CONF, and MTFG operation flags (see Table III) and executes a FLSERV subroutine (not illustrated), wherein the data within ATDBL (representing the full weight, temperature, conductivity and moisture of the sample) is stored in certain temporary data bytes (not illustrated) in RAM 118. Thereafter, CPU 112 executes a SCFL subroutine (not illustrated), in which the thus-stored data is scaled to a predetermined range (temperature 0°–50° C.; weight: 1–40 lb/ft$^3$; conductivity: 0–50; moisture: 25–75%). During this scaling operation, any data that is outside its predetermined range is set to the nearest range limit (e.g., a minus temperature is set to 0° C.) and linearity of the data is maintained within the range. The scaled temperature, full weight, conductivity and moisture data are then stored in TMP, FWT, CCN, and PCM (see table II). Thereafter, CPU 112 executes a CLCFUL subroutine (FIGS. 15–17), and its associated subroutines (FIGS. 18–24), in which computations relating to the sample are made and certain information is made ready for printing.

Figure 25:
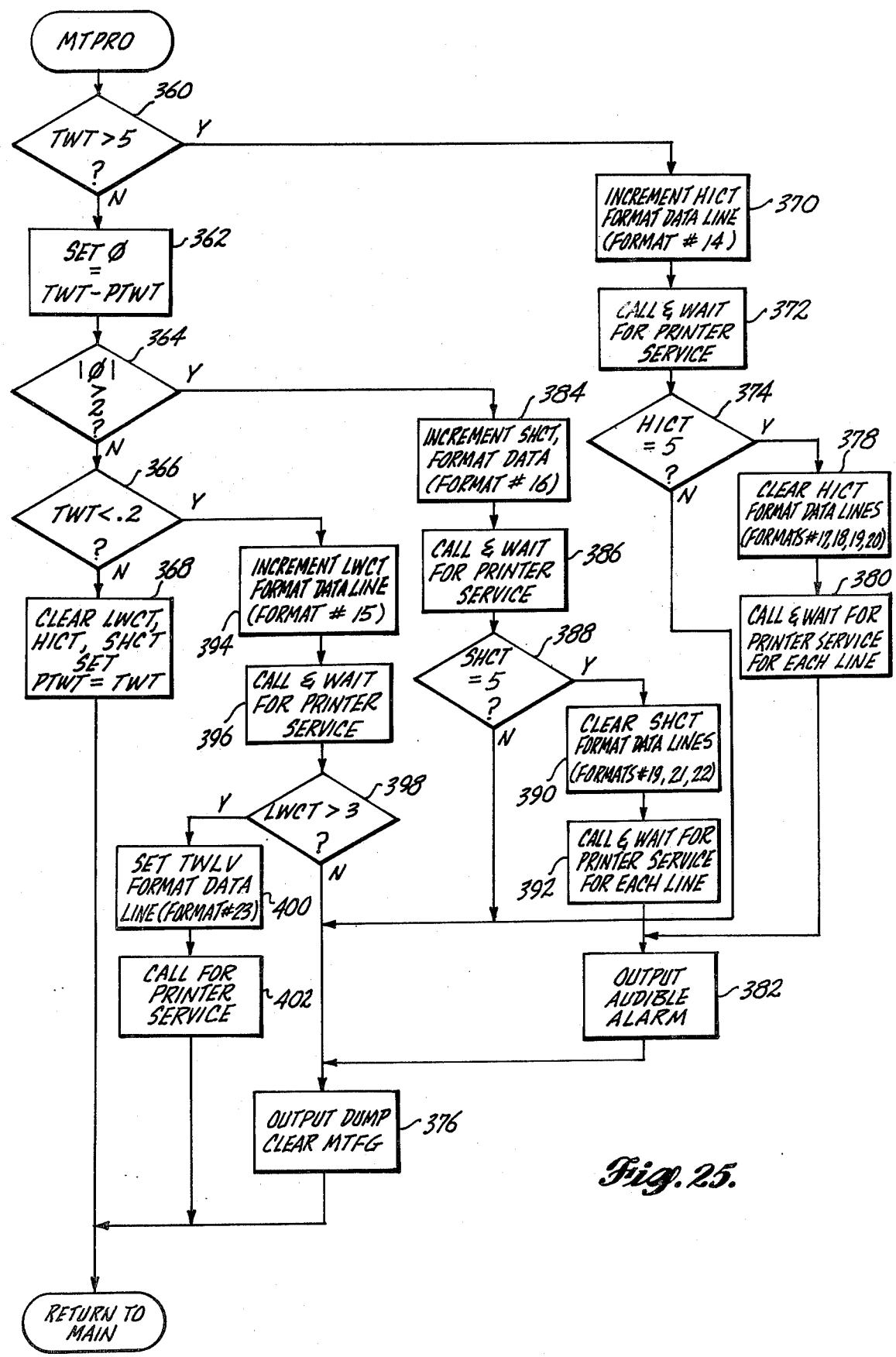
FIG. 25 is a flow chart of the program steps undertaken by the microprocessor in a MTPRO subroutine.

At some time after the record full signal, CPU 112 causes a dump output signal to be provided for a short period of time to actuating means 80 (provided that a tare weight violation has not been detected as described hereinafter), whereupon the sample is discharged from sample box 16. Subsequent thereto, cycle timer 106 provides a record empty signal, whereupon CPU 112 successively executes a MTSERV subroutine (not illustrated), a MTSCAL subroutine (not illustrated), and a MTPRO subroutine (FIG. 25). During the MTSERV subroutine, data in ATDBL representing the empty or tare weight of sample box 16 is stored in a temporary data byte (not illustrated) in RAM 118. During the MTSCAL subroutine, the thus-stored data is scaled (similar to the operation undertaken in SCFL), and the scaled data is stored in TWT (see Table II). During the MTPRO subroutine, CPU 112 conducts certain tests on TWT to determine if the tare weight is outside predetermined limits or if a shift has occurred in the tare weight. Upon determination of a tare weight limit violation or tare weight shift, certain warning messages are entered into the print buffer and a call is made for printer service. Further, CPU 112 causes a dump output signal to be provided to actuating means 80, whereupon the contents of the sample box for the next sample are discharged, and also clears a flag (MTFG) to inhibit computations of sample data during succeeding measurement cycles until the cuase of the tare weight limit violation or tare weight shift has been found and corrected. If a low tare weight violation persists for a predetermined number of successive measurement cycles, a flat (TWLV) is also set so that computations of sample data for succeeding measurement cycles are made using only the electronic oven dry percentage.

Subsequent to executing the MTPRO subroutine, CPU 112 executes the SAMTKN subroutine if switch 108 has been actuated by the user and a sample taken signal has been provided at any time during the current measurement cycle. During the SAMTKN subroutine (FIG. 25A), CPU 112 makes certain determinations as to the validity of the sample data obtained during the measurement cycle, and, if valid, stores certain data relating to the "sample taken" in the SIDTBL table and formats certain data for printout.

In the CLCFUL subroutine (FIGS. 15–17) and its associated subroutines (FIGS. 18–24), the microprocessor computes the density oven dry percentage and the electronic oven dry percentage, using input data obtained from ATDBL and supplier-related data obtained from SPDATA.

The density oven dry percentage is computed according to the relationship.

density oven dry percentage =
(supplier's bulk density reference/measured bulk density of sample)*100

The supplier's bulk density reference is substantially equal to an average oven dry bulk density of wood chips from the supplier, as determined by oven testing as described hereinafter. It has been found that, for a given supplier, the oven dry bulk density determined by oven testing is substantially constant. The density oven dry percentage is thus proportional to the ratio of the nominal "dry" bulk density of the sample to its measured "wet" bulk density.

The electronic oven dry percentage is computed according to the relationship electronic oven dry percentage =
(100 − moisture percentage based on electrical impedance of sample ± supplier's correction factor)

As explained hereinafter, the supplier's correction factor (and sign) is chosen so that the average of the electronic oven dry percentages obtained for a number of samples of wood chips from a supplier is equal to an average oven dry percentage of wood chips from that supplier as determined by oven testing.

If both the density and electronic oven dry percentages are based on valid input data and are otherwise not disqualified (e.g., the user has not indicated that all computations of oven dry percentage for a supplier are to be made on the basis of density only, or, the user has not instructed the microrprocessor to select either of the oven dry percentages), tests are made to determine if the sample contains frozen moisture. If these tests are negative, the microprocessor computes an average of the density and electronic oven dry percentages in order to reduce normal instrument scatter.

If one of the density and electronic oven dry percentages is based on invalid data or has been disqualified, the microprocessor selects the other oven dry percentage if the other oven dry percentage is based on valid data and has not been disqualified. If both oven dry percentages are invalid, no determination of oven dry percentage is made for the sample and appropriate warning messages are provided to the user.

In the preferred embodiment, the microprocessor uses two tests to detect frozen moisture in the sample, both of which must be satisfied. First, the measured temperature of the sample must be below 5° C. Second, the electronic oven dry percentage must be greater than the density oven dry percentage by a predetermined amount, e.g., 5%. This amount is greater than the normal variation between those percentages due to instrument scatter.

If frozen moisture has been detected in a sample, it is likely that successive samples will also be frozen, even though either of the two tests mentioned above may not be met for one or more of the successive samples. Accordingly, when frozen moisture has been detected in any sample, a predetermined number of successive samples (e.g., eight) are also considered to be frozen.

After the microprocessor has determined that the sample contains frozen moisture, the microprocessor must determine how frozen the sample is in order to compute the oven dry percentage thereof.

Figure 9:
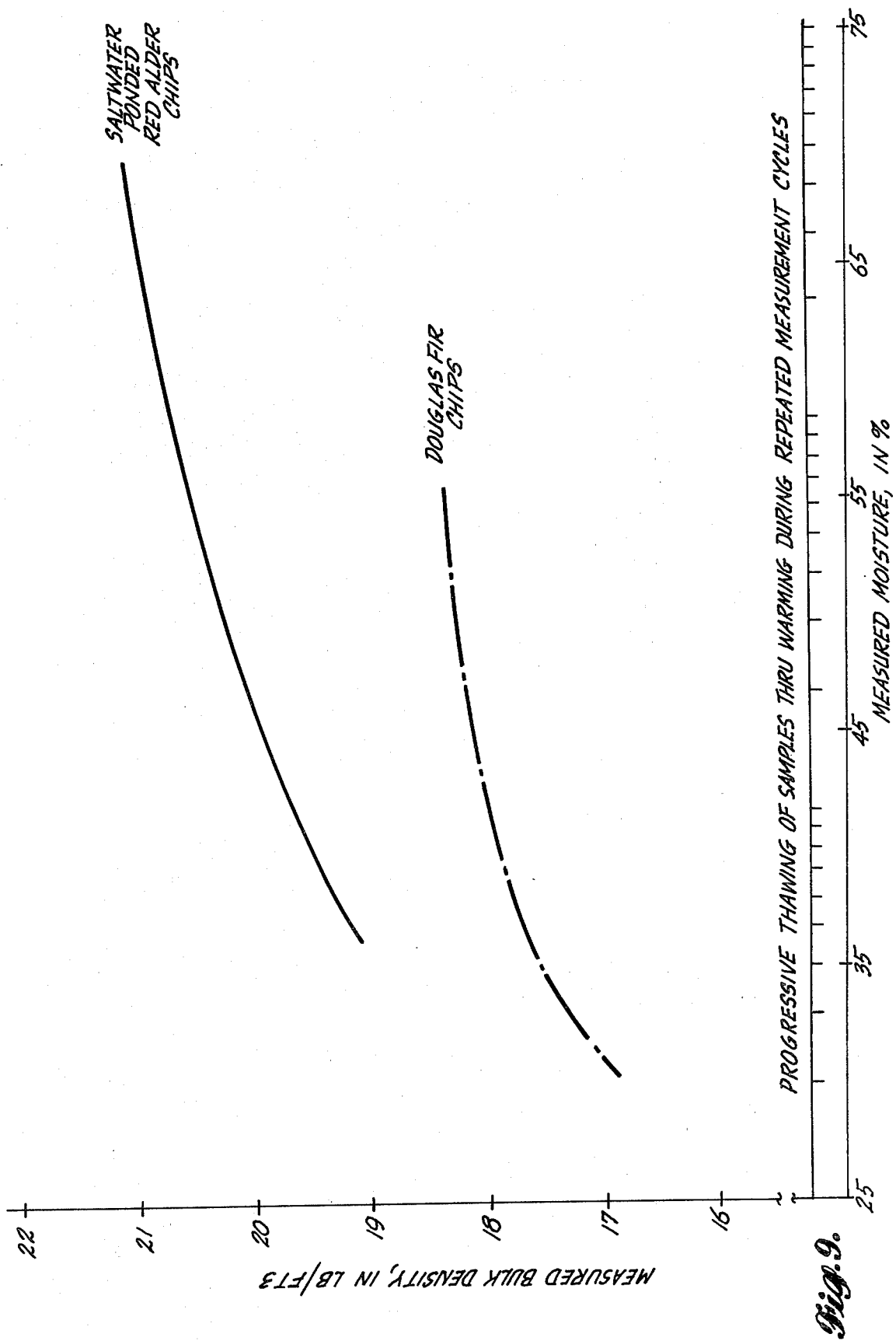
FIG. 9 is a graph illustrating the changes in measured moisture (e.g., dielectric coefficient) and measured bulk density of a sample upon progressive thawing of the sample.

With reference now to FIG. 9, the graph therein illustrates an experimentally-obtained relationship between measured moisture (e.g., the dielectric coefficient signal from impedance measuring apparatus 100) and measured bulk density (e.g., that determined from the weight signal obtained from weight sensor 88) of a plurality of samples with progressive thawing of those samples during repeated measurement cycles. The full line curve represents the relationship obtained for salt water ponded red alder chips (having a fairly high moisture content) and the dashed line curve represents the relationship obtained for douglas fir chips (having a lower moisture content). As can be seen, the measured moisture and the measured bulk density each decrease as the samples become more frozen. The decrease in measured bulk density is due to a number of factors. For example, frozen chips tend to be less free than unfrozen chips and are typically bonded together by surfce ice to form large clumps. As the surface ice melts, the clumps are broken up with a corresponding increase in the mobility of the individual chips and a corresponding increase in the bulk density of the sample. The surface ice itself together with other frozen moisture (e.g., snow) also separates the individual chips or clumps. Finally, moisture within the chips expands as it freezes. The decrease in bulk density from completely unfrozen to completely frozen chips can be seen to be on the order of 6%.

From FIG. 9, it can also be seen that the measured moisture appreciably decreases as the chips in the samples become frozen. For example, the measured moisture of the douglas fir chips decreases from approximately 55% to approximately 25%. The actual moisture of the samples, however, does not appreciably change.

Because of the foregoing, it is desirable to determine actual moisture on the basis of bulk density when a sample is frozen. Because the measured bulk density changes as the sample becomes frozen, a determination must be made as to how frozen the sample is. A degree of frozenness factor is determined as a function of moisture based on bulk density and moisture based on electrical impedance. Preferably, the degree of frozenness factor is determined according to a linear function of the difference between moisture based on bulk density and moisture based on electrical impedance. The measured bulk density is then modified by the degree of frozenness factor in order to determine the actual moisture of the sample.

In a preferred embodiment, the actual moisture of the sample is determined according to the relationship actual moisture percentage =
    moisture percentage based on bulk density + kM, where:
  moisture percentage based on bulk density = 100 − 100* (oven dry bulk density/measured bulk density),
  kM = degree of frozenness factor,
  k = a scaling constant, and
  M = (moisture percentage based on bulk density) - (moisture percentage based on electrical impedance).

The scaling constant k has been found to be substantially the same, notwithstanding the type of source of wood chips, and preferably equals 0.25.

In fact, the microprocessor implements the complemennt of the foregoing relationship by determining a verified oven dry percentage according to the relationship verified oven dry percentage = density oven dry percentage $- k \Delta$ where:
 $k\Delta$ = degree of frozeness factor
 $k = 0.25$,
 $\Delta$ = elctronic oven dry percentage − density oven dry percentage − m, and
 m = a constant equal to or greater than the normal variation between the electronic and density oven dry percentages when frozen moisture is not present, e.g., 5%.

With reference now to the CLCFUL subroutine (FIGS. 15–17), CPU 112, in step 200, determines the net weight (bulk density) of the sample by setting $TCW = FWT - TWT$ (where TWT is the value obtained during the preceding measurement cycle). CPU 112 next determines, in step 202, if the thus-determined net weight is greater than a predetermined value, e.g., is TCW > 6 lbs/ft$^3$. At this point, it should be noted that "weight" computations by CPU 112 are done in terms of bulk density, with bulk density being directly related to weight since sample box 16 has a constant volume. If the determination in step 202 is negative, sample box 16 most likely has been incompletely filled, whereupon CPU 112, in step 204, sets the WTLO operation flag.

From step 204, or from step 202 if the determination therein is affirmative, CPU 112 proceeds, in step 206, to transfer certain data from the tables in RAM 116 and from display 138 to RAM 118. Specifically, CPU 112 sets SUPL equal to the supplier number in the display, sets CLOD equal to the load number in the display, sets BDRE equal to the supplier's bulk density reference in SPDATA, sets CRF equal to the supplier's correction factor and correction factor sign in SPDATA, sets BDFLAG if the supplier's BD bit in SPLIST has been set, sets RSLCD equal to the S/L code (determined from the supplier number/load number combination in SLTBL), and sets SPLCD equal to the supplier code (determined from the location of the supplier number in SPLIST).

From 206, CPU 112 proceeds, in step 208, to determine if BDRE is within a certain range, e.g., is BDRE greater than 4 lbs/ft$^3$ and less than 17 lbs/ft$^3$. If the determination in step 208 is negative, the supplier's bulk density reference (the average oven dry bulk density for the supplier) is invalid (since wood chips typically have a bulk density in this range). As a result, CPU 112, in step 210, sets the RFNG operation flag. If the determination in step 208 is affirmative, CPU 112 next proceeds, in step 212, to compute the density oven dry percentage ODW by dividing the supplier's bulk density reference by the net weight of the sample and multiplying the resultant quotient by 100.

From either step 210 or step 212, CPU 112 proceeds, in step 214, to determine if ODW is greater than or equal to a predetermined maximum limit thereof, e.g., 75%. If CPU 112 has proceeded to step 214 through step 210, or, if ODW is less than the maximum limit thereof, the determination in step 214 is negative. However, if the determination in step 214 is affirmative, sample box 16 most likely has not been completely filled, whereupon CPU 112, in step 216, sets the ODWB operation flag and clears ODW.

From step 216, or from step 214 if the determination therein is negative, CPU 112 next determines, in step 218, if the moisture percentage based on electrical impedance PCM is within a certain range. If the determination in step 218 is negative, the moisture percentage is necessarily outside this range and the measured moisture is invalid. As a result, CPU 112, in step 220, sets the ELNG operation flag. If the determination in step 218 is affirmative, CPU 112 next proceeds, in step 222, to compute the electronic oven dry percentage ODE by setting $ODE = 100 - PCM \pm CRF$, where the sign associated with CRF is that associated with the supplier and obtained from SPDATA as previously described.

From either step 210 or step 222, CPU 112 proceeds, in step 224, to determine if the MELC operation flag has been set. Typically, the user will actuate the ALL ELEC ONLY key in the situation where repeated measurements of the density oven dry percentage have proved to be invalid, or where it is desired to compute a correction factor for the supplier as described hereinafter. If the determination in step 224 is affirmative, CPU 112 proceeds directly to an ELECTRONIC ONLY subroutine (FIG. 19). If the determination in step 224 is negative, CPU 112 next determines, in step 226, if the MBDO operation flag has been set. Typically, the user will actuate the ALL DENS ONLY key in the situation where repeated measurements of the electronic oven dry percentage have proved to be invalid, or where it is desired to compute a bulk density reference to the supplier as described hereinafter. If the determination in step 226 is affirmative, CPU 112 proceeds directly to a BULK DENSITY ONLY subroutine (FIG. 20).

If the determinations in steps 224 and 226 are each negative, CPU 112 proceeds, in steps 228–238, to determine if the sample contains frozen moisture, and, if so, to determine how frozen the sample is. In step 228, CPU 112 sets $DLT = (ODE - ODW - 5)$. Assuming that the values of the supplier's correction factor and bulk density reference have been correctly chosen, it has been found that the normal deviation between the values of the electronic and density oven dry percentages due to instrument scatter is about 2½% when the sample does not contain any frozen moisture. In addition, it has been found that when there is frozen moisture, the electronic oven dry percentage is greater than the density oven dry percentage (the inverse of the relationships illustrated in FIG. 9). The constant or factor "5" utilized in step 228 accordingly is used to insure that a frozen condition is not determined for normal variation between the electronic and density oven dry percentages.

From step 228, CPU 112 proceeds, in step 230, to determine if DLT is a negative number. If the determination in step 230 is affirmative, the sample is not frozen, whereupon CPU 112, in step 232, clears DLT. If the determination in step 230 is negative, the sample may be frozen, whereupon CPU 112, in step 234, sets the DLTA operation flag.

From either step 232 or step 234, CPU 112 determines, in step 236, if the measured temperature of the sample is less than 5° C. It has been found that when the measured temperature of the sample is greater than 5° C., the sample most likely does not contain any frozen wood chips. If the determination in step 236 is affirmative, CPU 112 sets the TFLG operation flag in step 238. As will be explained hereinafter, the setting of both DLTA and TFLG is used to indicate the presence of frozen moisture in the sample.

From step 238, or from step 236 if the determination therein is negative, CPU 112 proceeds, in step 240, to determine if the measured conductivity of the sample is less than its maximum value, e.g., 49. If the determination in step 240 is negative, the measured conductivity is invalid and CPU 112 sets the CONF operation flag in step 242.

From step 242, or from step 240 if the determination therein is affirmative, CPU 112 next determines, in step 244, if TWLV or RFNG have been set. As previously explained, TWLV is set during MTPRO when a low tare weight violation has persisted for a predetermined number of successive measurement cycles and RFNG is set if the supplier's bulk density reference is outside a certain range. In either case, the density oven dry percentage is invalid, and all further computations for the sample must be based on the electronic oven dry percentage, provided that certain additional conditions are met.

Figure 23:
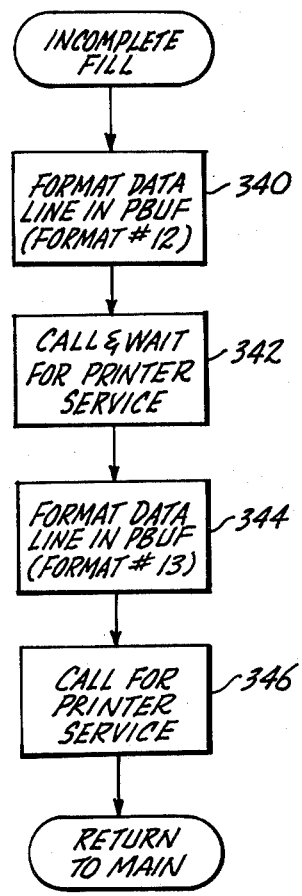
FIG. 23 is a flow chart of the program steps undertaken by the microprocessor in an INCOMPLETE FILL subroutine.
Figure 24:
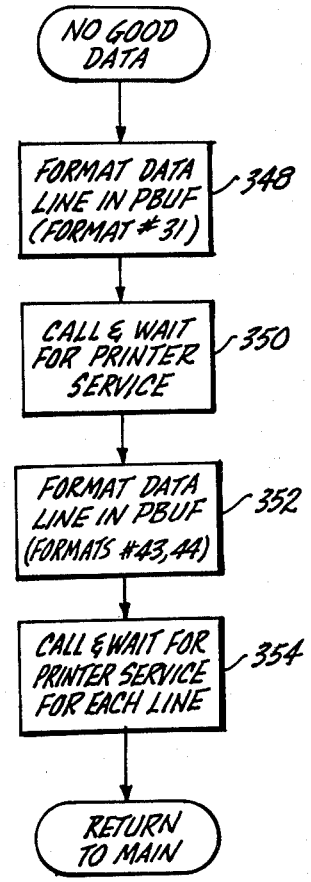
FIG. 24 is a flow chart of the program steps undertaken by the microprocessor in a NO GOOD DATA subroutine.
Figure 25A:
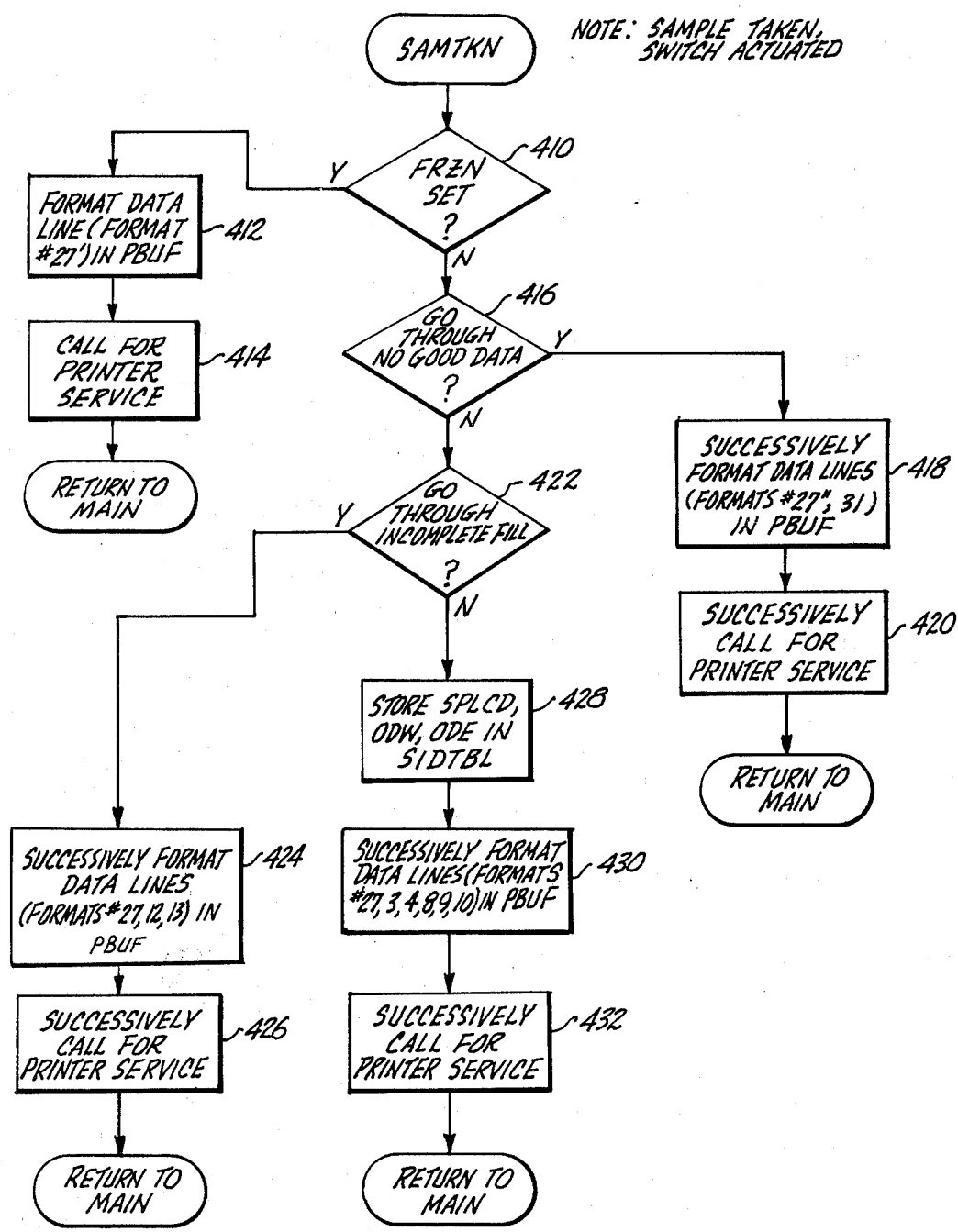
FIG. 25A is a flow chart of the program steps undertaken by the microprocessor in a SAMTKN subroutine.
Figure 26:
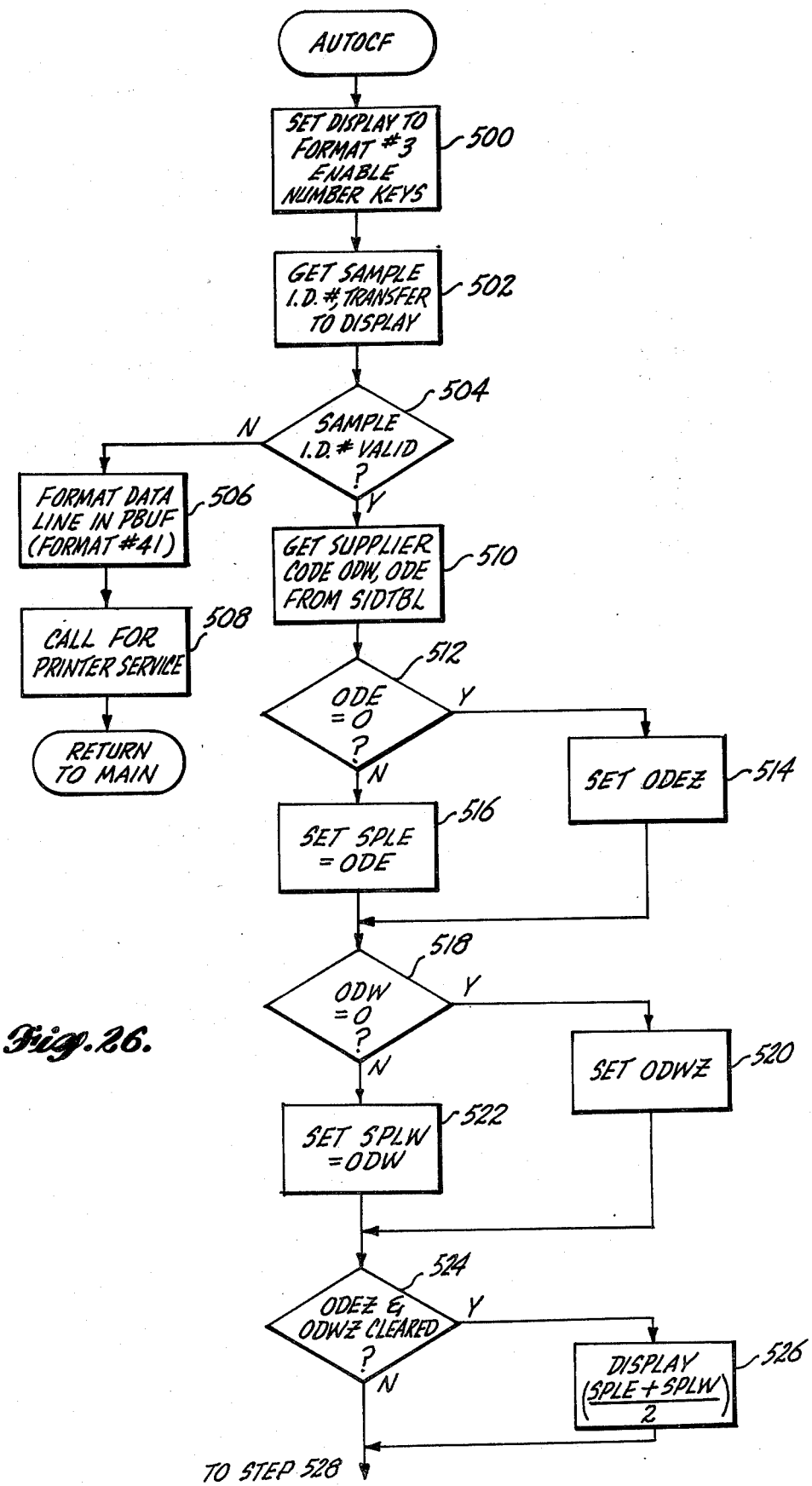
Figure 27:
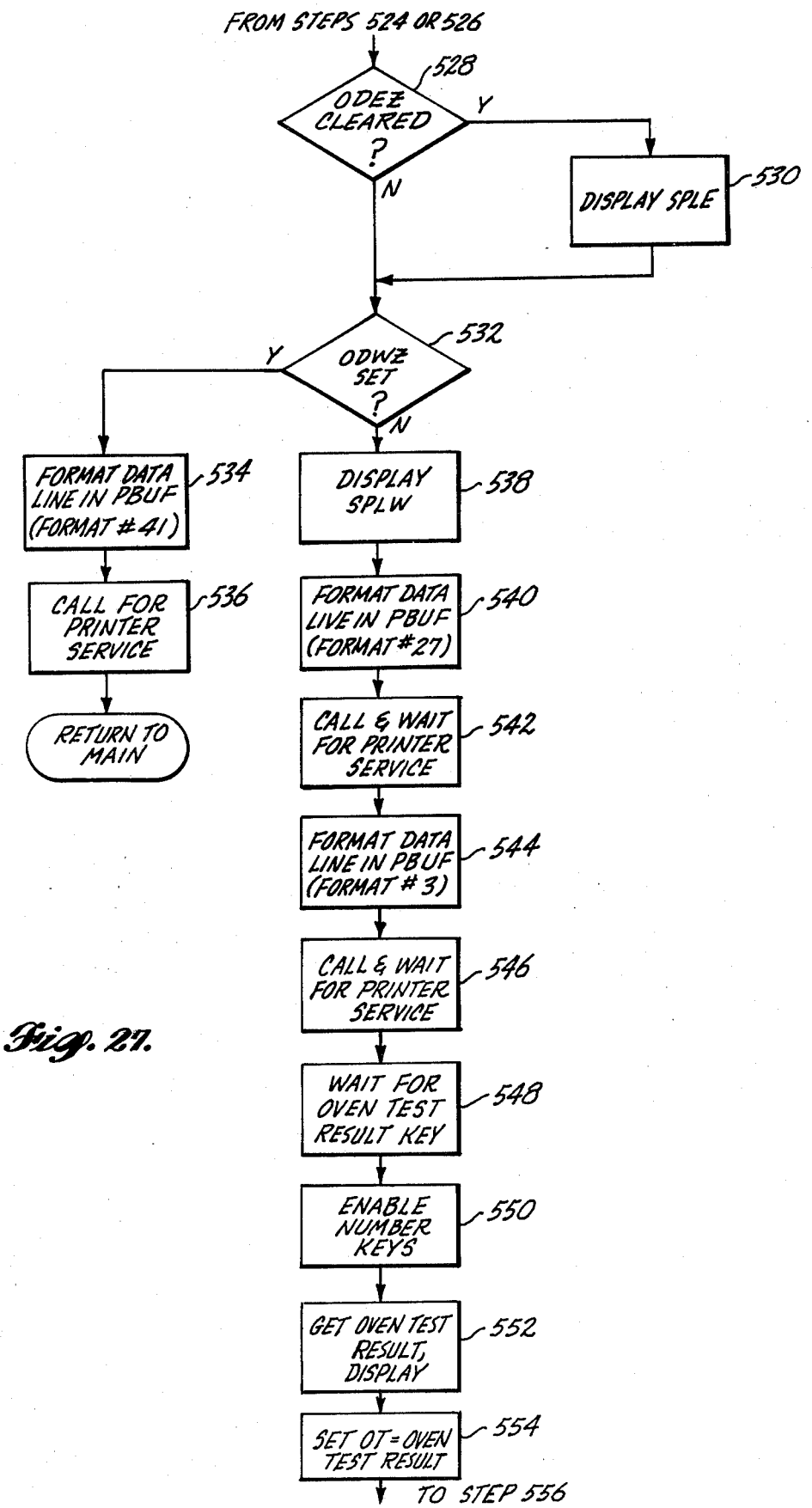
Figure 28:
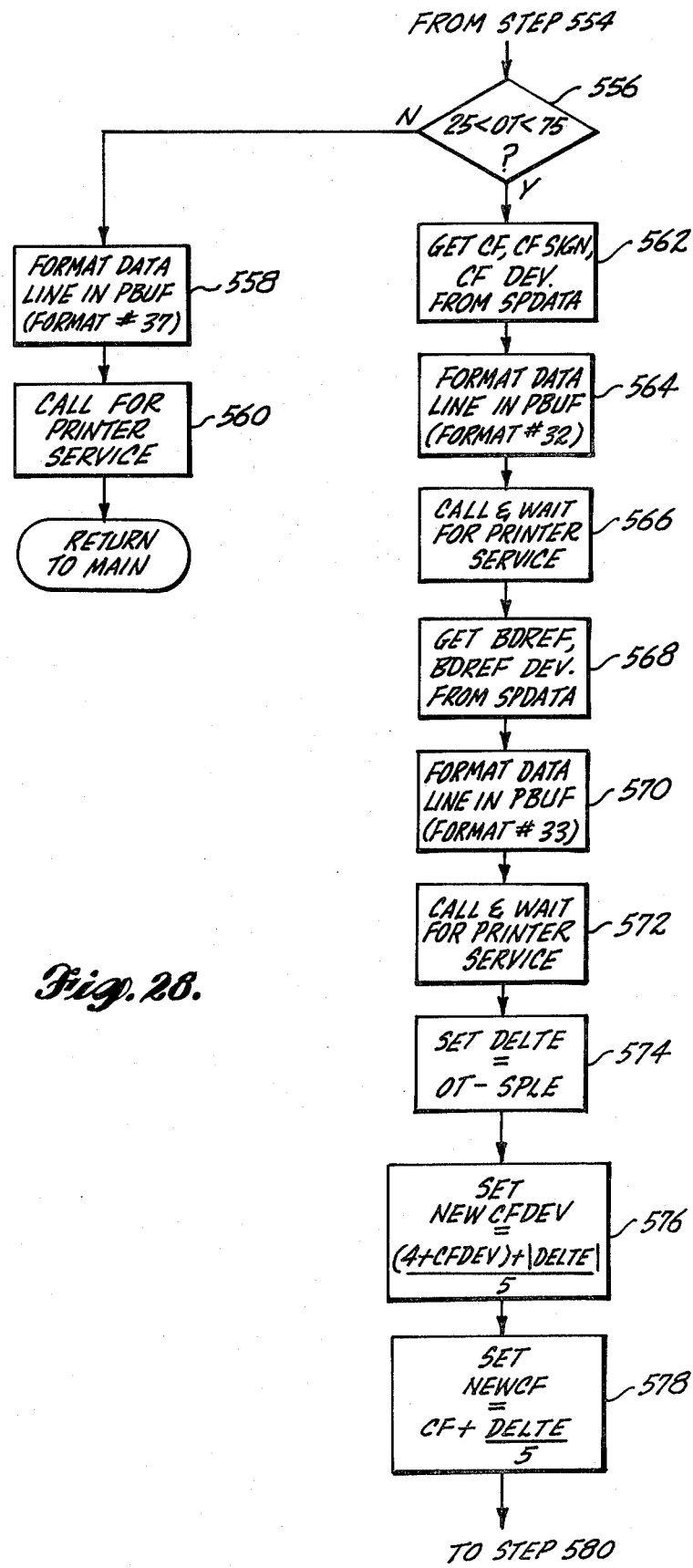

Accordingly, when the determination in step 244 is affirmative, CPU 112 proceeds, in step 246, to determine if the WTLO operation flag has been set. If the determination in step 246 is affirmative, the sample box 16 most likely has been incompletely filled, whereupon CPU 112 proceeds directly to an INCOMPLETE FILL subroutine (FIG. 23). If the determination in step 246 is negative, CPU 112 next determines, in step 248, if the ELNG operation flag has been set. If the determination in step 248 is negative, CPU 112 determines, in step 250, if either the CONF or the BDFLAG operation flags have been set. If the determinations in either steps 248 or 250 are affirmative, further computations based on the electronic oven dry percentage cannot be made, either because the measured moisture and conductivity are invalid, or because the supplier's BD bit has been set to indicate that all computations should be made using only the density oven dry percentage. If the determinations in steps 248 and 250 are negative, CPU 112 determines, in step 252, if the FRZN operation flag has been set. As described hereinafter, the FRZN operation flag is set when a "frozen" condition is detected, and remains set for a predetermined number of successive measurement cycles. If FRZN has been set for a previous sample and not cleared for the current sample, the current sample most likely is frozen. Since further computations in the case of a frozen sample require the use of the density oven dry percentage, these computations cannot be made if the density oven dry percentage is invalid. Even though the determination in step 252 is negative, the current sample may yet be frozen, so that CPU 112 proceeds, in step 254, to determine if the TFLG and the DLTA operation flags have been set. When the determinations in any of steps 248, 250, 252 or 254 are affirmative, further computations for the sample cannot be made, so that CPU 112 proceeds directly to a NO GOOD DATA subroutine (FIG. 24). If the determinations in these steps are each negative, however, CPU 112 proceeds directly to the ELECTRONIC ONLY subroutine.

Figure 21:
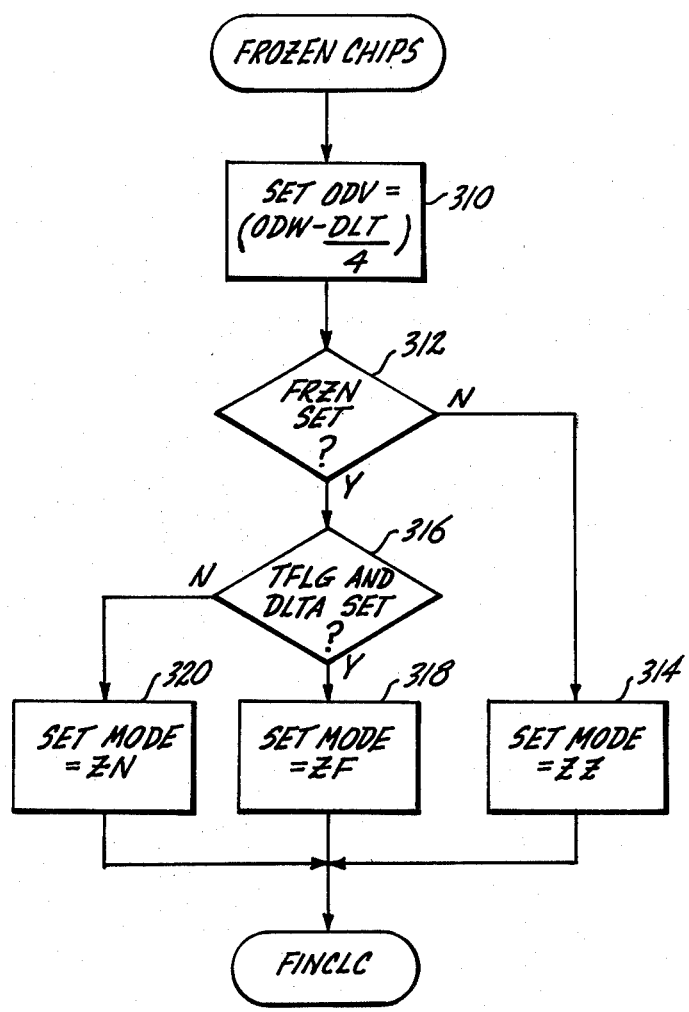
FIG. 21 is a flow chart of the program steps undertaken by the microprocessor in a FROZEN CHIPS subroutine.

Assuming now that neither TWLV nor RFNG has been set, the determination in step 244 is negative, whereupon CPU 112 proceeds, in step 256, to determine if the ODWB operation flag has been set. If the determination in step 256 is affirmative, sample box 16 most likely has been incompletely filled, whereupon CPU 112 proceeds directly to the INCOMPLETE FILL subroutine. If the determination in step 256 is negative, CPU 112 next proceeds to determine, in step 258, if the TFLG and DLTA operation flags have been set. If the determination in step 258 is affirmative, the sample contains frozen moisture, whereupon CPU 112 proceeds, in step 260, to set the FRZN operation flag and to clear the FZCT counter. From step 260, CPU 112 proceeds directly to a FROZEN CHIPS subroutine (FIG. 21).

Normal variations in the measurements made during successive measurement cycles may result in either of the TFLG or DLTA operation flags not being set for a sample subsequent to the one in which frozen moisture was first detected. It is likely, however, that the subsequent sample contains frozen moisture. Therefore, if the determination in step 258 is negative, CPU 112 determines, in step 262, if the FRZN operation flag has been set (e.g., for a previous sample). If the determination in step 262 is affirmative, CPU 112, in step 264, increments the count within FZCT by one and then determines, in step 266, if FZCT contains the count of eight. If the determination in step 266 is negative, e.g., the particular sample is not the eighth successive sample following the sample during which frozen moisture was first detected, CPU 112 proceeds directly to the FROZEN CHIPS subroutine. If the determination in step 266 is affirmative, CPU 112 proceeds, in step 268 to clear the FRZN operation flag and then proceeds directly to the FROZEN CHIPS subroutine. For the next sample, the TFLG and DLTA operation flags must both be set in order for CPU 112 to proceed to the FROZEN CHIPS subroutine.

If the determination in step 262 is negative, CPU 112 proceeds, in step 270, to determine if the CONF operation flag has been set. If the determination in step 270 is negative, CPU 112 determines, in step 272, if the BDFLAG operation flag has been set. If the determinations in either steps 270 or 272 are affirmative, further computations cannot be based on the electronic oven dry percentage, whereupon CPU 112 proceeds directly to the BULK DENSITY ONLY subroutine. If the determinations in both steps 270 and 272 are negative, CPU 112 proceeds directly to a NORMAL subroutine (FIG. 18).

Figure 22:
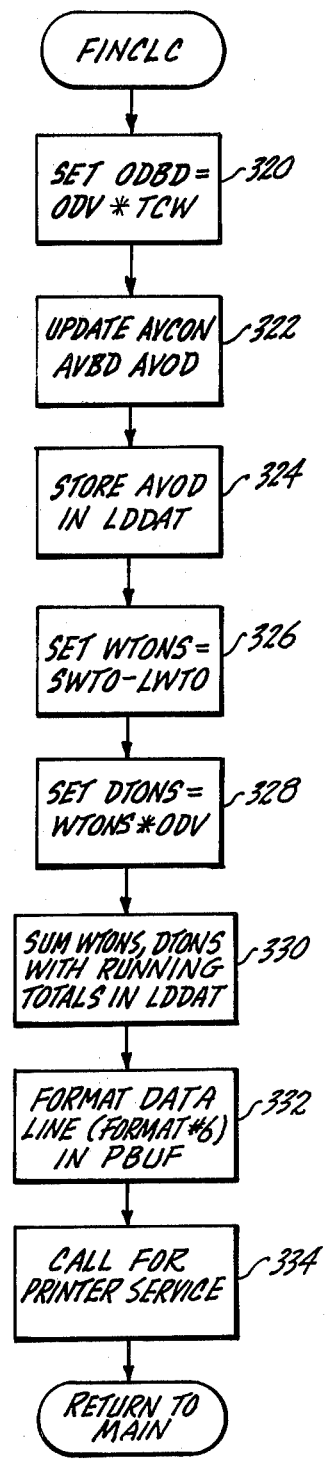
FIG. 22 is a flow chart of the program steps undertaken by the microprocessor in a FINCLC subroutine.

With reference now to FIG. 18, CPU 112 will enter the NORMAL subroutine only if a determination has been made that the sample is not frozen and that both the electronic and density oven dry percentages are based on valid data and have not been otherwise disqualified. In step 280, CPU 112 reduces the normal variation between computations of the electronic and density oven dry percentages by taking the average thereof and by storing the average in ODV (the verified oven dry percentage). In order to supply information to the user as to the method selected to determine oven dry percentage and the reason for the selection, the MODE data byte is updated for each sample so as to contain a two-digit code (which is subsequently printed out as described hereinafter). From step 280, CPU 112 accordingly proceeds, in step 282, to store blank data in MODE to thereby signify that computations were made through the NORMAL subroutine. From step 282, CPU 112 proceeds directly to a FINCLC subroutine (FIG. 22).

With reference now to FIG. 19, CPU 112 will enter the ELECTRONIC ONLY subroutine if the density oven dry percentage is disqualified (e.g., MELC is set), or if the density oven dry percentage is based on invalid data. In step 284, CPU 112 sets ODV=ODE and clears ODW. From step 284, CPU 112 determines, in step 286, if the TWLV operation flag has been set. If the determination in step 286 is negative, CPU 112 proceeds, in step 288, to set the digits in MODE to "RD". If the determination in step 286 is affirmative, CPU 112 next determines, in step 290, if the RFNG operation flag has been set. If the determination in step 290 is negative, CPU 112 proceeds, in step 292, to set the digits in MODE to "TW". If the determination in step 290 is affirmative, CPU 112 proceeds, in step 294, to set the digits in MODE to "TR". From either steps 288, 292 or 294, CPU 112 proceeds to the FINCLC subroutine.

With reference now to FIG. 20, CPU 112 will enter the BULK DENSITY ONLY subroutine if the electronic oven dry percentage has been disqualified (e.g., MBDO is set), or, if the supplier's BD bit has been set (e.g., BDFLAG is set), or if the electronic oven dry percentage is based on invalid data. In step 296, CPU 112 sets ODV=ODE and clears ODE. Thereafter, CPU 112 determines, in step 298, if the CONF operation flag has been set. If the determination in step 298 is negative, CPU 112 proceeds, in step 300, to set the digits in MODE to "DF". If the determination in step 298 is affirmative, CPU 112 proceeds, in step 302, to determine if the BDFLAG operation flag has been set. If the determination in step 302 is negative, CPU 112 proceeds, in step 304, to set the digits in MODE to "SA". If the determination in step 302 is affirmative, CPU 112 proceeds, in step 306, to set the digits in MODE to "SD". From either step 300, 304 or 306, CPU 112 proceeds to the FINCLC subroutine.

With reference now to FIG. 21, CPU 112 will enter the FROZEN CHIPS subroutine only if frozen moisture has been detected. In addition, it will have been determined that both the electronic and density oven dry percentages are each based on valid data and that neither have been disqualified.

In step 310, CPU 112 computes the verified oven dry percentage of the sample by setting $ODV=(ODW-DLT/4)$. As previously indicated, DLT/4 is a measure of the degree of frozenness of the sample. The divisor "4" represents the scaling constant k which has been found to be substantially constant, notwithstanding the type and material characteristics of the chips within the sample. As a result of the computations undertaken in step 310, the oven dry percentage is decreased from the density oven dry percentage in proportion to the degree of frozenness of the sample. Thereafter, in step 312, CPU 112 determines if the FRZN operation flag has been set. If the determination in step 312 is negative, CPU 112 proceeds, in step 314, to set the digits in MODE to "ZZ". If the determination in step 314 is affirmative, CPU 112 determines, in step 316, if the TFLG and DLTA operation flags have been set. If the determination in step 316 is affirmative, CPU 112 proceeds, in step 318, to set the digits in MODE to "ZF". If the determination in step 316 is negative, CPU 112 proceeds, in step 320, to set the digits in MODE to "ZN". From either step 314, 318 or 320, CPU 112 proceeds to the FINCLC subroutine.

With reference now to FIG. 22, CPU 112 will enter the FINCLC subroutine from the NORMAL, ELECTRONIC ONLY, BULK DENSITY ONLY, or FROZEN CHIPS subroutines. Initially, CPU 112 computes an oven dry bulk density for the sample by setting $ODBD=ODV*TCW$. The verified oven dry percentage ODV is that selected in the preceding subroutines. CPU 112 next updates the values of the AVCON, AVBD and AVOD data bytes (by respectively averaging the current contents of those bytes with, respectively, CCN, ODBD, and ODV). In step 324, CPU 112 stores AVOD in the appropriate location in the LDDAT table (determined by the S/L code in RSLCD). In step 326, CPU 112 determines the wet weight that has passed over weightometer 132 during the previous measurement cycle by setting $WTONS=SWTO-LWTO$. As noted from Table II, SWTO comprises the contents of WTOCNT at the time of the record full signal that initiated the current measurement cycle, and LWTO comprises the contents of WTOCNT at the time of the record full signal that initiated the previous measurement cycle. In step 328, CPU 112 determines the dry weight that has passed over weightometer 132 by setting $DTONS=WTONS*ODV$. In step 330, CPU 112 sums WTONS and DTONS with corresponding running wet tons WWT and running dry ton DWT in the LDDAT table (at a location determined by the S/L code in RSLCD). As a result of the actions undertaken in steps 324–330, LDDAT accordingly contains an updated average oven dry percentage for the load, an updated total dry tons of the load, and an updated total wet tons of the load. In step 332, CPU 112 formats a data line, in print format #6, in the print buffer PBUF, and then, in step 334, calls for printer service. From 334, CPU 112 returns to its main program loop (FIG. 13). When printer service is made, the conductivity (CCN), oven dry bulk density (ODBD), verified oven dry percentage (ODV), mode (MODE), and wet weight (WTONS) are printed out in a single data line (print format #6) following the header (print format #5) previously discussed.

With reference to FIG. 23, CPU 112 will enter the INCOMPLETE FILL subroutine if a repeated low tare weight violation has occurred or the supplier's bulk density reference is invalid and the net weight of the sample is below a predetermined value, or, if the density oven dry percentage is greater than a predetermined value. In successive steps 340, 342, 344 and 346, CPU 112 accordingly formats data lines in the print buffer PBUF, in formats #12 and #13 (FIG. 31A), and calls for printer service. When printer service is made, the user is informed of the incomplete fill, and is given the full weight (FWT) and tare weight (TWT) so that corrective action may be taken. No computed sample data, however, is printed.

With reference to FIG. 24, CPU 112 will enter the NO GOOD DATA subroutine if the density oven dry percentage is used on invalid data and the electronic oven dry percentage is disqualified or is based on invalid data. In step 348, CPU 112 formats a data line in the print buffer PBUF in format #31 (FIG. 31B), in which each operation flag has associated therewith a given character position in the data line and in which a "F" is printed in the character position if the operation flag has been set. In step 350, CPU 112 calls and waits for printer service. In step 352, CPU 112 formats data lines in the print buffer PBUF in formats #43 and 44 (FIG. 31B) which include certain data for the sample (FWT, TWT, PCM, TMP, and CCN). In step 354, CPU 112 calls and waits for printer service for each line. No computed sample data, however, is printed.

Upon exiting from either the INCOMPLETE FILL or the NO GOOD DATA subroutines, CPU 112 returns to its main program loop.

Referring now back to FIG. 14, it will be remembered that subsequent to the record empty signal, CPU 112 saves and scales the empty or tare weight of sample box 16, and stores the result in TWT (in MTSERV and MTSCAL). Thereafter, CPU 112 enters the MTPRO subroutine (FIG. 24) and conducts certain tests on TWT.

In step 360, CPU 112 determines if TWT is greater than a predetermined high limit, e.g., 5 lbs/ft$^3$. If the determination in step 360 is negative, CPU 112 next takes the difference between the current tare weight TWT and the tare weight PTWT determined during the previous measurement cycle, by setting $\phi = TWT - PTWT$. In step 364, CPU 112 determines if the absolute value of $\phi$ is greater than a predetermined amount, e.g., 2 lbs/ft$^3$. If the determination in step 364 is negative, CPU 112 next determines, in step 366, if the tare weight is less than a predetermined low limit, e.g., 0.2 lbs/ft$^3$. If the determination in step 366 is negative, the tare weight represented by TWT is acceptable and CPU 112 proceeds, in step 368, to clear the low tare weight counter LWCT, the high tare weight counter HICT, and the tare weight shift counter SHCT. After setting PTWT=TWT, CPU 112 returns to its main program loop.

Let it be assumed that the tare weight of the current sample is greater than the high limit and that the determination in step 360 is accordingly affirmative. As a result, CPU 112 proceeds, in step 370, to increment the HICT counter by one, to format a data line (which includes a high tare weight message and the value of TWT) in the print buffer PBUF, in format #14 (FIG. 31A) and calls and waits for printer service in subsequent step 372. Thereafter, CPU 112, in step 374 determines if HICT contains a count of five. Let it be assumed that the current sample is the first sample for which a high tare weight violation has occurred. As a result, the determination in step 374 is negative, whereupon CPU 112 proceeds, in step 376, to supply a dump output signal to actuating means 80 in an attempt to clear any material that may be causing the tare weight to be high, and additionally clears the MTFG operation flag. From step 376, CPU 112 returns to its main program loop. During the next subsequent measurement cycle, the fact that MTFG has been cleared in step 376 causes CPU 112 to skip the FLSERV, SEFL and CLCFUL subroutines, so that no computations are made for the then-current sample. CPU 112 then returns to the MTPRO subroutine. If the tare weight is still high, HICT is again incremented, the appropriate information is printed, and a test is made to see if MICT contains a count of five. If the high tare weight violation persists for five successive measurement cycles, the determination in step 374 is affirmative, whereupon CPU 112 proceeds, in step 378, to clear HICT and to successively format certain data lines in PBUF, in formats #17, 18, 19 and 20 (FIG. 31A), and calls and waits for printer service in step 380. CPU 112 then provides an output signal to audible alarm 134 in step 382, provides a dump output signal and clears the MTFG operation flag in step 376, and returns to its main program loop. As a result, the user is informed that the condition causing the high tare weight violation cannot be cured by repeated attempts to open sample box 16, and suggestions are made as to the possible reason for that condition.

Let it now be assumed that a tare weight shift has occurred and that the determination in step 364 is affirmative. As a result, CPU 112 proceeds, in step 384, to increment the SHCT counter by one, and to format a data line (which includes a tare weight shift message and the value of $\phi$) in the print buffer PBUF, in format #16 (FIG. 31A), and calls and waits for printer service in step 386. Thereafter, in step 388, CPU 112 determines if SHCT contains a count of five. Assuming that the current sample is the first for which a tare weight shift violation has occurred, the determination in step 388 is negative, whereupon CPU 112 proceeds in step 376, to supply a dump output signal to actuating means 80 and to clear MTFG. If the tare weight shift violation persists for five successive measurement cycles, the determination in step 388 is affirmative, whereupon CPU 112 proceeds, in step 390, to clear SHCT, to successively format certain data lines in PBUF, in formats #19, 21 and 22 (FIG. 31A), and calls and waits for printer service in step 392. CPU 112 then provides an output signal to audible alarm 134 in step 382, provides a dump output signal and clears MTFG in step 376, and returns to its main program loop. As a result, the user is informed that the condition causing the tare weight shift violation cannot be cured by repeated attempts to open sample box 16 and suggestions are made as to the possible reason for that condition.

Let it now be assumed that the tare weight of the current sample is below the low limit and that the determination in step 366 is affirmative. As a result, CPU 112 proceeds, in step 394, to increment the LWCT counter by one, and to format a data line (which includes a low tare weight message and the value of TWT) in PBUF, in format #15 (FIG. 31A). After calling and waiting for printer service in step 396, CPU 112 determines, in step 398, if the count within LWCT is greater than three. Assuming that the current sample is the first sample for which a low tare weight violation has been detected, the determination in step 398 is negative, whereupon CPU 112 proceeds, in step 376, to supply a dump output signal to actuating means 80 and to clear MTFG. If the low tare weight violation persists for three successive measurement cycles, the determination in step 398 is affirmative, whereupon CPU 112 proceeds, in step 400, to set the TWLV operation flag and to format a data line in PBUF, in format #23 (FIG. 31A). After calling for printer service in step 402, CPU 112 returns to its main program loop. During all succeeding measurement cycles for the load, the fact that TWLV has been set causes CPU 112 to disqualify the density oven dry percentage and to use only the electronic oven dry percentage.

As previously described, the microprocessor permits the supplier's correction factor and bulk density reference to be updated in response to information obtained from an oven test of a particular "sample taken". When the correction factors and bulk density reference for a supplier are initially entered into the microprocessor (as previously described), the values thereof are usually estimated.

To obtain sample data necessary to initially update the correction factor, the user actuates the ALL ELEC ONLY key, as the result of which the electronic oven dry percentage is selected as previously described. Following this action, the microprocessor is permitted to pass through a number of measurement cycles to obtain sample data for a number of samples of wood chips from the supplier. During each of these measurement cycles, the user actuates switch 108 so that a sample taken signal is provided to switch monitor 124. Following the completion of the MTPRO subroutine in each measurement cycle in which a sample taken signal has been provided, CPU 112 enters the SAMTKN subroutine in FIG. 25A (reference the timing of the chip meter sequences in FIG. 14).

It is undesirable to use any sample data in updating the supplier's correction factor (or bulk density reference) if the sample contains frozen moisture, if the verified oven dry percentage is based on invalid data or is disqualified, or if the sample box 16 has been incompletely filled. Accordingly, CPU 112, in step 410, determines if the FRZN operation flag has been set. If the determination in step 410 is affirmative, CPU 112 proceeds, in step 412, to format a data line in the print buffer PBUF, in format #27' (FIG. 31B), and to call for printer service in step 414. CPU 112 thereafter returns to its main program loop. Accordingly, a printout is made to inform the user that the sample contains frozen moisture.

If the determination in step 410 is negative, CPU 112 determines, in step 416, if it is passed through the NO GOOD DATA subroutine for the sample. If the determination in step 416 is affirmative, CPU 112 proceeds, in steps 418 and 420, to successively format data lines in the print buffer PBUF, in formats #27" and 31 (FIG. 31B), and to successively call for printer service, whereupon CPU 112 returns to its main program loop. A printout is thus made to inform the user of the flags that have been set that have caused CPU 112 to pass through the NO GOOD DATA subroutine.

If the determination in step 416 is negative, CPU 112 proceeds, in step 422, to determine if it has passed through the INCOMPLETE FILL subroutine for the sample. If the determination in step 422 is affirmative, CPU 112, in steps 424 and 426, successively formats data lines in the print buffer PBUF, in formats #27", 12 and 13 (FIGS. 31B and 31A), and successively calls for printer service, after which CPU 112 returns to its main program loop. A printout is thus made to inform the user that sample box 16 was incompletely filled.

If the determination in step 422 is negative, the sample data is valid, whereupon CPU 112 proceeds, in step 428, to store the supplier code (in SPLCD), the density oven dry percentage ODW, and the electronic oven dry percentage ODE in the SIDTBL table (see Table I), with the location of this entry in SIDTBL determining a sample ID number for the sample. Thereafter, in steps 430 and 432, CPU 112 successively formats certain data lines in the print buffer PBUF, in formats #27, 3, 4, 8, 9 and 10 (FIG. 31B) and successively calls for printer service, whereupon CPU 112 returns to its main program loop. A printout is thus made of the sample ID number, the supplier number, the supplier's correction factor and sign, the supplier's bulk density reference, the moisture (PCM), the net weight (TCW), the verified oven dry percentage (ODV), the mode of computation (MODE), the conductivity (CCM), the temperature (TMP), and the tare weight (TWT) of the sample.

For each sample taken, the user subjects the sample to an oven test in order to determine an "oven test" moisture percentage. The oven test moisture percentages and the moisture data (PCM) for the samples are each averaged, and an updated correction factor may be calculated through use of the relationship updated correction factor =
average moisture percentage based on electrical -continued
impedance − average oven test moisture percentage In a similar manner, an updated bulk density reference is obtained by the user actuating the ALL DENS ONLY key, and then actuating switch 108 for a plurality of samples. These samples are then each subjected to an oven test in order to determine an oven test oven dry percentage for each sample. For each sample, a bulk density reference may be calculated using the relationship $$\text{bulk density reference} = \frac{\text{oven test oven dry percentage} \ast \text{net weight}}{100}$$

The bulk density references are then averaged to obtain the updated bulk density reference.

Thereafter, the updated correction factor and bulk density reference are entered into the microprocessor as previously described, and accordingly stored in the SPDATA table.

Provision is also made for automatically correcting the supplier's correction factor and bulk density reference. In order to obtain sample data necessary for this automatic correction, the user actuates switch 108 for a single sample, whereupon certain data is stored in SIDTBL, a sample ID number is assigned and a printout is made, all as previously described.

The user then takes the sample and conducts an oven test thereon in order to determine the true oven dry percentage thereof (the oven test result). After obtaining the oven test result, the user returns and actuates the SAMPLE ID # key in keyboard 136 (see FIG. 10 and Table II). As a result, CPU 112 enters the AUTOCF subroutine (FIGS. 26–29) through its main program loop (step 164, FIG. 13).

In step 500, CPU 112 sets the display to format #3 (FIG. 30) and enables the number keys of keyboard 136. The user then enters the sample ID number (from the printout) through the number keys. In step 502, CPU 112 obtains the thus-entered sample ID number and transfers it to the sample ID number entry field of the display. In step 504, CPU 112 determines if the sample ID number is valid, e.g., does it correspond to an entry in SIDTBL. If the determination in step 504 is negative, CPU 112 proceeds, in step 506, to format a data line in the print buffer PBUF, in format #41 (FIG. 31B), and calls for printer service in step 508, whereupon CPU 112 returns to its main program loop. A printout is thus made to inform the user that the sample ID number is not valid. Thereafter, the user must again actuate the SAMPLE ID # key and enter a correct sample ID number. At this time, the determination in step 504 is affirmative, whereupon CPU 112, in step 510, retrieves the entry from SIDTBL corresponding to the sample ID number. In step 512, CPU 112 determines if ODE in the thus-retrieved entry is zero. If the determination in step 512 is affirmative, CPU 112 proceeds, in step 514, to set an ODEZ operation flag. If the determination in step 512 is negative, CPU 112 proceeds, in step 516, to transfer the contents of ODE to the SPLE data byte. From either step 514 or step 516, CPU 112 next determines, in step 518, if the thus-retrieved ODW is zero. If the determination in 518 is affirmative, CPU 112 proceeds, in step 520, to set an ODWZ operation flag. If the determination in step 518 is negative, CPU 112 proceeds, in step 522, to transfer the contents of ODW to the SPLW data byte. From either step 520 or step 522, CPU 112 determines, in step 524, if both ODEZ and ODWZ have been cleared. If the determination in step 524 is affirmative, CPU 112 proceeds, in step 526, to compute the average of SPLE and SPLW, and to display the thus-computed average in the measured result field of the display. If the determination in step 524 is negative, CPU 112 next determines, in step 528, if ODEZ has been cleared. If the determination in step 528 is affirmative, CPU 112 proceeds, in step 530, to display SPLE in the measured result field of the display. From step 530, or from step 528 if the determination therein in negative, CPU 112 proceeds, in step 532, to determine if ODWZ has been set. At this point, it should be noted that automatic correction of the supplier's correction factor and bulk density reference will be made only if both the electronic and density oven dry percentages are based on valid data and have not been disqualified. Accordingly, if the determination in step 532 is affirmative, this condition has been not met, whereupon CPU 112, proceeds, in steps 534 and 536, to format a data line in the print buffer PBUF, in format #41 (FIG. 31B), and to call for printer service, whereupon CPU 112 returns to its main program loop.

If the determination in step 532 is negative, CPU 112 proceeds, in step 538, to display SPLW in the measured result field of the display. Accordingly, if the sample is valid, the average oven dry percentage, the electronic oven dry percentage, and the density oven dry percentage are displayed in succession in the measured result field of the display.

From step 538, CPU 112 proceeds, in steps 540, 542, 544 and 546, to successively format data lines in the print buffer PBUF, in formats #27 and #3 (FIG. 31B), and successively calls and waits for printer service. As a result, a printout is made of the sample ID number and the supplier number (from the supplier code). Thereafter, CPU 112 in step 548, waits for the OVEN TEST RESULT key to actuated. The user then actuates that key, whereupon CPU 112, in step 550, enables the number keys. The user then enters the oven test result, whereupon CPU 112, in step 552, retrieves the oven test result and transfers it the oven test entry field of the display. In step 554, CPU 112 transfers the contents of the oven test result in the display to the OT data byte.

Thereafter, CPU 112, in step 556, determines if the oven test result is within a certain range, e.g., greater than 25% and less than 75%. If the determination in step 556 is negative, the oven test result is invalid, whereupon CPU 112, in steps 558 and 560, formats a data line in the print buffer PBUF, in format #37 (FIG. 31B), and calls for printer service, whereupon CPU 112 returns to its main program loop.

If the determination in step 556 is affirmative, CPU 112, in steps 562, 564, 566, 568, 570 and 572, retrieves the supplier-related data from the SPDATA table, successively formats data lines in the print buffer, in formats #32 and #33 (FIG. 31B), and calls and waits for printer service. A printout is thus made of the current or "old" correction factor, correction factor sign, correction factor deviation, bulk density reference and bulk density reference deviation for the supplier.

In steps 574, 576 and 578, CPU 112 proceeds to compute a "new" correction factor deviation and correction factor, and, in steps 580, 582 and 584, to compute a "new" bulk density reference deviation and bulk density reference.

In step 574, CPU 112 takes the difference between the oven test result and the electronic oven dry percentage, by setting $DELTE = OT - SPLE$. In step 576, CPU 112 computes the new correction factor deviation according to the relationship $$NEWCFDEV = (4 + CFDEV + |DELTE|)/5$$

It will be appreciated that by using this relationship, the new correction factor deviation is weighted to be 80% (4/5) of the old correction factor deviation plus 80% of the absolute value of the difference (DELTE) between the oven test result and the electronic oven dry percentage.

In step 578, CPU 112 computes the new correction factor according to the relationship $$NEWCF = CF + DELTE/5$$

It will be appreciated that by using this relationship, a weighting factor of 20% is applied to DELTE before summing with the old correction factor.

In step 580, CPU 112 determines the difference between the oven test result and the density oven dry percentage by setting $DELTW = OT - SPLW$. In step 582, CPU 112 computes the new bulk density reference deviation according to the relationship $$NEWBDREFDEV = (4 = BDREFDEV + |DELTW|)/5$$

In step 584, CPU 112 computes the new bulk density reference according to the relationship $$NEWBDREF = BDREF + \frac{BDREF * 100}{SPLW} \left( \frac{DELTW}{5} \right) \bigg/ 100$$

As with the new correction factor deviation and new correction factor, the new bulk density reference deviation and the new bulk density reference are computed using, respectively, 80% and 20% weighting factors.

In steps 586, 588, 590 and 592, CPU 112 successive formats data lines in the print buffer PBUF, in formats #32' and #33' (FIG. 31B), and successively calls and waits for printer service. A printout is thus made of the new correction factor, correction factor deviation, bulk density reference, and bulk density reference deviation.

CPU 112 thereafter proceeds, in step 594, to wait for the STORE TEST RESULT key. When the user actuates this key, CPU 112 proceeds, in step 596, to store the new supplier-related data in the SPDATA table, clears the ODEZ and ODWZ operation flags in step 596 and thereafter returns to its main program loop.

With reference now back to Table IV, the user may, through keyboard 136, obtain a display or printout of certain data stored in RAM 116 or RAM 118.

By actuating the PRINT ALL SUPL# key, the user may obtain a printout of the supplier number, correction factor, and bulk density reference (in SPLIST and SPDATA), for all suppliers in order of increasing supplier number.

By actuating the PRINT LOAD DATA key, the user may obtain a printout of the supplier number, load number, average oven dry percentage (AVOD), dry tons (DWT), and wet tons (WWT) from LDDAT for all supplier number/load number combinations. If the user has already actuated the PRINT LOAD DATA key, subsequent actuation of the ERASE LOAD DATA key erases the entire contents of LDDAT.

The user may wish to remove all data related to a particular supplier from the tables. The user actuates the SUPL# key and enters the thus-displayed supplier number through keyboard 136. If the thus-entered (and displayed) supplier number corresponds to a number in SPLIST, the user must actuate either the CORR FACTOR key or BULK DENSITY REF key to set the display to format #2. Subsequent actuation of the ERASE SUPL# key then erases all supplier-related data for the supplier from the tables in RAM 116. In addition, a printout is obtained of the supplier number and the correction factor and bulk density reference therefor.

The user may wish to obtain a display of the total weight that has passed over weightometer 132 during the current load. The actuation of the DISPLAY WEIGHT key sets the display to format #4, whereupon the current total weight (the contents of WTONCNT) and the average oven dry percentage for the load (AVOD) are displayed in appropriate fields of the display.

Finally, the user may wish to obtain a printout of the input data. Actuation of either the PRINT METER INPUTS key, or of switch 110, results in a printout of the current values of the moisture, conductivity, weight and temperature data in ATDBL.

While the invention has been described with reference to a preferred embodiment, it is to be clearly understood by those skilled in the art that the invention is not limited thereto. Rather, the scope of the invention is to be interpreted only in conjunction with the appended claims.

The embodiments of the invention in which an exclusive property or privilege is claimed are defined as follows:

1. A method for detecting the presence of frozen moisture in a sample of particulate material, said method comprising the steps of:
    determining a moisture percentage for the sample by measuring the electrical impedance thereof;
    measuring the wet bulk density and temperature of the sample;
    determining an electronic oven dry percentage for the sample from said moisture percentage based on electrical impedance;
    determining a density oven dry percentage for the sample from said measured wet bulk density; and,
    detecting the presence of frozen moisture if said measured temperature is below a predetermined value and if said electronic oven dry percentage differs from said density oven dry percentage in a predetermined manner.

2. A method as recited in claim 1, wherein said steps are each repeated in a plurality of successive measurement cycles for a plurality of successive samples of the particulate material, and further comprising the step of maintaining said detection of frozen moisture throughout a predetermined number of measurement cycles successively subsequent to a measurement cycle in which said detection of frozen moisture was first made.

3. A method as recited in claim 1, wherein said electronic oven dry percentage is determined according to the relationship $$\text{electronic oven dry percentage} = 100 - \text{moisture percentage based on electrical impedance} \pm \text{a correction factor,}$$

said correction factor being related to the particulate material from which the sample was taken.

4. A method as recited in claim 3, wherein said correction factor is determined by:
    determining a moisture percentage for each sample by measuring the electrical impedance thereof;
    subjecting each of a plurality of samples of the particulate material to an oven test so as to determine an oven test moisture percentage therefor;
    determining the average of said moisture percentages based on electrical impedance;
    determining the average of said oven test moisture percentages; and,
    determining said correction factor according to the relationship $$\text{correction factor} = \text{average moisture percentage based on electrical impedance} - \text{average oven test moisture percentage.}$$

5. A method as recited in claim 1, wherein said density oven dry percentage is determined according to the relationship $$\text{density oven dry percentage} = (\text{a bulk density reference/measured wet bulk density})*100,$$

said bulk density reference being substantially equal to an average oven dry bulk density of the particulate material.

6. A method as recited in claim 5, wherein said bulk density reference is determined by:
    measuring the wet bulk density of each of a plurality of samples of the particulate material;
    subjecting each sample to an oven test so as to determine an oven test oven dry percentage therefor;
    determining a bulk density reference for each sample according to the relationship:

$$\text{bulk density reference for sample} = \frac{\text{oven test oven dry percentage (measured wet bulk density)}}{100}$$

and, taking the average of said bulk density references for said samples to obtain said bulk density reference for the particulate material.

7. A method as recited in claim 1, wherein said particulate material comprises wood chips.

8. A method as recited in claim 7, wherein said predetermined value of temperature is substantially 5° C.

9. A method as recited in claim 1, wherein frozen moisture is detected if said electronic oven dry percentage is greater than said density oven dry percentage by a predetermined amount.

10. A method as recited in claim 9, wherein said predetermined amount is at least equal to the normal variation between said electronic and said density oven dry percentages when frozen moisture is not present in the sample.

11. A method as recited in claim 10, wherein the particulate material comprises wood chips.

12. A method as recited in claim 11, wherein said predetermined amount is substantially 5%.

13. A method as recited in claim 1, further comprising the steps of:
determining a degree of frozenness factor for the sample as a function of said electronic and said density oven dry percentages; and, determining a verified oven dry percentage for the sample by modifying said density oven dry percentage in accordance with said degree of frozenness factor.

14. A method as recited in claim 13, wherein said degree of frozenness factor is determined according to a linear function of said electronic and said density oven dry percentages.

15. A method as recited in claim 13, wherein said verified oven dry percentage is determined by subtracting said degree of frozenness factor from said density oven dry percentage.

16. A method as recited in claim 15, wherein said verified oven dry percentage is determined according to the relationship verified oven dry percentage = density oven dry percentage $- k \Delta$, where $k \Delta$ is said degree of frozenness factor, k is a scaling constant, and $\Delta$ is substantially equal to the difference between said electronic and said density oven dry percentages.

17. A method as recited in claim 16, wherein the particulate material comprises wood chips, and wherein k is substantially equal to 0.25.

18. A method as recited in claim 16, wherein $\Delta$ is determined according to the relationship $\Delta =$ electronic oven dry percentage $-$ density oven dry percentage $- m$, wherein m is a constant at least equal to the normal variation between said electronic and said density oven dry percentages when frozen moisture is not present in the sample.

19. A method as recited in claim 18, wherein the particulate material comprises wood chips and wherein m is substantially 5%.

20. A method for determining the oven dry percentage of a sample of particulate material that contains frozen moisture, said method comprising the steps of:
determining a moisture percentage for the sample by measuring the electrical impedance thereof;
measuring the wet bulk density of the sample;
determining an electronic oven dry percentage for the sample from said moisture percentage based on electrical impedance;
determining a density oven dry percentage for the sample from said measured wet bulk density;
determining a degree of frozenness factor for the sample as a function of said electronic and said density oven dry percentages;
determining a verified oven dry percentage for the sample by modifying said density oven dry percentage in accordance with said degree of frozenness factor.

21. A method as recited in claim 20, wherein said degree of frozenness factor is determined according to a linear function of the difference between said electronic and said density oven dry percentages.

22. A method as recited in claim 20, wherein said verified oven dry percentage is determined by subtracting said degree of frozenness factor from said density oven dry percentage.

23. A method as recited in claim 22, wherein said verified oven dry percentage is determined according to the relationship verified oven dry percentage = density oven dry percentage $- k \Delta$, where $k \Delta$ is said degree of frozenness factor, k is a scaling constant, and $\Delta$ is substantially equal to the difference between said electronic and said density oven dry percentages.

24. A method as recited in claim 23, wherein the particulate material comprises wood chips, and wherein k is substantially equal to 0.25.

25. A method as recited in claim 23, wherein $\Delta$ is determined according to the relationship $\Delta =$ electronic oven dry percentage $-$ density oven dry percentage $- m$, where m is a constant at least equal to the normal variation between said electronic and said density oven dry percentages when frozen moisture is not present in the sample.

26. A method as recited in claim 25, wherein the particulate material comprises wood chips and wherein m is substantially 5%.

27. A method for determining the actual moisture percentage of a sample of particulate material that contains frozen moisture, said method comprising the steps of:
determining a moisture percentage for the sample by measuring the electrical impedance thereof;
measuring the wet bulk density of the sample;
determining a moisture percentage for the sample from said measured wet bulk density;
determining a degree of frozenness factor for the sample as a function of said moisture percentage based on bulk density and said moisture percentage based on electrical impedance; and,
determining the actual moisture percentage for the sample by modifying said moisture percentage based on bulk density in accordance with said degree of frozenness factor.

28. A method as recited in claim 27, wherein said degree of frozenness factor is determined according to a linear function of the difference between said moisture percentage based on bulk density and said moisture percentage based on electrical impedance.

29. A method as recited in claim 27, wherein said actual moisture percentage is determined by adding said degree of frozenness factor to said moisture percentage based on bulk density.

30. A method as recited in claim 29, wherein said actual moisture percentage is determined according to the relationship actual moisture percentage = moisture percentage based on bulk density $+ kM$, where kM is said degree of frozenness factor, k is a scaling constant, and M is substantially equal to the difference between said moisture percentage based on bulk density and said moisture percentage based on electrical impedance.

31. A method as recited in claim 30, wherein the particulate material comprises wood chips, and wherein k is substantially equal to 0.25.

32. A method as recited in claim 30, wherein M is determined according to the relationship $M$ = moisture percentage based on bulk density −
moisture percentage based on electrical impedance − $m$, where m is a constant at least equal to the normal variation between said moisture percentage based on bulk density and said moisture percentage based on electrical impedance when frozen moisture is not present in the sample.

33. A method as recited in claim 32, wherein the particulate material comprises wood chips and wherein m is substantially 5%.

34. An apparatus for determining a verified oven dry percentage for each of a plurality of successive samples of particulate material, said apparatus comprising:
a sample box for successively receiving, retaining, and discharging samples of the particulate material;
a weight sensor operatively associated with said sample box for providing a weight signal related to the weight thereof;
a temperature sensor operatively associated with said sample box for providing a temperature signal related to the temperature of a sample within said sample box;
an impedance measuring apparatus operatively associated with said sample box for providing conductivity and moisture signals respectively related to the measured electrical impedance of a sample within said sample box;
a timer means for providing a timing signal establishing a plurality of successive measurement cycles; and,
a data processor operating under control of a stored program for:
receiving said weight, temperature, conductivity and moisture signals, and said timing signal;
controlling said sample box so that said sample box receives, retains, and discharges a sample of the particulate material during each measurement cycle;
determining the wet bulk density of each sample from said weight signal;
determining an electronic oven dry percentage for each sample from said moisture signal;
determining a density over dry percentage for each sample from said wet bulk density;
testing said temperature signal, said electronic oven dry percentage and said density oven dry percentage to detect the presence of frozen moisture in any sample;
upon the detection of frozen moisture in a sample, determining a degree of frozenness factor for the sample from said electronic and said density oven dry percentages, and, selecting as said verified oven dry percentage a quantity equal to said density oven dry percentage for the sample, modified in accordance with said degree of frozenness factor.

35. An apparatus as recited in claim 34, wherein said data processor is operative to detect frozen moisture in a sample if said temperature signal represents a temperature less than a predetermined value and said electronic oven dry percentage for the sample differs from said density oven dry percentage for the sample by a predetermined amount.

36. An apparatus as recited in claim 35, wherein the particulate material comprises wood chips.

37. An apparatus as recited in claim 36, wherein said predetermined value of temperature is substantially 5° C.

38. An apparatus as recited in claim 36, wherein said predetermined amount is substantially 5%.

39. An apparatus as recited in claim 34, wherein said degree of frozenness factor is substantially equal to the product of a scaling constant k and a quantity Δ substantially equal to the difference between said electronic and said density oven dry percentages.

40. An apparatus as recited in claim 39, wherein the particulate material comprises wood chips and wherein k is substantially equal to 0.25.

41. An apparatus as recited in claim 39, wherein said quantity Δ is determined according to the relationship $\Delta$ =
electronic oven dry percentage − density oven dry percentage − $m$, where m is a constant at least equal to the normal variation between said electronic and said density oven dry percentages when frozen moisture is not present in the sample.

42. An apparatus as recited in claim 41, wherein the particulate material comprises wood chips and wherein m is substantially 5%.

43. An apparatus as recited in claim 34, wherein said data processor is further operative to select as said verified oven dry percentage for a sample an average of said electronic and density oven dry percentages therefor upon the failure to detect frozen moisture in the sample.

44. An apparatus as recited in claims 34 or 43, wherein said data processor is operative to determine if either of said electronic and said density over dry percentages for a sample is invalid, and if so, to select the other of said electronic and said density oven dry percentages as said verified oven dry percentage if said other oven dry percentage is valid.

45. An apparatus as recited in claim 44, wherein said data processor is operative to determine that said density oven dry percentage is invalid if said density oven dry percentage is greater than a predetermined value.

46. An apparatus as recited in claim 45, wherein the particulate material comprises wood chips and wherein said predetermined value of said density oven dry percentage is substantially 75%.

47. An apparatus as recited in claim 44, wherein said data processor is operative to determine said density oven dry percentage as a function of a bulk density reference, which is substantially equal to an average oven dry bulk density of the particulate material, and said wet bulk density of the sample, and to determine that said density oven dry percentage is invalid if said bulk density reference is outside a predetermined range.

48. An apparatus as recited in claim 47, wherein the particulate material comprises wood chips, and wherein said predetermined range of said bulk density reference is substantially 4 lbs/ft$^3$ to substantially 17 lbs/ft$^3$.

49. An apparatus as recited in claim 44, wherein said data processor is operative to determine said wet bulk density by monitoring said weight signal to determine a tare weight and a full weight of said sample box during each measurement cycle; and wherein said data processor is further operative to determine that said density oven dry percentage is invalid if said tare weight is less than a predetermined value during a plurality of successive measurement cycles.

50. An apparatus as recited in claim 44, wherein said data processor is operative to determine that said electronic oven dry percentage is invalid if said density oven dry percentage is also invalid and if said moisture signal is outside a predetermined range.

51. An apparatus as recited in claim 50, wherein the particulate material comprises wood chips, and wherein said predetermined range of said moisture signal is substantially 25% to substantially 75%.

52. An apparatus as recited in claim 44, wherein said data processor is operative to determine that said electronic oven dry percentage is invalid if said conductivity signal is greater than a predetermined value.

53. An apparatus as recited in claim 52, wherein the particulate material comprises wood chips, and wherein said predetermined value of said conductivity signal is substantially 49.

54. An apparatus as recited in claim 44, wherein said data processor is operative to determine that said electronic oven dry percentage is invalid if said density oven dry percentage is also invalid and if said wet bulk density of a sample is less than a predetermined value.

55. An apparatus as recited in claim 54, wherein the particulate material comprises wood chips, and wherein said predetermined value of said wet bulk density is substantially 6 lbs/ft$^3$.

56. An apparatus as recited in claim 44, wherein said data processor is operative to determine that said electronic oven dry percentage is invalid if said density oven dry percentage is also invalid and frozen moisture is detected in a sample.

57. An apparatus as recited in claim 44, wherein said data processor is operative to inhibit the selection of said verified oven dry percentage for a sample if both said electronic and said density oven dry percentages therefor are invalid.

58. An apparatus as recited in claim 44, further comprising means operatively associated with said data processor for causing said data processor to select either said density or said electronic oven dry percentages as said verified oven dry percentage.

59. An apparatus as recited in claim 44, further comprising output means operatively associated with said data processor for providing an output indication of said verified oven dry percentage for each of said plurality of samples.

60. An apparatus as recited in claim 59, wherein said output means comprises a printer.

61. An apparatus as recited in claim 59, wherein said output means additionally provides, for each sample, an output indication of the mode by which said verified oven dry percentage was selected.

62. An apparatus as recited in claim 61, wherein said output means comprises a printer.

63. An apparatus as recited in claim 44, further comprising output means operatively associated with said data processor for providing an output indication of the reason why either of said "electronic" and said "density" oven dry percentages are invalid for a sample.

64. An apparatus as recited in claim 63, wherein said output means comprises a printer.

65. An apparatus as recited in claim 44, wherein said data processor is operative to latch said detection of frozen moisture for a plurality of measurement cycles successive to a measurement cycle in which said detection of frozen moisture was first made.

66. An apparatus as recited in claim 44, wherein said data processor is operative to monitor said weight signal to determine the tare weight of said sample box during each measurement cycle, to test each thus-determined tare weight for a tare weight violation, and to inhibit the selection of said verified oven dry percentage in any measurement cycle following that in which a tare weight violation has been detected.

67. An apparatus as recited in claim 66, wherein said data processor is operative to detect said tare weight violation if the tare weight determined during a measurement cycle is less than a predetermined low limit.

68. An apparatus as recited in claim 67, wherein said data processor is operative to select said electronic oven dry percentage as said verified oven dry percentage if said tare weight violation persists for a predetermined number of successive measurement cycles.

69. An apparatus as recited in claim 66, wherein said data processor is operative to detect said tare weight violation if the tare weight determined during a measurement cycle is greater than a predetermined high limit.

70. An apparatus as recited in claim 66, wherein said data processor is operative to detect said tare weight violation if the tare weight determined during a measurement cycle has shifted by a predetermined amount from that determined during a preceding measurement cycle.

71. An apparatus as recited in claim 66 further comprising output means operatively associated with said data processor, and wherein said data processor is operative to cause said output means to provide a warning indication upon detection of a tare weight violation.

72. An apparatus as recited in claim 34, wherein said data processor is operative to determine an oven dry bulk density during each measurement cycle as a function of said verified oven dry percentage for a sample and said wet bulk density for that sample.

73. An apparatus as recited in claim 72, further comprising output means operatively associated with said data processor, and wherein said data processor is operative to cause said output means to provide an output indication of said verified oven dry percentage and said oven dry bulk density for each of said plurality of samples.

74. An apparatus as recited in claim 34, wherein said data processor is operative to determine said density oven dry percentage for each sample as a function of a bulk density reference, substantially equal to an average oven dry bulk density of the particulate material, and said wet bulk density of the sample, and to determine said electronic oven dry percentage as a function of said moisture signal for each sample and a correction factor, said correction factor being chosen so that an average of said electronic oven dry percentages for a plurality of samples of the particulate material is substantially equal to an average oven dry percentage of the particulate material as determined by oven testing.

75. An apparatus as recited in claim 74, further comprising memory means operatively associated with said data processor for storing said bulk density reference and said correction factor.

76. An apparatus as recited in claim 75, further comprising data entry means operatively associated with said data processor for entering said bulk density reference and said correction factor into said memory means.

77. An apparatus as recited in claim 76, wherein said data entry means is further adapted to enter an oven dry percentage determined by oven testing into said data processor, and wherein said data processor is operative to correct said bulk density reference and said correction factor stored in said memory means in accordance with the thus-entered oven dry percentage determined by oven testing.

78. An apparatus as recited in claim 34, wherein said data processor is operative to inhibit selection of said verified oven dry percentage if either of said density or said electronic oven dry percentages are invalid.

79. An apparatus for determining a verified oven dry percentage of each of a plurality of successive samples of particulate material, said apparatus comprising:
    a sample box for selectively receiving, retaining, and discharging a sample of the particulate material;
    a weight sensor operatively associated with said sample box for providing a weight signal related to the weight of said sample box;
    a temperature sensor operatively associated with said sample box for providing a temperature signal related to the temperature of a sample within said sample box;
    an impedance measurement apparatus operatively associated with said sample box for providing a moisture signal related to the electrical impedance of a sample within said sample box;
    timer means for providing a timing signal establishing a plurality of successive measurement cycles;
    a data processor operating under control of a stored program for:
        receiving said weight, temperature, moisture and timing signals;
        controlling said sample box so that said sample box receives, retains and discharges a sample of the particulate material during each measurement cycle;
        determining the wet bulk density of each sample from said weight signal;
        determining an electronic oven dry percentage for each sample from said moisture signal;
        determining a density oven dry percentage for each sample from said wet bulk density thereof;
        determining if either of said electronic and said density oven dry percentages are invalid;
        testing said temperature signal, said electronic oven dry percentage and said density oven dry percentage to detect the presence of frozen moisture in any sample;
        determining a degree of frozenness factor for a sample from said electronic and density oven dry percentages therefor;
        if said electronic and said density oven dry percentages for a sample are each valid, and if a detection of frozen moisture has been made for the sample, selecting as said verified oven dry percentage a quantity equal to said density oven dry percentage for the sample, modified in accordance with said degree of frozenness factor therefor;
        if said electronic and said density oven dry percentages are each valid for a sample and if a detection of frozen moisture has not been made for the sample, selecting as said verified oven dry percentage for the sample an average of said electronic and said density oven dry percentages;
        if said electronic oven dry percentage is valid for a sample and if said density oven dry percentage for the sample is invalid, selecting said electronic oven dry percentage as said verified oven dry percentage;
        if said density oven dry percentage for a sample is valid and said electronic oven dry percentage for the sample is invalid, selecting said density oven dry percentage as said verified oven dry percentage; and,
    output means operatively associated with said data processor for providing an output indication of said verified oven dry percentage for each of said plurality of samples.

80. An apparatus as recited in claim 79, wherein said data processor is further operative to determine an oven dry bulk density for each sample as a function of said verified oven dry percentage for the sample and said wet bulk density of the sample.

81. An apparatus as recited in claim 80, wherein said output means is operative to provide an output indication of said oven dry bulk density for each sample.

82. An apparatus as recited in claim 79, further comprising:
    memory means adapted to store, under control of said data processor, a plurality of supplier-related data entries, each said supplier-related data entry including a bulk density reference which is substantially equal to an average oven dry bulk density of particulate material from a given supplier, and also including a correction factor for that supplier;
    data and command entry means operatively associated with said data processor and adapted to enter said supplier-related data entries into said memory means, and further adapted to provide a supplier indication to said data processor which represents the identity of a supplier whose particulate material is being sampled; and, wherein said data processor is operative:
        to retrieve that one of said plurality of supplier-related data entries from said memory means that corresponds to said supplier indication;
        to determine said density oven dry percentage as a function of said bulk density reference is the thus-retrieved supplier data entry and said wet bulk density for each sample; and,
        to determine said electronic oven dry percentage as a function of said moisture signal for a sample and said correction factor in the thus-retrieved supplier-related data entry.

83. An apparatus as recited in claim 82, wherein said memory means is further adapted to store, under control of said data processor, a density-only command in each said supplier-related data entry; wherein said data and command entry means is adapted to provide a density-only command to said data processor along with said supplier indication; and, wherein said data processor is responsive to said density-only command to store said density-only command in that one of said plurality of supplier-related data entries corresponding to said supplier indication and to select said density oven dry percentage as said verified oven dry percentage for all samples of particulate material from a supplier if said density-only command has been entered into the corresponding supplier-related data entry.

84. An apparatus as recited in claim 82 or claim 83, wherein said memory means is further adapted to store, under control of said data processor, a plurality of load-related data entries, each said load-related data entry being itself related to one of said plurality of supplier-related data entries so as to establish a supplier/load combination, with each said load-related data entry including statistics data for a load of particulate material from the corresponding supplier; wherein said data and command entry means is further adapted to provide a load indication to said data processor; and, wherein said data processor is responsive to said load indication to determine and store said statistics data in that one of said plurality of load-related data entries that correspond to the thus-indicated load.

85. An apparatus as recited in claim 84, wherein said data processor is further operative to determine an oven dry bulk density for each sample as a function of said verified oven dry percentage for the sample and said wet bulk density of the sample, and to determine and store an average oven dry bulk density in that one of said plurality of load-related data entries that corresponds to the thus-indicated load.

86. An apparatus as recited in claim 85, wherein said data processor is adapted to monitor an output signal from a weightometer, said weightometer output signal representing the passage of a predetermined increment of weight past said sample box; and, wherein said data processor is further operative to determine from said weightometer output signal the total wet weight of the thus-indicated load, to determine the total dry weight of the thus-indicated load from said total weight and said average oven dry bulk density for the load, and to store said total weight and said total dry weight in that one of said plurality of load-related data entries that corresponds to the thus-indicated load.

87. An apparatus as recited in claim 84, wherein said data and command entry means is further adapted to provide an output load data command to said data processor, and wherein said data processor is responsive to said output load data command to cause said output means to provide an indication of said statistics data in each of said plurality of load-related data entries in said memory means.

88. An apparatus as recited in claim 87, wherein said data and command entry means is further adapted to provide an erase load data command to said data processor, and wherein said data processor is responsive to said erase data command to clear all load-related data entries from said memory means if said output load data command has previously been provided to said data procesor.

89. An apparatus as recited in claim 84, wherein said memory means is further adapted to store, under control of said data processor, a plurality of sample taken data entries; wherein said data and command entry means is operative to provide a sample taken command to said data processor; and, wherein said data processor is responsive to said sample taken command: to store, in one of said plurality of sample taken data entries, said electronic and density oven dry percentages determined in the measurement cycle being processed at the time that said sample taken command is provided, and, a supplier code relating to the thus-indicated supplier; to assign a sample ID number to said one of said plurality of sample taken data entries, and to cause said output means to provide an output indication of said one of said plurality of sample taken data entries.

90. An apparatus as recited in claim 89, wherein said data and command entry means is further adapted to enter said sample ID number and an oven dry percentage determined by oven testing corresponding to that sample into said data processor; and, wherein said data processor is operative: to retrieve the supplier code, the electronic oven dry percentage, and the density oven dry percentage from the sample taken data entry that corresponds to the thus-entered sample ID number; and, to update the values of said bulk density reference and said correction factor in that one of said plurality of supplier-related data entries that corresponds to the supplier in the thus-retrieved supplier code in accordance with the thus-entered oven dry percentage by oven testing.

91. An apparatus as recited in claim 84, wherein said data and command entry means is further adapted to provide an all electronic only command to said data processor; and, wherein said data processor is responsive to said all electronic only command to select said electronic oven dry percentage as said verified oven dry percentage for all subsequent samples of the thus-indicated load.

92. An apparatus as recited in claim 84, wherein said data and command entry means is further adapted to provide an all density only command to said data processor; and, wherein said data processor is responsive to said all density only command to select said density oven dry percentage as said verified oven dry percentage for all subsequent samples of the thus-indicated load.

93. An apparatus as recited in claim 82, wherein said data and command entry means comprises a keyboard and a display.

94. An apparatus as recited in claim 79, wherein said output means comprises a printer.

* * * * *

UNITED STATES PATENT AND TRADEMARK OFFICE
CERTIFICATE OF CORRECTION

PATENT NO. : 4,354,244

DATED : October 12, 1982

INVENTOR(S) : Christoper S. Miller et al.

It is certified that error appears in the above-identified patent and that said Letters Patent are hereby corrected as shown below:

Column 2, line 52, delete "-" and insert --=--.
        Column 5, line 68, delete "determining" and insert --determine--.
        Column 8, line 43, after "held" insert --above--.
        Column 11, line 3, after "turn" insert --is--.
                line 18, delete "At" and insert --As--.
        Column 13, line 16, delete "input" and insert --inputs--.
                line 54, delete "," and insert --.--;
                line 57, delete "conprises" and insert --comprises--.
        Column 14, line 37, delete "as" and insert --was--.
        Column 15, Table I, fourteenth line, before "electronic" insert --(--.
        Column 16, line 20, delete "is" and insert --in--.
        Column 18, Table III, eleventh line, delete "> " and insert -- $\geq$ --.
        Column 19, Table III - continued, fifth line, after "START NEW LOAD" insert --key--;
                line 21, delete "as" and insert --was--;
                line 24, delete "pressured" and insert --processed--;
                line 30, delete "do," and insert --so,--.
        Column 20, Table IV, seventeenth line, before "display" insert --,--;
        Column 21, Table IV - continued, twenty-third line, delete the comma after "lines'"
                line 46, delete "are" and insert --and--.
                line 62, delete "return" and insert --returns--.

UNITED STATES PATENT AND TRADEMARK OFFICE
CERTIFICATE OF CORRECTION

PATENT NO. : 4,354,244

DATED : October 12, 1982

INVENTOR(S) : Christoper S. Miller et al.

It is certified that error appears in the above-identified patent and that said Letters Patent are hereby corrected as shown below:

Column 22, line 37, after "used" insert --)--.
Column 23, line 19, delete "sampe" and insert --sample--.
Column 24, line 48, delete "cuase" and insert --cause--.
Column 25, line 37, delete "microrprocessor" and insert --microprocessor--.
Column 27, lines 1 and 2, delete "complemennt" and insert --complement--.
        line 10, delete "frozeness" and insert --frozenness--.
        line 12, delete "elctronic" and insert --electronic--.
Column 30, line 27, after "268" insert --,--.
Column 32, line 57, delete "a" and insert --an--.
Column 37, line 14, delete "in", first occurrence, and insert --is--.
        line 40, after "to" insert --be--.
        line 44, after "it" insert --to--.
Column 38, lines 29 & 30, delete "NEWBDREFDEV = (4 = BDREFDEV + DELT-W )/5" and insert -- NEWBDREFDV = (4 + BDREFDEV + DELTW )/5--.
        line 43, delete "and", first occurrence).
Column 43, line 52 (Claim 34, line 33), delete "over" and insert --oven--.
Column 44, line 40 (Claim 44, line 3), delete "over" and insert --oven--.
Column 48, line 47 (Claim 82, line 22), delete "is" and insert --in--.
Column 49, line 32 (Claim 86, line 9), before "weight" insert --wet--.
        line 34 (Claim 86, line 11), before "weight" insert --wet--.
        line 53 (Claim 88, line 8), delete "procesor" and insert --processor--.

Signed and Sealed this

Twenty-second Day of February 1983

|SEAL|

Attest:

GERALD J. MOSSINGHOFF

Attesting Officer     Commissioner of Patents and Trademarks